US008404659B2

(12) United States Patent  (10) Patent No.: US 8,404,659 B2
Kauppinen et al.  (45) Date of Patent: *Mar. 26, 2013

(54) PHARMACEUTICAL COMPOSITIONS FOR TREATMENT OF MICRORNA RELATED DISEASES

(75) Inventors: Sakari Kauppinen, Smørum (DK); Niels Abrahamsen, Vanløse (DK); Elisabeth S. Hildebrandt-Eriksen, Skibby (DK); Martin Munk, Karlslunde (DK)

(73) Assignee: Santaris Pharma A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/921,339

(22) PCT Filed: Mar. 9, 2009

(86) PCT No.: PCT/EP2009/052728
§ 371 (c)(1),
(2), (4) Date: Nov. 29, 2010

(87) PCT Pub. No.: WO2009/109665
PCT Pub. Date: Sep. 11, 2009

(65) Prior Publication Data
US 2011/0077288 A1  Mar. 31, 2011

Related U.S. Application Data

(60) Provisional application No. 61/034,745, filed on Mar. 7, 2008.

(51) Int. Cl.
*C12N 15/11* (2006.01)
(52) U.S. Cl. .................................................. 514/44 A
(58) Field of Classification Search ................ 514/44 A
See application file for complete search history.

(56) References Cited

U.S. PATENT DOCUMENTS

| | | | |
|---|---|---|---|
| 4,914,210 A | 4/1990 | Levenson et al. | |
| 4,920,115 A | 4/1990 | Nestler et al. | |
| 4,962,029 A | 10/1990 | Levenson et al. | |
| 5,506,212 A * | 4/1996 | Hoke et al. .................. | 514/44 A |
| 5,919,795 A | 7/1999 | Chang et al. | |
| 6,030,785 A | 2/2000 | Katze et al. | |
| 6,121,283 A | 9/2000 | Chang et al. | |
| 6,284,458 B1 | 9/2001 | Anderson et al. | |
| 6,423,489 B1 | 7/2002 | Anderson et al. | |
| 6,433,159 B1 | 8/2002 | Anderson et al. | |
| 7,087,229 B2 | 8/2006 | Zhao et al. | |
| 7,307,067 B2 | 12/2007 | Sarnow et al. | |
| 2003/0068320 A1 | 4/2003 | Dingivan | |
| 2004/0204356 A1 | 10/2004 | Guenzler-Pukall et al. | |
| 2005/0069522 A1 | 3/2005 | Colonno et al. | |
| 2005/0182005 A1 | 8/2005 | Tuschl et al. | |
| 2005/0227934 A1 | 10/2005 | Stoffel et al. | |
| 2005/0261218 A1 | 11/2005 | Esau et al. | |
| 2005/0288245 A1 * | 12/2005 | Sarnow et al. ................. | 514/44 |
| 2006/0035212 A1 | 2/2006 | Balakireva | |
| 2006/0035858 A1 | 2/2006 | Geary et al. | |
| 2006/0040989 A1 | 2/2006 | Meerpoel et al. | |
| 2006/0058266 A1 | 3/2006 | Manoharan et al. | |
| 2006/0185027 A1 | 8/2006 | Bartel et al. | |
| 2006/0265771 A1 | 11/2006 | Lewis et al. | |
| 2007/0049547 A1 | 3/2007 | Esau et al. | |
| 2009/0082297 A1 | 3/2009 | Lioy et al. | |
| 2009/0143326 A1 | 6/2009 | Obad et al. | |
| 2009/0298916 A1 | 12/2009 | Kauppinen et al. | |
| 2010/0004320 A1 | 1/2010 | Elmen et al. | |
| 2010/0280099 A1 | 11/2010 | Elmèn et al. | |
| 2010/0286234 A1 | 11/2010 | Elmen et al. | |
| 2010/0298410 A1 | 11/2010 | Obad et al. | |
| 2010/0330035 A1 | 12/2010 | Hildebrandt-Eriksen et al. | |

FOREIGN PATENT DOCUMENTS

| | | |
|---|---|---|
| EP | 0 699 751 A1 | 3/1996 |
| EP | 1 099 442 A2 | 5/2001 |
| EP | 0 662 157 B1 | 6/2001 |
| EP | 1 222 309 B1 | 7/2005 |
| EP | 1747023 B1 | 1/2011 |
| EP | 1931782 B1 | 1/2011 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 02/28875 A2 | 4/2002 |
| WO | WO02/081494 A1 | 10/2002 |
| WO | WO 02/094250 A2 | 11/2002 |
| WO | WO 03/006475 A2 | 1/2003 |
| WO | WO 03/011887 A2 | 2/2003 |
| WO | WO 03/029459 A2 | 4/2003 |

(Continued)

OTHER PUBLICATIONS

Abelson, J., at al., "Sequence Variants in SLITRK1 Are Associated with Tourette's Syndrome," *Science* 310:317-320, American Assn. for the Advancement of Science, United States (2005).

Alvarez-Garcia, I. and Miska, E., "MicroRNA functions in animal development and human disease," *Development* 132:4653-4662, The Company of Biologists, Ltd., United Kingdom (2005).

Brennecke, J., et al., "Principles of MicroRNA-Target Recognition," *PLoS Biology* 3:E85/0404-E85/0418, Public Library of Science, United States (2005).

(Continued)

*Primary Examiner* — J. E. Angell
(74) *Attorney, Agent, or Firm* — Sterne, Kessler, Goldstein & Fox P.L.L.C.

(57) ABSTRACT

The present invention provides compositions and methods of treatment of diseases that are sensitive to drugs that down-regulate the function of microRNA's, mRNA, non-coding RNA, or viral genomes. In particular, it has been discovered that a very long term effect of an anti microRNA oligonucleotide may be obtained when administered to a primate. Therefore, the present invention relate to pharmaceutical compositions and methods for treatment of primates, including humans wherein the compositions are administered with a long time interval.

49 Claims, 10 Drawing Sheets

FOREIGN PATENT DOCUMENTS

Figure 1:
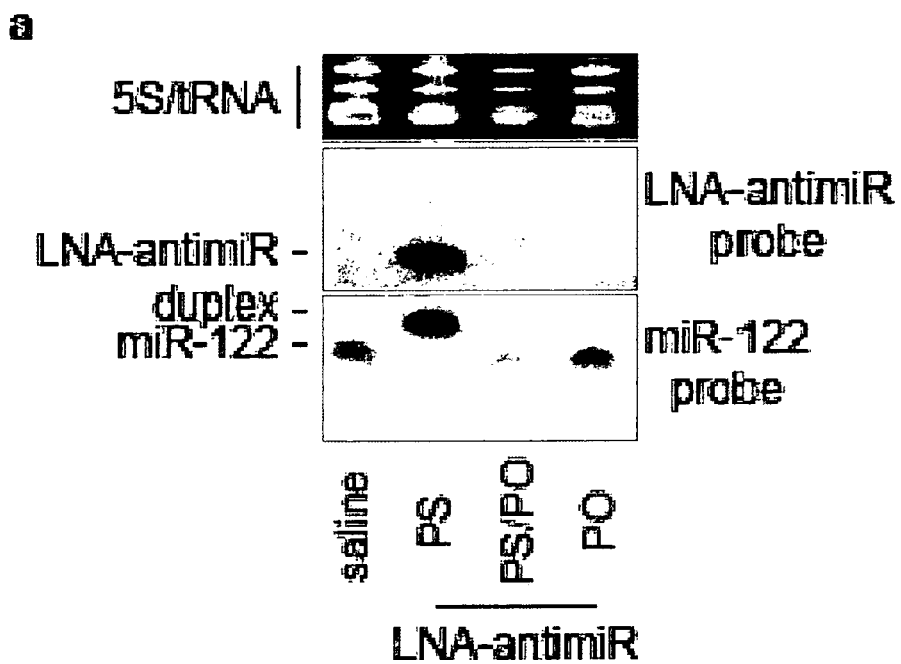
Figure 1:
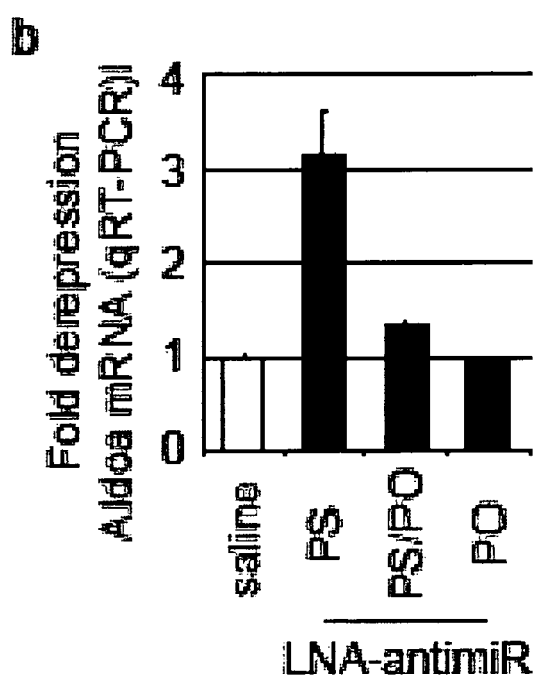
Figure 1:
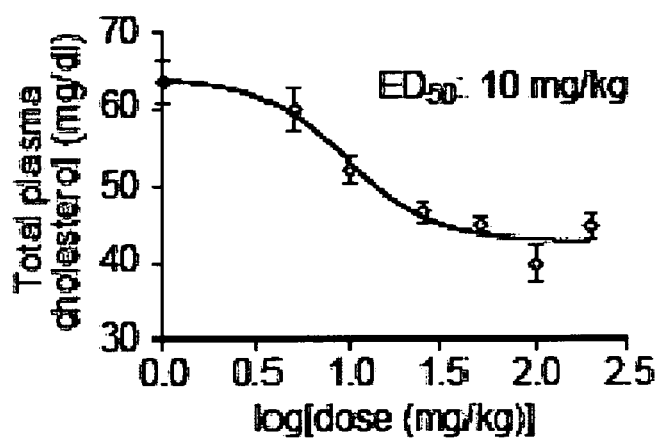
Figure 1:
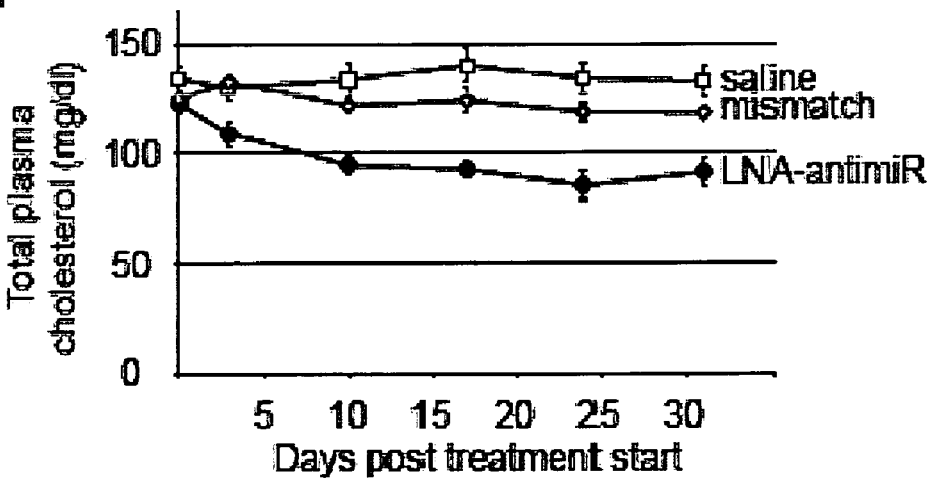
Figure 1:
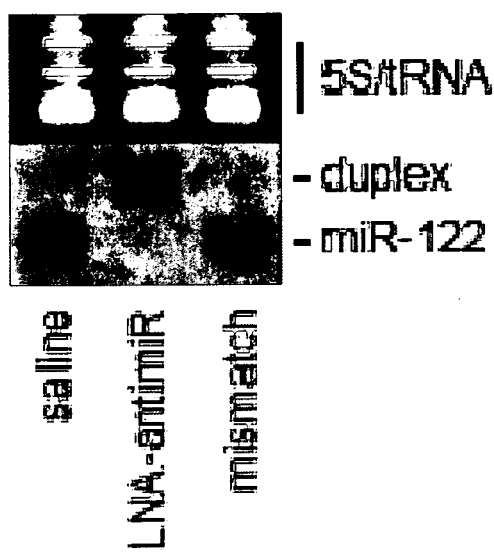
Figure 1:
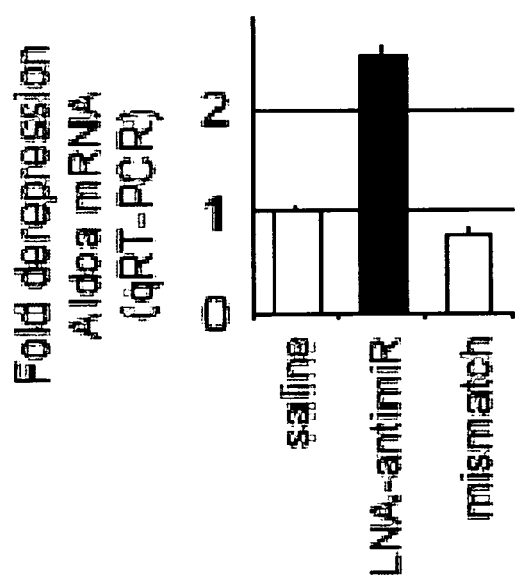
Figure 1:
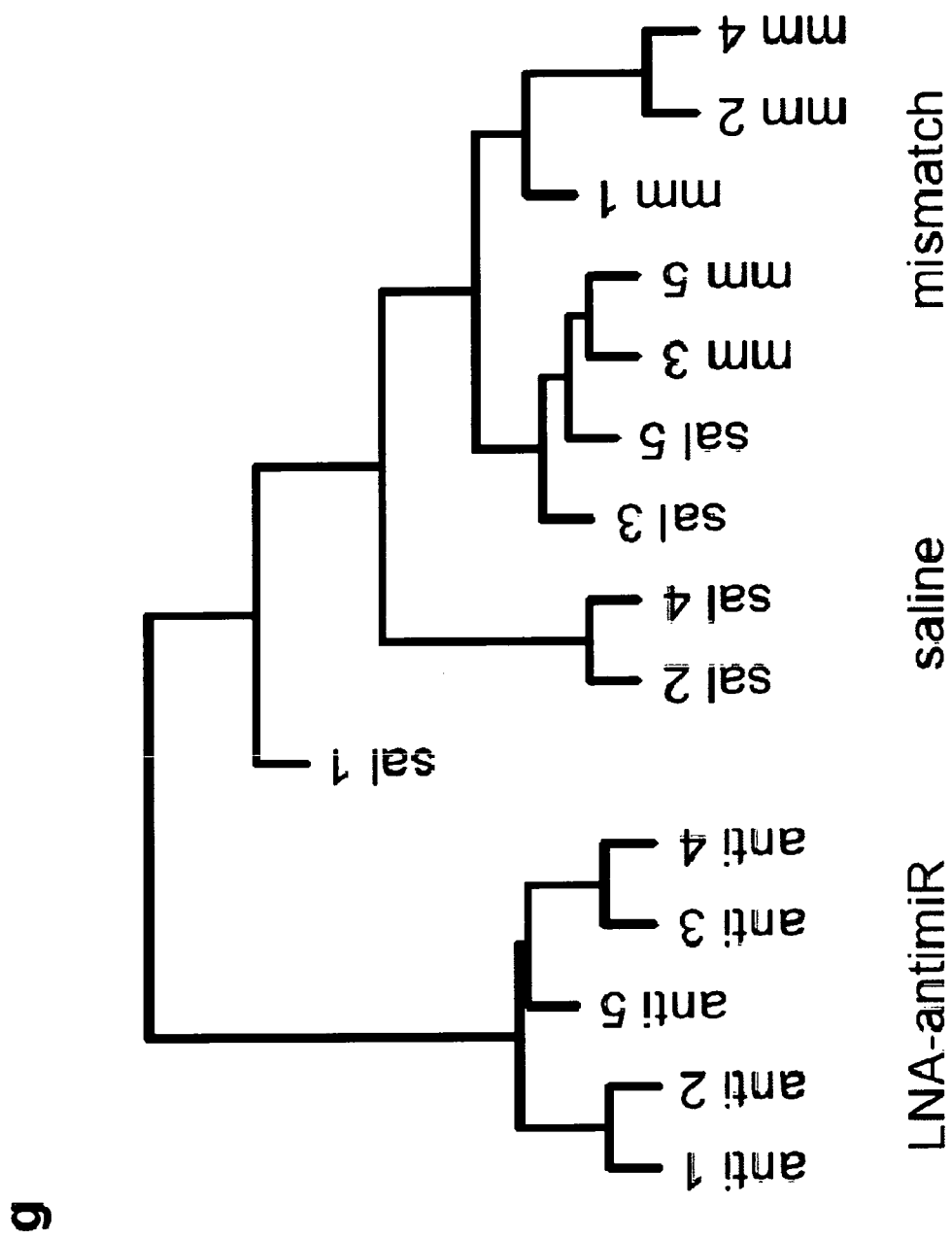
Figure 1:
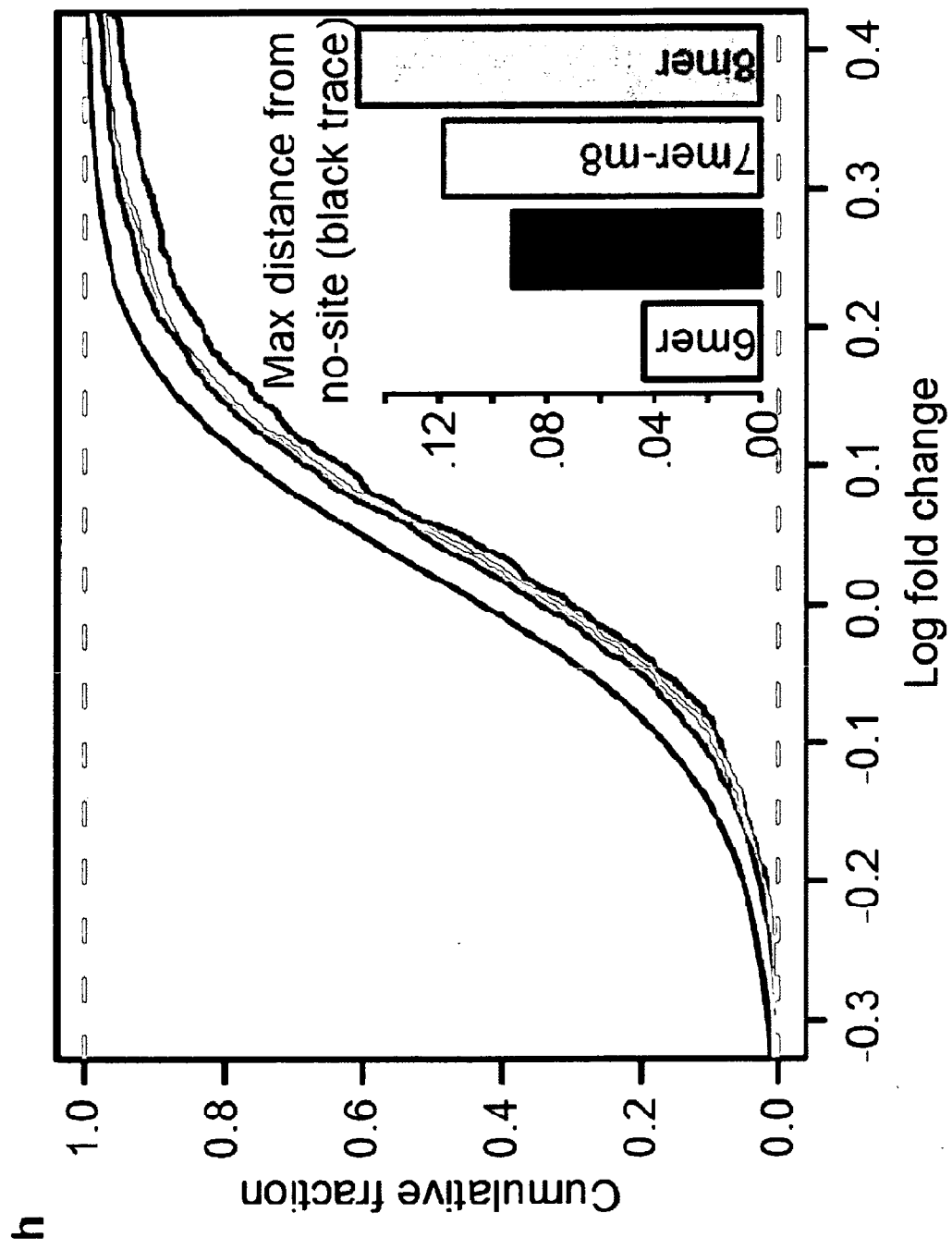

| WO | WO 03/070750 A2 | 8/2003 |
|---|---|---|
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2004/076622 A2 | 9/2004 |
| WO | WO 2005/013901 A2 | 2/2005 |
| WO | WO 2005/013905 A2 | 2/2005 |
| WO | WO 2005/023986 A2 | 3/2005 |
| WO | WO 2005/103298 A2 | 3/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/078139 A2 | 8/2005 |
| WO | WO 2005/079397 A2 | 9/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/027776 A2 | 3/2006 |
| WO | WO 2006/036916 A | 4/2006 |
| WO | WO 2006/053430 A1 | 5/2006 |
| WO | WO 2006/069584 A2 | 7/2006 |
| WO | WO 2006/093526 A2 | 9/2006 |
| WO | WO 2006/112872 A2 | 10/2006 |
| WO | WO 2006/113910 A2 | 10/2006 |
| WO | WO 2006/133022 A2 | 12/2006 |
| WO | WO 2006/137941 A2 | 12/2006 |
| WO | WO 2007/021896 A2 | 2/2007 |
| WO | WO 2007/027775 A2 | 3/2007 |
| WO | WO 2007/027894 A2 | 3/2007 |
| WO | WO 2007/031081 A2 | 3/2007 |
| WO | WO 2007/031091 A2 | 3/2007 |
| WO | WO 2007/090073 A2 | 8/2007 |
| WO | WO 2007/112753 A2 | 10/2007 |
| WO | WO 2007/112754 A2 | 10/2007 |
| WO | WO 2007/134181 A2 | 11/2007 |
| WO | WO 2007/146511 A2 | 12/2007 |
| WO | WO 2008/025025 | 2/2008 |
| WO | WO 2008/034122 A2 | 3/2008 |
| WO | WO 2008/034123 A2 | 3/2008 |
| WO | WO 2008/046911 A2 | 4/2008 |
| WO | WO 2008/057234 A2 | 5/2008 |
| WO | WO 2008/061537 A2 | 5/2008 |
| WO | WO 2008/074328 A2 | 6/2008 |
| WO | WO 2008/091703 A2 | 7/2008 |
| WO | WO 2008/113832 A2 | 9/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |
| WO | WO 2009/043353 A2 | 4/2009 |
| WO | WO 2009/032083 A1 | 12/2009 |
| WO | WO 2010/012667 A2 | 4/2010 |

OTHER PUBLICATIONS

Calin, G., et al., "A MicroRNA Signature Associated with Prognosis and Progression in Chronic Lymphocytic Leukemia," *N. Engl. J. Med.* 353:1793-1801, Massachusetts Medical Society, United States (2005).

Christensen, U. and Pederson, E., "Intercalating nucleic acids containing insertions of 1-O-(1-pyrenylmethypglycerol: stabilisation of dsDNA and discrimination of DNA over RNA," *Nucleic Acids Res.* 30:4918-4925, Oxford University Press, United Kingdom (2002).

Crooke, S., "Chapter 3: In Vitro Cellula Uptake, Distribution, and Metabolism of Oligonucleotides," in *Antisense Research and Application* 131:103-140, Springer-Verlag, Berlin, Germany (1998).

Czech, M., "MicroRNAs as Therapeutic Targets," *N. Engl. J. Med.* 354:1194- 1195, Massachusetts Medical Society, United States (2006).

Eisenberg, I., et al., "Distinctive patterns of microRNA expression in primary muscular disorders," *Proc. Natl. Acad. Sci. USA* 904:17016-17021, National Academy of Sciences, United States (2007).

Elmén, J., et al., "Antagonism of microRNA-122 in mice by systemically administered LNA-antimiR leads to up-regulation of a large set of predicted target mRNAs in the liver," *Nucleic Acids Res.* 36:1153-1162, Oxford University Press, United Kingdom (2007).

Elmén, J., et al., "LNA-mediated microRNA silencing in non-human primates," *Nature* 452:896-900, Nature Publishing Group, United Kingdom (2008).

Elmén, J., et al., "LNA-mediated microRNA silencing in non-human primates," *Nature 45* [Supplementary Information], 33 pages, Nature Publishing Group, United Kingdom (2008).

Esau, C., et al., "miR-122 regulation of lipid metabolism revealed by in vivo antisense targeting," *Cell Metab.* 3:87-98, Elsevier, Inc., The Netherlands (2006).

Esquela-Kerscher, A. and Slack, F., "Oncomirs- microRNAs with a role in cancer," *Nat. Rev. Cancer* 6:259-269, Nature Publishing Group, United Kingdom (2006).

Fabani, M., and Gait, M., "miR-122 targeting with LNA/2'-O-methyl oligonucleotide mixmers, peptide nucleic acids (PNA), and PNA-peptide conjugates," *RNA* 14:336-346, Cold Spring Harbor Laboratory Press, United States (2008).

Freier, S. and Altmann, K.-H., "The ups and downs of nucleic acid duplex stability: structure—stability studies on chemically-modified DNA: RNA duplexes," *Nucleic Acids Res.* 25:4429-4443, Oxford University Press, United Kingdom (1997).

Greene, T. and Wuts, P., *Protective Groups in Organic Synthesis*, 3rd ed., John Wiley & Sons, Chichester, England (1999).

Jopling, C., et al., "Modulation of Hepatitis C Virus RNA Abundance by a Liver-Specific MicroRNA," *Science* 309: 1577-1571, American Assn. for the Advancement of Science, United States (2005).

Krützfedt, J., et al., Silencing of microRNAs in vivo with 'antagomirs,' *Nature Letters* 438:685-689, Nature Publishing Group, United Kingdom (2005).

Krützfedt, J., et al., "Specificity, duplex degradation and subcellular localization of antagomirs," *Nucleic Acids Res.* 35:2885-2892, Oxford University Press, United Kingdom (2007).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society for Microbiology, United States (2003).

Lewis, B., et aL, "Conserved Seed Pairing, Often Flanked by Adenosines, Indicates that Thousands of Human Genes are MicroRNA Targets," *Cell 120*:15-20, Elsevier, Inc., The Netherlands (2005).

Manoharan, M., et al., "Novel Functionalization of the Sugar Moiety of Nucleic Acids for Multiple Labeling in the Minor Groove," *Tetrahedron Letters* 32:7171-7174, Pergamon Press, PLC., United Kingdom (1991).

Obad, S., at al., "Targeting of cancer-associated microRNAs using short LNA-antimiR oligonucleotides," *European Journal of Cancer Supplements* 6:142, 20th Meeting of the European Association for Cancer Research, Lyon, France, Jun. 5-8, 2008.

Pedersen, I., at al., "Interferon modulation of cellular microRNAs as an antiviral mechanism," *Nature* 449:919-922, Nature Publishing Group, United Kingdom (2007).

Petri, A., at al., "MicroRNA Silencing in Primates: Towards Development of Novel Therapeutics," *Can Res.* 69:393-395, American Association for Cancer Research, United States (2009).

Randall, G., et al., "Cellular cofactors affecting hepatitis C virus infection and replication," *Proc. Nati: Acad. Sci. USA* 104:12884-12889, National Academy of Sciences, United States (2007).

Shan, Y., et al., "Reciprocal Effects of Micro-RNA-122 on Expression of Heme Oxygenase-1 and Hepatitis C Virus Genes in Human Hepatocytes," *Gastroenterology* 133:1166-1174, W.B. Saunders, United States (2007).

Soifer, H., at al., "MicroRNAs in Disease and Potential Therapeutic Applications," *Mol.Ther.* 15:2070-2079, The American Society of Gene Therapy, United States (2007).

Uhlmann, E., "Recent advances in the medicinal chemistry of antisense oligonucleotides," *Curr. Opin. Drug Discov. Develop.* 3:203-213, Thomson Reuters (Scientific) Ltd., United Kingdom (2000).

van Rooij, E., et al., "Control of Stress-Dependent Cardiac Growth and Gene Expression by a MicroRNA," *Science 316*:575-579, American Association for the Advancement of Science, United States (2007).

Weiler, J., et al., "Anti-miRNA oligonucleotides (AMOs): ammunition to target miRNAs implicated in human disease?" *Gene Ther. 13*:496-502, Nature Publishing Group, United Kingdom (2006).

Yang, B., et al., "The muscle-specific microRNA miR-1 regulates cardiac arrhythmogenic potential by targeting GJA1 and KCNJ2," *Nat. Med. 13*:486-491(2007).

International Search Report for International Application No. PCT/DK2007/000168, European Patent Office, mailed on Jan. 28, 2008.

International Search Report for International Application No. PCT/DK2007/000169, European Patent Office, mailed on Jul. 3, 2008.

International Search Report for International Application No. PCT/DK2008/000345, European Patent Office, mailed on Oct. 7, 2009.

The Written Opinion of the International Searching Authority for International Application No. PCT/DK2008/000345, European Patent Office, mailed on Oct. 7, 2009.

International Search Report for International Application No. PCT/DK2008/000344, European Patent Office, mailed on Oct. 7, 2009.

International Search Report for International Application No. PCT/EP2009/052728, European Patent Office, mailed on Jul. 31, 2009.

Office Action mailed on Jul. 13, 2010 in U.S. Appl. No. 12/296,084, inventors Elmen et aL, filed Sep. 10, 2009.

Office Action mailed on Nov. 5, 2010 in U.S. Appl. No. 12/400,625, inventors Kauppinen et al., filed Mar. 9, 2009.

Co-pending U.S. Appl. No. 12/767,631, filed Apr. 26, 2010, United States Patent Office, Alexandria, VA., United States (Not Published).

Abelson, J. et al., "Sequence Variants in *SLITRK1* Are Associated with Tourette's Syndrome." *Science 310*: 317-320, American Assn. for the Advancement of Science, United States (2005).

Agrawal, S. and Zhao, Q., "Antisense therapeutics," Curr. Opin. Chem. Biol. 2: 519-528, Elsevier, United Kingdon (1998).

Agrawal, S., et al., "Mixed-backbone oligonucleotides as second generation antisense oligonucleotides: In vitro and in vivo studies", Proc. Natl. Acad. Sci. USA, vol. 94, pp. 2620-2625, National Acadamy of Sciences, United States (1997).

Agrawal, S. et al., "Pharmacolinetics, biodistricution, and stability of oligodeoxynucleotide phosphorothioates in mice", Proc. Natl. Acad. Sci. USA 88:7595-7599, National Academy of Sciences, United States (1991).

Agrawal, S., "Importance of nucleotide sequences and chemical modi¢cations of antisense oligonucleotides" Biochimica et Biophysica Acta 1489:53-68, Elsevier Pub. Co., The Netherlands (1999).

Akhtar S., "Antisense Technology:Selection and delivery of optimally acting antisense oligonucleotides", Journal of Drug Targeting 5: 225-234, Informa Healthcare, United States (1998).

Alvarez-Garcia, I. and Miska, E., "MicroRNA functions in animal development and human disease," *Development 132*:4653-4662, The Company of Biologists, Ltd., United Kingdon (2005).

Ambros, V., "The functions of animal microRNAs," *Nature 431*:350-355, Nature Publishing Group, United Kingdom (2004).

Ameres, S.L., et al., "Molecular Basis for Target RNA Recognition and Clevage by Human RISC," Cell 130:101-112, Cell Press, United States (2007).

Asangani, I.A., et al., "MicroRNA-21 (miR-21) post-transcriptionally downregulates tumor suppressor Pdcd4 and stimulates invasion, intracasation and metastasis in colorectal cancer," Oncogene 27:2128-2136, Nature Publishing Group, United Kingdom (2008).

Bai, S., et al., "MicroRNA-122 inhibits tumorigenic Properties of Hepatocellular Carcinoma Cells and Sensitizes These Cells to Sorafenib," J. Biol. Chem. 284(46):32015-32027, American Society for Biochemistry and Molecular Biology, United States (2009).

Bartel, D., "MicroRNAs: Genomics, Biogenesis, Mechanism, and Function," *Cell 116*:281-297, Cell Press, United States (2004).

Bartenschlager R. and Pietschmann T., "Efficient hepatitis C virus cell culture system: What a difference the host cell makes," Proc. Natl. Acad. Sci. 102:9739-9740, National Academy of Sciences, United States (2005).

Bartosch, B. et al., "Cell Entry of Hepatitis C Virus Requires a Set of Co-receptors That Include the CD81 Tetraspanin and the SR-B1 Scavenger Receptor," J. Biol. Chem. 278:41624-41630, American Society for Biochemistry and Molecular Biology, United States (2003).

Beaucage, L. and Iyer, R., "Advances in the Synthesis of Oligonucleotides by the Phosphoramidite Approach," *Tetrahedron 48*:2223-2311, Pergamon Press, United Kingdom (1992).

Beaucage, L. and Iyer, R., "The Synthesis of Modified Oligonucleotides by the Phosphoramidite Approach and Their Applications," *Tetrahedron 49*:6123-6194, Pergamon Press, United Kingdom (1993).

Bennett, C.F., "MicroRNAs as therapeutic targets," Abstracts of Papers, 234th ACS National Meeting, Boston, MA, United States, Aug. 19-23, 2007, CARB-047, Database: CAPLUS (2007).

Bennett, C., et al., "Antisense Oligonucleotide-based Therapeutics," Gene and Cell Therapy (2nd Edition), pp. 347-374, Editor: N S Templeton, Marcel Dekker, Inc. (2004).

Bhat, B., et al., "2'-O-Methoxyethyl/2'—Fluoro Modified Oligonucleotides Result in More Potent Inhibition of micro RNA-122 in Vivo: A Target Implicated in HCV Replication," *Nucleic Acids Symposium Series 52*:69, Oxford University Press, Unitted Kingdom (2008).

Boehm, M., and Slack, F., "A Developmental Timing MicroRNA and Its Target Regulate Life Span in *C. elegans,*" *Science 10*:1954-1957, American Assn. for the Advancement of Science, United States (2005).

Boutla, A., et al., "Developmental defects by antisense-mediated inactivation of mictro-RNAs 2 and 13 in *Drosophila* and the identification of putative target genes," *Nucleic Acids Res. 31*:4973-4980, Oxford University Press, United Kingdom (2003).

Boutla, A., et al., "Short 5'-phosphorylated double-stranded RNAs include RNA interference in *Drosophila,*" *Curr. Biol. 11*:1776-1780, Cell Press, United States (2001).

Braasch, D., et al., "Antisense inhibition of gene expression in cells by oligonucleotides incorporating locked nucleic acids: effect of mRNA target sequence and chimera design," *Nucleic Acids Res. 30*:5160-5167, Oxford University Press, United Kingdom (2002).

Branch, A., and Rice, C., "Antisense Gets a Grip on miR-122 in Chimpanzees," *Sci. Transl. Med. 2*:1-4, American Assn. for the Advancement of Science, United States (2010).

Branch, A.D., A good antisense molecule is hard to find, TIBS 23:45-50, Elsevier Trends Journals, United Kingdom (1998).

Brennecke, J., et at, "*bantam* Encodes a Developmentally Regulated microRNA that Controls Cell Proliferation and Regulates the Proapoptotic Gene *hid* in *Drosophila,*" *Cell 113*:25-36, Cell Press, United States (2003).

Brennecke, J., et al., "Principles of MicroRNA-Target Recognition," *PLoS Biology 3*: LE85/0404-E85/0418, Public Library of Science, United States (2005).

Calin, G., et aL, "Frequent deletions and down-regulation of micro-RNA genes *miR15* and *miR16* at 13q14 in chronic lymphocytic leukemia," *Proc. Natl. Acad. Sci. USA 99*:15524-15529, National Academy of Sciences, United States (2002).

Calin, G., et al., "Human microRNA genes are frequently located at fragile sites and genomic regions involved in cancers," *Proc. Natl. Acd. Sci. USA 101*:2999-3004, National Academy of Sciences, United States (2004).

Calin, G., at al., "A MicroRNA Signature Associated with Prognosis and Progression in Chronic Lymphocytic Leukemia," *N. Engl. J. Med. 353*:1793-1801, Massachusetts Medical Society, United States (2005).

Calin, G. and Croce, C., "MicroRNA signatures in human cancers," *Nat. Rev. Cancer 6*:857-866, Nature Publishing Group, United Kingdom (2006).

Chan, J., et al., "MicroRNA-21 Is an Antiapoptotic Factor in Human Glioblastoma Cells," *Cancer Res. 65*: 6029-6033, American Association for Cancer Research, United States (2005).

Chang, J., et al., "Liver-Specific MicroRNA miR-122 Enhances the Replication of Hepitis C Virus in Nonhepatic Cells," J. Virol. 82(16):8215-8223, American Society For Microbiology, United States (2008).

Chang, J., et al., "miR-122, a Mammalian Liver-Specific microRNA, is Processed from *hcr* mRNA and May Downregulate the High Affinity Cationic Amino Acid Transporter CAT-1," *RNA Biol. 1*:106-113, Landes Bioscience, United States (2004).

Chen, X., "A MicroRNA as a Translational Repressor of *APETALA2* in *Arabidopsis* Flower Development," *Science 303*:2022-2025, American Assn. for the Advancement of Science, United States (2004).

Chen, J.-F., et al., "The role of microRNA-1 and micro-RNA-133 in skeletal muscle proliferation and differentiation," *Nat. Genet. 38*:225-233, Nature Publishing Co., United States (2005).

Cheng, A., et al., "Antisense inhibition of human miRNAs and indications for an involvement miRNA in cell growth and apoptosis," *Nucleic Acids Res. 33*:1290-1297, Oxford University Press, United Kingdom (2005).

Choi, W -Y., et al., "Target Protectors Reveal Dampening and Balancing of Nodal Agonist and Antagonist by miR-430," Science DOI:10.1126/science.1147535, American Assn for the Advancement of Science. United States (2007).

Christensen, U. and Pedersen, E., "Intercalating nucleic acids containing insertions of 1-*O*-(1-pyrenylmethyl)glycerol: stabilisation of dsDNA and discrimination of DNA over RNA," *Nucleic Acids Res. 30*:4918-4925, Oxford University Press, United Kingdom (2002).

Connolly E. et al., "Elevated Expression of the miR-17-92 Polycistron and miR-21 in Hepadnavirus-Associated Hepatocellular Carcinoma Contributes to the Malignant Phenotype," Am. J. Pathol. 173(3):856-864, American Society for Investigative Pathology (2008).

Cook, P.D., "Antisense Medicinal Chemistry", In Antisense Research & Application, Edited by Stanley Crooke p. 51-101 (1998).

Corsten, M., et al., "MicroRNA-21 Knockdown Disrupts Glioma Growth in vivo and Displays Synergistic Cytotoxicity with Neural Precursor Cell-Delivered S-TRAIl in Human Gliomas," *Cancer Res. 67*:8994-9000, American Association for Cancer Research, United States (2007).

Coulouarn, C., et al., "Loss of miR-122 expression in liver cancer correlates with supression of the hepatic phenotype and gain of metastic properties," Oncogene 28:3526-36, Nature Publishing Group, United Kingdom (2009).

Crooke, R., "Chapter 3: In Vitro Cellular Uptake, Distribution, and Metabolism of Oligonucleotides," in *Antisense Research and Application 131*:103-140, Springer-Verlag, Germany (1998).

Crooke, S.T., "Mechnisms of Antisense Drug Action, an Introduction" in Antisense Technology, Principles, Strategies and Applications, Ed. Crooke S.T. p. 3-46 (2008).

Crooke, S.T., "An overview of Progree om Antisense Therapeutics", Antisense & Nucleic Acid Drug Development 8:115-122, Mary Ann Liebert, Inc., United States (1998).

Crooke S.T., "Basic Principles of Antisense Technology", in Antisense Technology, Principles, Strategies and Applications, Ed. Crooke S.T. p. 1-28 (2001).

Czech, M., "MicroRNAs as Therapeutic Targets," *N. Engl. J. Med. 354*:1194-1195, Massachusetts Medical Society, United States (2000).

Dass, C., "Vehicles for oligonucleotide delivery to tumours," *J. Pharm. Pharmacol. 54*:3-27, Pharmaceutical Press, United Kingdom (2002).

Davidson, N. and Shelness, G., "Apolipoprotein B: mRNA Editing, Lipoprotein Assembly, and Presecretory Degradion," *Annu. Rev. Nutr. 20*:169-193, Annual Reviews, United States (2000).

Davis, S., et al., "Improved targeting of miRNA with antisense oligonucleotides," *Nucleic Acids Res. 34*:2294-2304, Oxford University Press, United Kingdon (2006).

Davis, S., et al., "Potent inhibition of microRNA in vivo without degradation," *Neuclic Acids Res. 37*:70-77, Oxford University Press, United Kingdom (2008).

Davis, S., et al, "Potent inhibition of microRNA in vivo without degradation," *Nucleic Acids Res. 37*:70-77, Oxford University Press, United Kingdom (2008).

Deere, J., et al., "Antisense Prosphorodiamidate Morpholino Oligomer Length and Target Position Effects on Gene-Specific Inhibition in *Eschericia cole*," *Antimicrobal Agents and Chemotherapy 49*:249-255, American Society for Microbiology, United States (2005).

D Young & Co., Investigation of teachings of WO2008/061537 and WO2008/151639, Jan. 2009.

Diaz-Toledano, R., et al., "In vitro characterization of a miR-122-sensitive double-helical switch element in the 5' region of hepatitis C virus RNA," Nucl. Acids Res. 37(16):5498-5510, : Oxford University Press, United Kingdom (2009).

Els, P., et al., "Accumulation of miR-155 and *BIC* RNA in human B cell lymphomas," *Proc. Natl. Acad. Sci. USA 102*:3627-3632, National Academy of Sciences, United States (2005).

Eisenberg, I., et al., "Distinctive patterns of microRNA expression in primary muscular disorders," *Proc. Natl. Acad. Sci. USA 104*:17016-17021, National Academy of Sciences, United States (2007).

Elbashir, S., et al., "Analysis of gene function in somatic mammalian cells using small interfering RNAs" *Methods 26*:199-213, Academic Press, United States (2002).

Elmén, J., et al., "Locked nucleic acid containing antisense oligonucleotides enhance inhibition of HIV-1 genome dimerization and inhibit replication," *FEBS Letters 578*:285-290, Elsevier B.V., The Neverlands (2004).

Elmén, J., et at, "Antagonism of microRNA-122 in mice by systematically administered LNA-antimiR leads to up-regulation of a large set of predicted target mRNAs in the liver," *Nucleic Acids Res. 36*:1-10, Oxford University Press, United Kingdom (2007).

Elmén, J., et al., "LNA-antimiRs: Promising candidates for therapeutic intervention of disease-related microRNAs," [poster] 71st Symposium on Quantitative Biology; Regulatory RNAs, Cold Spring Harbor, New York, United States (May 2006).

Elmén, J., et al., "LNA-antimiRs: Promising candidates for therapeutic intervention of desease-related microRNAs," [presentation abstract] 71st Symposium on Quantitative Biology; Regulatory RNAs, Cold Spring Harbor, New York, United States (May 2006).

Elmén, J., et al , "Lna-antimiRs: Promising candidates for therapeutic interbention of disease-related microRNAs," [conference abstract] Nov. 1-2, 2006, MicroRNAs: Biology to Development and Disease, Peterhouse, University of Cambridge, UK (2006).

Elmén, J., et aL, "LNA-mediated microRNA silencing in non-human primates," *Nature 452*:896-900, Nature Publishing Group, United Kingdom (2008).

Esau, C., "MicroRNA-143 Regulates Adipocyte Differentiation," *J. Biol Chem. 279*:52361-52365, American Society for Biochemistry and Molecular Biology, United States (2004).

Esau, C., et al., "MicroRNA-143 Regulates Adipocyte Differentiation [Supplementary Methods]," *J. Biol. Chem. 279*, 25 pages, American Sociaty for Biochemistry and Molecular Biology, United Stated (2004).

Esau, C., et al., "Identification of microRNAs involved in adipocyte development using second-generation antisense oligonucleotides in an in vitro adipocyte differentiation model," [poster abstract] siRNAs and miRNAs Keystone Symposium, Keystone Resort, Colorodo United States (2004).

Esau, C., et al., "miR-122 regulation of lipid metabolism revealed by in vivo antisense targeting." *Cell Metab. 3*:87-98, Cell Press, United States (2006).

Esau, C., et al., "miR-122 regulation of lipid metabolism revealed by in vivo antisense targeting," [Supplemental data] *Cell Metab. 3*, 1 page, Cell Press, United States (2006).

Esau, C.C., and Monia, B.P., "Therapeutic potential for microRNAs," *Adv. Drug Deliv. Rev.59*:101-114, Elsevier Science Publishers, B.V., The Netherlands (2007).

Esau, C., "Inhibition of microRNA with antisense oligonucleotides,"*Methods 44*:55-60, Academic Press, United States (2008).

Esquela-Kerscher, A. and Slack, F., "Oncomirs—microRNAs with a role in cancer," *Nat. Rev. Cancer 6*:259-269, Nature Publishing Group, United Kingdom (2006).

Fabani, M., and Gait, M., "miR-122 targeting with LNA/2'-*O*- methyl oligonucleotide mixmers, peptide nucleic acids (PNA), and PNA-peptide conjugates," *RNA 14*:336-346, Cold Spring Harbor Laboratory Press, United States (2008).

U.S. Department of Health and Human Services, Food and Drug Administration, Center for Drug Evaluation and Research (CDER),"Guidance for Industry Antiviral Product Development—

Conducting and Submitting Virology Studies to the Agency," Jun. 2006, Clinical Antimicrobial (2006).

Feld, J., et al., "Ribavirin Improves Early Response to Pegintergeron Through Improved Interferon Signaling," *Gastroenterology* 139:154-162, W.B. Saunders, United States (2010).

Feld, J.J, and Hoofnagle, J. H., "Mechanism of action of interferon and ribavirin in treatment of hepatitis C", Nature 436: 967-72, Nature Publishing Group, United Kingdom (2005).

Fluiter, K. et al., "In vivo tumor growth inhibition and biodistribution studies of locked nucleic acid (LNA) antisnese oligonucleotides," Nucleic Acids Res. 31(3):953-962, Oxford University Press, United Kingdom (2003).

Fornari, F., et al., "MiR-122/Cyclin G1 Interaction Modulated p53 Activity and Affects Doxorubicin Sensitifity of Human Hepatocarcinoma Cells," *Cancel Res.* 69:5761-5767, American Assn. for Cancer Research, United States (2009).

Frankel, L.B., et al., "Programmed cell death 4 (PDCD4) is an important functional target of the microRNA miR-21 in breast cancer cells." J. Biol. Chem. 283:1026-1033, The American Society for Biochemistry and Molecular Biology, United States (2008).

Freier, S. and Altmann, K.-H., "The ups and downs of nucleic acid duplex stability: structure—stability studies on chemically-modified DNA: RNA deplexes," *Nucleic Acids Res.* 25:4429-4443, Oxford University Press, United Kingdom (1997).

Freier, S.M., "Methods of Selecting Sites in RNA for Antisense Targeting," *Antisense Drug Technology*, Edited by Stanley T. Crooke, CRC Press, ISBN: 978-0-8247-0566-4 (2001).

Frieden, M., et al., "Expanding the design horizon of antisense oligonucleotides with alpha-L-LNA," *Nucleic Acids Res.* 31:6365-6372, Oxford University Press, United Kingdom (2003).

Frieden, M. and Ørum, H. "Locked Nucleic Acid Holds Promise in the Treatment of Cancer," *Curr. Pharmac. Design* 14:1138-1142, Bentham Science Publishers, The Netherlands (2008).

Gabriely, G., et al., "MicroRNA 21 Promotes Glioma Invasion by Targeting Matrix Metalloproteinase Regulators," *Molec. Cell. Biol.* 28(17):5369-5380, American Society for Microbiology, United States (2008).

Galardi, S., et al., "miR-221 and miR-222 expression affects the proliferation potential of human prostate carcinoma cell lines by targeting p27Kip1" J. Biol. Chem. 282:23716-23724, The American Society for Biochemistry and Molecular Biology, United States (2007).

Geary, R.S., et aL, "Pharmacokinetic Properties of 29-O-(2-Methoxyethyl)-Modified Oligonucleotide Analogs in Rats," *J. Pharm. Exper. Therap.* 296(3):890-897, American Society for Pharmacology and Experimental Therapeutics, United States (2001).

Gentleman, R., et al., "Bioconductor: open software development for computational biology and bioinformatics," *Genome Biol.* 5:R80, BioMed Central Ltd., United Kingdom (2004).

Gerwitz, A M., "Nucleic Acid Therapeutics: State of the art and future prospects", Blood 92:712-736, American Society of Hematology, United States (1998).

Giles, R., et al, "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Giraldez, A., et al., "MicroRNAs Regulate Brain Morphogenesis in Zebrafish," *Science 308*: 833-838, American Assn. for the Advancement of Science; United States (2005).

Girard M. et al., "miR-122, a paradigm for the role of microRNAs in the liver," *J. Hepatol.* 48:648-656 (2008).

Gramantieri, L., et al., "Cyclic G1 is a Target of miR-122a, a MicroRNA Frequently Down-regulated in Human Hepatoceliular Carcinoma," *Cancer Res.* 64(13):5092-6099, American Assn. for Cancer Research, United States (2007).

Greene, T. and Wuts, P., *Protective Groups in Organic Synthesis*, [Table of Contents], 3rd ed., John Wiley & Sons, Chichester, England (1999).

Griffiths-Jones, S., "The microRNA Registry," *Nucleic Acids Res.* 32:D109-D111 (Database issue), Oxford University Press, United Kingdom (2004).

Griffiths-Jones, S., et al., "miRBase: microRNA sequences, targets and gene nomenclature," *Nucleic Acids Res.* 34:D140-D144 (Database issue), Oxford University Press, United Kingdom (2006).

Grimm, D. and Kay, M.A., "Therapeutic application of RNAi is mRNA targeting finally ready for prime time?" J. Clinic. Invest. 117(12):3633-3641, American Society for Clinical Investigation, United States (2007).

Grimson, A., et al., "MicroRNA Targeting Specificity in Mammals: Determinants beyond Seed Pairing," *Mol. Cell.* 27:91-105, Elsevier, Inc., The Netherlands (2007).

Hanecak, R., et al., "Antisense Oligonucleotide Inhibition of Hepatitis C Virus Gene Expression in Transformed Hepatocytes," *J. Viral.* 70:5203-5212, American Society For Microbiology, United States (1996).

Haussecker, D. and Kay, M., "miR-122 Continues to Blaze the Trail fro MicroRNA Therapeutics," *Molecular Therapy* 18:240-242, Nature Publishing Group, United States (2010).

He, L., et al., "A microRNA polycistron as a potential human oncogene," *Nature* 435:828-833, Nature Publishing Group, United Kingdom (2005).

Heid, C., et al., "Real-Time Quantitative PCR," *Genome Res.* 6:986-994, Cold Spring Harbor Laboratory Press, United States (1996).

Henke, J. I. et al., "microRNA-122 stimulates translation of hepatitis C virus RNA," *EMBO Journal* 27:3300-3310, Nature Pub. Group, United Kingdom (2008).

Hildebrandt-Eriksen, E.S., et al., "A unique Therapy for HCV inhibits mocroRNA-122 in Humans and Resits in HCV Suppression in Chronically Infected Chimpanzees: Results from Primate and First-in-Human Studies," *Hepatology* LB19, 50(6):12A, Wiley, United States (2009).

Hogrefe, R.I., "An antisense oligonucelotide primer", Antisense & Nucleic Acid Drug Development 9:351-357, Mary Ann Liebert, Inc., United States (1999).

Hornstein, E., et al:, "The microRNA *miR-196* acts upstream of Hoxb8 and Shh in limb development," *Nature* 438:671-674, Nature Publishing Group, United Kingdom (2005).

Horwich, M.D. and Zamore, P. D., "Design and delivery of antisense oligonucleotides to block microRNA function in cultured *Drosophila* and human cells," Nature Protocols 3(10):1537-1549, Nature Pub. Group, United Kingdom (2008).

Hu, Q., "Subcellular trafficking of antisesnse oligonucleotides and down-regulation of *bcl-2* gene expression in human melanoma cells using a fusogenic liposome delivery system," *Nucleic Acid Res.* 30:3632-3641, Oxford University Press, United Kingdom (2002).

Huang, H., et al., "Hepatitis C virus production by human hepatocytes dependent on assembly and secretion of very low-density lipoproteins," *Proc. Natl. Acad. Sci. U.S.A.* 104:5848-5853, National Academy of Sciences, United States (2007).

Huber, W., et al., "Variance stabilization applied to microarray data calibration and to the quantification of differential expression," *Bioinformatics* 18:S96-S104, Oxford University Press, United Kingdom (2002).

Hutton, J., "Renaturation kinetics and thermal stability of DNA in aqueous solutions for formamide and urea," *Nucleic Acids Res.* 4:3537-3555, Oxford University Press, United Kingdom (1977).

Hutvágner, G., et al., "A Cellular Function for the RNA-Interference Enzyme Dicer in the Maturation of the *let-7* Small Temporal RNA," *Science* 293:834-838, American Assn. for the Advancement of Science, United States (2001).

Hutvágner, G., et aL, "Sequence-Specific Inihibition of Small RNA Function," *PLos Biology* 2:0465-0475, Public Library of Science, United States (2004).

Hutvagner, G., et al., "Sequence-specific inhibition of small RNA function," [poster abstract] siRNAs and miRNAs Keystone Symposium, Keystone Resort, Colorado United States (2004).

Hwang, H., et al., "Cell—cell contact globally activates microRNA biogenis," *Proc. Natl. Acad. Sci.* 106:7019-7021, National Academy of Sciences, United States (2009).

Ikeda, M., et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," J. Virol. 76(6):2997-3006, American Society for Microbiology, United States (2002).

Iliopoulos, D., et al., "MicroRNA-370 controls the expression of affects lipid metabolism," J. Lipid. Res. 51:1513-1523, American Society Molecular Biology, United States (2010).

Iorio, M., et al., "MicroRNA Gene Expression Deregulation in Human Breast Cancer," Cancer Res. 65:7065-7070, American Assn. for Cancer Research, United States (2005).

Ittig, D., et al., "Nuclear antisense effects in cyclophilin A pre-mRNA splicing by oligonucleotides: a comparison of tricyclo-DNA with LNA," Nucleic Acids Res. 32:346-353, Oxford University Press (2004).

Jackson, A. and Linsley, P., "The Therapeutic Potential of microRNA Modulation," discoverymedicine.com, assessed at http://www.discoverymedicine.com/Aimee-Jackson/2010/04/10/the-therepeutic-potential-of-microrna-modulation/, assesed on May 5, 2010, 7 pages.

Jepsen, J., et al., "Locked Nucleic Acid: A Potent Nucleic Acid Analog in Therapeutics and Biotechnology," Oligonucleotides 14:130-146, Mary Ann Liebert, Inc., United States (2004).

Jepsen, J.S., and Wengel, J., "LNA-Antisense rivals siRNA for gene silencing," Curr. Opin. Drug Discov. Develop. 7(2):1889-194, Thomson Reuters (Scientific) Ltd. United Kingdom (2004).

Jin, P., et al., "RNA and microRNAs in fragile X mental retardation," Nat. Cell Biol. 6:1048-1053, Nature Publishing Group, United States (2004).

Johansson, H., et al., "Target-specific arrest of mRNA translation by antisense 2'-O-alkyloligonucleotides," Nucleic Acids Res. 22: 4591-4598, Oxford University Press, United Kingdom (1994).

Johnson, C.D., et al., "The let-7 MicroRNA Represses Cell Proliferation Pathways in Human Cells," Cancer Research 67:7713-7722, American Association for Cancer Research, United States (2007).

Johnson, S., et al., "RAS Is Regulated by the let-7 MicroRNA Family," Cell 120:635-647, Cell Press, United States (2005).

Johnston, Jr., R., and Hobert, O., "A microRNA controlling left/right neuronal asymmetry in Caenorabditis elegans," Nature 426:845-849, Nature Publishing Group, United Kingdom (2003).

Jopling, C., "Regulation of hepatitis C virus by microRNA-122," Biochemical Society Transactions 36:1220-1223, Portland Press, United Kingdom (2008).

Jopling, C., et al., "Liver-specific microRNA122 Regulates Hepatitis C Viral RNA Abundance," p. 124, Sarnow, P. Conference: Translation Control, Cold Spring Harbor Laboratory, Cold Spring Harbor, New York, United States, Sep. 7-12, 2004.

Jopling, C., et al., "Modulation of Hepatitis C Virus RNA Abundance by a Liver-Specific MicroRNA," Science 309:1577-1571, American Assn. for the Advancement of Science, United States (2005).

Jopling, C. L., et al., "Positive and negative Modulation of Viral and Cellular mRNAs by liver-specific MicroRNA miR-122," Cold Spring Harbor Symposia on Quantitative Biology (71):369-376 (2006).

Jopling, C. L., "Position-Dependent Function for a Tandem MicroRNA miR-122-Binding Site Located in the Hepatitis C Virus RNA Genome," Cell Host and Microbe 4:77-85, cell Press, United States (2008).

Kauppinen, S., et al., "Locked nucleic acid (LNA): High affinity targeting of RNA for diagnostics and therapeutics," Drug Discovery Today: Technologies 2:287-290, Elsevier, Ltd., The Netherlands (2005).

Kauppinen, S., "Antogonizing microRNAs for therapeutics," Human Gene Therapy 19(10):163, M.A. Liebert, United States (2008).

Kauppinen, S., et al., "Locked Nucleic Acid: High-Affinity Targeting of Complementary RNA for RNomics," Handbook of Experimental Pharmacoloty, Springer-Verlag Berlin Heidelberg 173:405-422 (2006).

Kaur, H., et al., "LNA-modified oligonucleotides effectively drive intramolecular-stable hairpin to intermolecular-duplex state," Biochem. Biophys. Res. Comm. 352:118-122, Academic Press, United States (2007).

Ketting, R., et al., "Dicer functions in RNA interference and in synthesis of small RNA involved in developmental timing in C. elegans," Genes Dev. 15:2654-2659, Cold Spring Harbor Laboratory Press, United States (2001).

Khan, AA et al., "Transfection of small RNAs globally perturbs fene regulation by endogenous microRNAs," A144: 549-555, Nature Publishing Group, United States (2009).

Kinberger, G.A. et al., "Design, synthesis and in vivo results of chemically-modigied antisense oligonucleotides targeting microRNA-122", Abstracts of Papers 234th ACS Annual Meeting (2010).

Klein M E et al., "Homeostatic regulation of MeCP2 expression by a CREB-induced microRNA," Nat. Neurosci. 10(12):1513-1514, Nature Publishing Group, United States (2007).

Kloosterman, W., et al., "Substrate requirements for let-7 function in the developing zebrafish embryo," Nucleic Acids Res. 32:6284-6291, Oxford University Press, United Kingdom (2004).

Kloosterman, W. and Plasterk, R., "The Diverse Functions of MicroRNAs in Animal Development and Disease," Dev. Cell 11:441-450, Elsevier, Inc., The Netherlands (2006).

Kloosterman, W., et al., "In situ detection of miRNAs in amimal embroys using LNA-modified oligonucleotide probe," Nat. Methods 3:27-29, Nature Publishing Group, United States (2006).

Kocerha, J., et al, "MicroRNA-219 modulates NMDA receptor-mediated neurobehavioral dysfunction," Proc. Natl. Acad. Sci. USA 106:3507-3512, National Academy of Sciences, United States (2008).

Kocerha, J. et al., "microRNAs in CNS Disorders", Neuromol. Med. 11:162-172, Humana Press, United States (2009).

Koch, T. and Ørum, H. "Locked Nucleic Acid", Drug Technology, Principles, Strategies and Applications, Ed. Crooke S.T. pp. 519-564 (2008).

Kock, T. et al., "Locked Nucleic Acid: Properties and Therapeutic Aspects", In Therapeutic Oligonucleotides (2008), 103-141. Editor(s) Kurreck, Jens. Publisher Royal Society of Chemistry, UK.

Krukemeyer, M., et al., "Description of B lymphocytes and plasma cells, complement, and chemokines/receptors in acute liver allograft rejection," Transplation 78:65-70, Lippincott Williams & Wilkins, United States (2004).

Krützfeldt, J., et al., Silencing of microRNAs in vivo with 'antagomirs,' Nature Letters 438:685-689, Nature Publishing Group, United Kingdom (2005).

Krützfeldt, J., et al., Specificity, duplex degradation and subcellular localization of antagomirs, Nucleic Acids Res. 35:2885-2892, Oxford University Press, United Kingdom (2007).

Krützfeldt, J., et al., "Strategies to determine the biological function of microRNAs," Nature Genetics 38:S14-S19, Nature Publishing Group, United Kingdom (2006).

Kurreck, J., et al, "Design of antisense oligonucleotides stabilized by locked nucleic acids," Nucleic Acids Res. 30:1911-1918, Oxford University Press, United Kingdom (2006).

Kutay, H., et al. , "Downregulation of miR-122 in the Rodent and Human Hepatocellular Carcinomas," J. Cell. Biol. 99:671-678, Wiley-Liss, United States (2006).

Kwon, C., et al., "MicroRNA1 influences cardiac differentiation in Drosophila and regulated Notch signaling," Proc. Natl. Acad. Sci. USA 102:18986-18991, National Academy of Sciences, United States (2005).

Lagos-Quintana, M., et al., "Identification of Tissue-Specific MicroRNAs from Mouse," Curr. Biol. 12: 735-739. Elsevier Science Ltd., The Netherlands (2002).

Lagos-Quintana, M. et al., "Identification of Novel Genes for Small Expressed RNAs", Science 294: 853-858, American Assn. for the Advancement of Science, United States (2001).

Landthaler, M., et al., "The Human DiGeorge Syndrome Critical Region Gene 8 and its D. Melanogaster Homolog Are Required for miRNA Biogenesis," Curr. Biol. 14:2162-2167, Elsevier Ltd., The Netherlands (2004).

Landthaler, M., et al., "Sequence-specific inhibition of microRNA and siRNA-induced RNA silencing" [poster abstract] siRNAs and miRNAs Keystone Symposium, Keystone Resort, Colorado United States (2004).

Lanford, R.E. et al., "Antagonizing MicroRNA-122 and Tratment of Heoatitic C Virus Infection", Hepatology 51:1461-1465, Wiley, United States (2010).

Lanford, R., et al., "Antiviral Effect and Virus-Host Interactions in Response to Alpha Interferon, Gamma Interferon, Poly(l)-poly(C), Tumor Necrosis Factor Alpha, and Ribavirin in Hepatitis C Virus Subgenormic Replicons," J. Virol. 77:1092-1104, American Society For Microbiology, United States (2003).

Lanford, R., et al., "Lack of response to exogenous interferon-alpha in the liver of chimpanzees chronically infected with hepatitis C virus," *Hepatology 46*:999-1008, Wiley, United States (2007).

Lanford, R., et al., "Therapeutic Silencing of MicroRNA-122 in Primates with Chronic Hepatitis C Virus Infection," *Science 327*:198-201, American Assn. for the Advancement of Science, United States (2010).

Lanford, R. E. et al., "The Accelerating Pace of HCV Research: A Summary of the 15th International Symposium on Hepatitis C Virus and Related Viruses", Gastroenterology 136: 9-16, W.B. Saunders, United States (2009).

Leaman, D., et al, "MiRNA function in *Drosophila* development," [poster abstract] siRNAs and miRNAs Keystone Symposium, Keystone Resort, Colorado, United States (2004).

Leaman, D., et al., "Antisense-Mediated Depletion Reveals Essential and Specific Functions of MicroRNAs in *Drosophila* Development," *Cell 121*: 1097-1108, Cell Press, United States (2005).

Lecellier, C.-H., et al., "A Cellular MicroRNA Mediates Antiviral Defense in Human Cells," *Science 308*:557-560, American Assn. for the Advancement of Science, United States (2005).

Lecellier, C.-H., et al., "A Cellular MicroRNA Mediates Antiviral Defense in Human Cells," [Supporting online material] *Science 308*:557-560, American Assn. for the Advancement of Science, United States (2005).

Lee, Y.S. and Dutta, A. "The tumor suppressor microRNA let-7 represses the HMGA2 oncogene" *A182*:1025-1030, Cold Spring Harbor Laboratory Press, United States (2007).

Lee, Y., et al., "The nuclear RNase III Drosha initiates microRNA processing," *Nature 425*:415-419, Nature Publishing Group, United Kingdom (2003).

Lee, Y., et al., "Depletion of Human Micro-RNA miR-125b Reveals That it is Critical for the Proliferation of Differentiated Cells but Not for the Down-regulation of Putative Targets during Differentiation," *J. Biol. Chem. 280*:16635-16641, The American Society for Biochemistry and Molecular Biology, Inc., United States (2005).

Le Sage, C., et al., "Regulation of the CDKN1B/p27 tumor suppressor by miR-221 and miR-222 promotes cancer cell proliferation" *Cell6*:3699-3708, Nature Publishing Group, United Kingdom (2007).

Lewis, B., et al, "Conserved Seed Pairing, Often Flanked by Adenosines, Indicates Thousands of Human Genes are MicroRNA Targets," *Cell 120*:15-20, Elsevier, Inc., The Netherlands (2005).

Li, X. and Carthew, R., "A microRNA Mediates EGF Receptor Signaling and Promotes Photoreceptor Differentiation in the *Drosophila* Eye," *Cell 123*:1267-1277, Elsevier, Inc., The Netherlands (2005).

Lim, L., et al., "Microarray analysis shows that some microRNAs downregulate large numbers of target mRNAs," *Nature 433*:769-773, Nature Publishing Group, United Kingdom (2005).

Lima, W., et al., "Combinatorial Screening and Rational Optimization for Hybridization to Folded Hepatitis C Virus RNA of Oligonucleotides with Biological Antisense Activity," *J. Biol. Chem. 272*:626-638, American Society for Biochemistry and Molecular Biology, United States (1997).

Lin, C. J.-F., et al., "mir-122 targets an anti-apoptotic gene, Bcl-w. in human hepatocellular carcinoma cell lines," *Biochem Biophys. Res. Comm.* DOI:10.1016/j.bbrc.2008.07 15, Academic Press, United States (2008).

Lindenbach, B.D., et al., "Complete Replication of Hepatitis C Virus in Cell Culture", Science 309:623-626, American Assn. for the Advancement of Science, United States (2005).

Lisziewicz, J., et al., "Long-term treatment of human immunodeficiency virus-infected cells with antisense oligonucleotide phosphorothioates," *Proc. Natl. Acad. Sci. 90*:3860-3864, Academy of Sciences, United States (1993).

Liu, J., et al., "The microRNAs of *Caenorhabditis elegans*," [powerpoint slides], 36 slides, Sep. 22, 2004.

Love, T.M., et al., "Not miR-ly small RNAs: Big potential for microRNAs in therapy," *J. Allergy Clin. Immunol. 121*:309-310, Mosby, United States (2008).

Lu, J., et al., "MicroRNA expression profiles classify human cancers," *Nature 435*:834-838, Nature Publishing Group, United Kingdom (2005).

Lupberger, J., et al., "RNAi—A powerful tool to unravel hepatitis C virus-host interactions within the infectious live cycle", J. Hepatol. 48(3):523-525, Elsevier, United Kingdom (2007).

Machin, E. et al., "Masking the 5' terminal nucleotides of the hepatitis C virus genome by an unconventional microRNA-target RNA complex," Proc. Nati, Acad, Sci. USA 108:3193-3193, National Academy of Sciences, USA (2011).

McLeod, B.W. et al., "The 'real world' utility of miRNA patents: lessons learned from expressed sequence tags," Nature Biotechnology 29: 129-133, Nature Publishing Group, United Kingdom (2011).

Manoharan, M., et al.,"Novel Functionalization of the Sugar Moeity of Nucleic Acids for Multiple Labeling in the Minor Groove," *Tetrahedron Letters 34*:7171-7174, Pergamon Press, PLC., United Kingdom (1991) .

Martinez, J., et al., Single-Stranded Antisense siRNAs Guide Target RNA Cleavage in RNAi, *Cell 110*:563-574, Cell Press, United States (2002).

Matz, M., et al., "Early post-transplant urinary IP-10 expression after kidney transplantation is predictive of short- and long-term graft function," *Kidney Int. 69*:1683-1690, Nature Publishing Group (2006).

Mayr, C., et al., "Disrupting the Pairing Between let-7 and Hmga2 Enhances Oncogenic Transformation," *Science 315*:1576-1579, American Assn. for the Advancement of Science, United States (2007).

McMANUS, M., and Sharp, P., "Gene Silencing in Mammals by Small Interfering RNAs," *Nat. Rev. Genet. 3*:737-747, Nature Publishing Group, United Kingdom (2002).

Meister, G., "Sequence-specific inhibition of microRNA- and sRNA-induced RNA silencin" *RNA 10*:644-650, Cold Spring Harbor Press, United States (2004).

Metzler, M., et al., "High expression of precursor microRNA-155/BIC RNA in children with Burkitt lymphoma", Genes Chromosomes Cancer 39: 167-169, Wiley-Liss, Unites States (2004).

Michael, M., et al., "Reduced Accumulation of Specific MicroRNAs in Colorectal Neoplasia," *Mol. Cancer Res. 1*:882-891, American Association for Cancer Research, Unites States (2003).

Mirnezami, a. H. F. et al., "MicroRNAs: Key players in carcinogenesis and novel therapeutic targets", Eur. J. Surg. Oncol. 35: 339-347, Elsevier, Netherlands (2009).

Miska, E.A., et al., "Most *Caenorhabditis elegans* microRNAs are individually not essential for development or viability", PLoS Genet. 3(12): e215, Public Library of Science, United States (2007).

Moore, S., "Antisense.' touted as medical hope, but critics ask if promise in reasonable," *Wall Street Journal (Eastern edition)*, New York, NY, May 10, 1996 p. A5A, 6 pgs.

Möröy, T., et al., "Structure and expression of *hcr*, a locus rearranged with *c-myc* in a woodchuck hepatocellular carcinoma," *Oncogene 4*:59-65, Nature Publishing Group, United Kingdom (1989).

Mourelatos, Z., et al., "miRNPs: a novel class of ribonucleoproteins containing numerous microRNAs," *Genes Dev. 16*:720-728, Cold Spring Harbor Laboratory Press, United States (2002).

Naguibneva, I., et al., "MicroRNAs in terminal muscle differentiation," [poster abstract] siRNAs and miRNAs Keystone Symposium, Keystone Resort, Colorado United States (2004).

Naguibneva, I., et al., "The microRNA rniR-181 targets the homeobox protein Hox-A11 during mammalian myoblast differentiation," *Nature Cell Biol. 8*:278-284, Nature Publishing, Group, United States (2006).

Naguibneva, I., et al., "The microRNA miR-181 targets the homeobox protein Hox-A11 during mammalian myoblast differentiation," *Nature Cell Biol. 8* [Supplementary Information], Nature Publishing Group, United States (2006).

Naguibneva, I., et. al., "An LNA-based loss-of-function assay for micro-RNAs," Biomed. & Pharmacother. 60:633-638, Elsevier Ltd., United Kingdom (2006).

Nelson, P., "The microRNA world: small is mighty," *Trends in Biochem. Sci. 28*:534-540, Elsevier Ltd., United Kingdom (2003).

Neuman, B., et al., "Antisense Morpholino-Oligomers Directed against the 5' End of the Genome Inhibit Coronavirus Proliferation and Growth," *J Virol. 78*:5891-5899, American Society for Microbiology, United States (2004).

Nielsen S. U. et al., "Association between Hepatitis C Virus and Very-Low-Density Lipoprotein (VLDL)/LDL Analyzed in Iodixanol Density Gradients", Journal of Virology 80: 2418-2428, American Society for Microbiology, United States (2006).

Niepmann, M. "Activation of hepatitis C virus translation by a liver-specific microRNA", Cell Cycle 8: 1473-1477, Landes Bioscience, United States (2009).

Norman, K., and Sarnow, P., "Hepatitis C virus' Achilles' heel-dependence on liver-specifife microRNA miR-122," *Cell Res.* 20:247-249, Nature Publishing Group, United Kingdom (2010).

Norman, K L. and Sarnow, P. Modulation of Hepatitis C Virus RNA Abundance and the Isoprenoid Biosynthesis Pathway by MicroRNA miR-122 Involves Distinct Mechanisms, Journal of Virology 34: 366-670, American Society for Microbiology, United States (2010).

Nulf, C. and Corey, D., "Intracellular inhibition of hepatitis C virus (HCV) internal ribosomal entry site (IRES)-dependent translation by peptide nucleic acids (PNAs) and locked nucleic acids (LNAs)," *Nucleic Acids Res.* 32:3792-3798, Oxford University Press, United Kingdom (2004).

Obad, S., et al., "Targeting of cancer-associated microRNAs using short LNA-antimiR oligonucleotides," *European Journal of Cancer Supplements* 6:142, 20th Meeting of the European Association for Cancer Research, Lyon, France, Jun. 5-8, 2008.

Ørom, U., et al., "LNA-modified oligonucleotides mediate specific inhibition of microRNA function," *Gene* 372:137-141, Elsevier, Inc., The Netherlands (2006).

Quellet, D., et al., "MicroRNAs in Gene Regulation: When the Smallest Governs it All," Article ID 69616, *Journal of Biomedicine and Biotechnology* 2006:1-20, Hindawi Publishing Corporation, Unites States (2006).

Pan, Q. et al., "New Therapeutic opportunities for Hepatitis C based on small RNA", World J. Gastroenterol. 13: 4431-4436, Baishideng Pub, China (2007).

Pan, Q., et al. "Prospects of RNAi and microRNA-based therapies for hepatitis C," *Expert Opin. Biol. Ther.* 9(6):713-724, Informa Healthcare, United Kingdom (2009).

Park, J.-K., et al., "Antisense Inhibition of microRNA-21 or -221 Arrests Cell Cycle, Induces Apoptosis, and Sensitizes the Effects of Gemcitabine in Pancreatic Adenocarcinoma," *Pancreas* 38(7):e190-e199, Lippincott Williams & Wilkins, United States (2009).

Pasquinelli, A.E., et al., "Conservation of the sequence and temporal expression of let-7 heterochronic regulatory RNA," *Nature* 408:86-89, Nature Publishing Group, United Kingdom (2000).

Paushkin, S., et al, "The SMN complex, an assemblyosome of ribonucleoproteins," *Curr. Opin. Cell Biol.* 14:305-312, Elsevier Science Ltd., United Kingdom (2002).

Pavio, N. and Lai, M M.C., "The hepatitis C virus persistence: how to evade the immune system?" *J. Biosci.* 28:287-304, Springer, India (2003).

Pedersen, D., et aL, "Preparation of LNA Phosphoramidites," *Snthesis* 6:802-808, Thieme/Academic Press, Germany (2002).

Pedersen, D., and Koch, T., "Analogues of LNA (Locked Nucleic Acid). Synthesis of the 2'Thio-LNA Thymine and 5-Methyl Cytosine Phosphoramidites," Synthesis 4:578-582, Thieme/Academic Press, Germany (2003).

Pedersen, I., et al., "Interferon modulation of cellular microRNAs as an antiviral mechanism," *Nature* 449:919-923, Nature Publishing Group, United Kingdom (2007).

Petri, A., et al., "MicroRNA Silencing in Primates: Towards Development of Novel Therapeutics," *Can Res.* 69:393-395, American Association for Cancer Research, United States (2009).

Pietschmann, T. et al., "Construction and characterization of infectious intragenotypic and intergenotypic hepatitis C virus chimeras", Proc. Natl. Acad. Sci. USa 103: 7408-7413, National Academy of Sciences, United States (2006).

Pietschmann, T. et al., "Production of Infectious Genotype 1b Virus Particles in Cell Culture and Impairment by Replication Enhancing Mutations", PLoS Pathogens 5:1-14, Public Library of Science, United States (2009).

Poy, M., "A pancreatic islet-specific microRNA regulates insulin secretion," *Nature* 432:226-230, Nature Publishing Group, United Kingdom (2004).

Prakash, T., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med Chem.* 53:1636-1650, American Chemical Society, United States (2010).

Regulus Therapeutic, Press release, "Regullus Therapeutics and GlaxoSmithKline Establish New Collaboration to Develop and Commercialize microRNA Therapeutics Targeting miR-122," Feb. 25, 2010, 2 pages.

Randall, G., et al., "Cellular cofactors affecting hepatitis C virus infection and replication," Proc. Natl. Acad. Sci. USA 104:12884-12889, National Academy of Sciences, United States (2007).

Robertson B. et al., "Specificity and functionality of microRNA inhibitors", Silence 1:10, BioMed Central, United Kingdom (2010).

Roberts, A.P.E. & Jopling, C.L., "Targeting viral infection by microRNA inhibition," *Genome Biology* 1:201, Biomed Central Ltd., England (2010).

Rosenbohm, C., et al., "Synthesis of 2'-amino-LNA: a new strategy," *Org. Biomol. Chem.* 1:655-663, Royal Sociaty of Chemistry, United Kingdom (2003).

Saeed, A., et al., "TM4: A Free, Open-Source System for Microarray Data Management and Analysis," *Bio Techniques* 34:374-378, Informa Healthcare USA, Inc., United Kingdom (2003).

Samuel, D., "Hepatitis C, Interferon, and Risk of Rejection After Liver Transplantation," *Liver Transpl.* 10:868-887, Wiley InterScience, United States (2004).

Santaris Pharma, In house Memot to attorney at Horton, Jan. 27, 2009 santaris memo 2009 (confidential).

Santaris Pharma, "LNA-antimiRs—Towards Effective MicroRNA Antagonist," Nature Genetics, vol. 38 Ad, , microRNA Supplement, Jun. 2006 [powerpoint slide], 1 page.

Sarasin-Filipowicz, M., et al., "Decreasedlevels of microRNA miR-122 in individuals with hepatitis C responding poorly to interferon therapy." *Nature Medicine* 15(1):31-33, Nature Publishing Company, United States (2009).

Sarnow, P. et al., "MicroRNAs: expression, avoidance and subversion by vertebrate viruses," *Nat. Rev. Microbiol.* 4:651-659, Nature Publishing Group, England (2006).

Sazani, P., et al., "Nuclear antisense effects of neutral, anionic and cationic oligonucleotide analogs," *Nucelic Acids. Res.* 29:3965-3974, Oxford University Press, United Kingdom (2001).

Schwarz, D., et al., "Evidence that siRNAs Function as Guides, Not Primers, in the *Drosophila* and Human RNAi Pathways," *Mol. Cell* 10:537-548, Cell Press, United States (2002).

Seth, P., et al., "Synthesis and Biophysical Evaluation of 2',4'-Constrained 2'O-Methoxyethyl and 2',4'-Constrained 2'O-Ethyl Nucleic Acid Analogues," *J. Org. Chem.* 75:1569-1581, American Chemical Society, United States (2010).

Shan, Y., et al., "Reciprocal Effects of Micro-RNA-122 on Expression of Heme Oxygenase-1 and Hepatitis C Virus Genes in Human Hepatocytes," *Gastroenterology* 133:1166-1174, W.B. Saunders, United States (2007).

Shan, Y., et al., "Reciprocal Effects of Micro-RNA-122 on Expression of Heme Oxygenase-1 and Hepatitis C Virus Genes in Human Hepatocytes," Hepatology 80A. AASLD abstract #181. Wiley, United States (2006).

Shan, Y., et al., "An Antagomir of Mir-122 Down-Regulates Hepatitis C Virus Infection and Up-Regulates Heme Oxygenase-1 Expression in Human Hepatocytes", Gastroenterology 132:.A824, W.B. Saunders, Unites States (2007).

Singh, S. and Wengel, J., "Synthesis of Novel Bicyclo[2.2.1] Ribonucleosides: 2'-Amino- and 2'-Thio-LNA Monomeric Nucleosides," *J. Org. Chem.* 63:6078-6079, American Chemical Society, United States (1998).

Soifer, H., et al, "MicroRNAs in Disease and Potential Therapeutic Applications," *Mol. Ther.* 15:2070-2079, The American Society of Gene Therapy, United States (2007).

Sokol, N. and Ambros,V., "Mesodermally expressed*Drosophila microRNA-1* is regulated by Twist and is required in muscles during larval growth," *Gene Dev.* 19:2343-2354, (2005).

Sørensen, M., et al.,"α-L-*ribo*-Configured Locked Nucleic Acid (α-L-LNA): Synthesis and Properties," *J. Am. Chem. Soc. 124*:2164-2176, American Chemical Society, United States (2002).
Song, J.J. et al., "Crystal Structure of Argonaute and Its Implications for RISC Slicer Activity", Science 305, 1434-1437, American Assn. for the Advancement of Science, United States (2004).
Stark, A., et al., "Identification of *Drosophila* MicroRNA Targets," *PLoS Biology 1*:397-409, Academic Press, United States (2003).
Stein, C.A., "How to Design an Antisense Oligodeoxynucleotide Experiment: A Consensus Approach", Antisense Nucleic Acid Drug Dev. 8:129-132, Mary Ann Liebert Inc., United States (1998).
Stenvang, J. and Kauppinen, S., "MicroRNAs as targets for antisense-based therapeutics," *Expert. Opin. Biol Ther*. 8(1):59-81, Informa Healthcare, United Kingdom (2008).
Stenvang J. et al., "Targeting of microRNAs for therapeutics", Biochem. Soc. Trans. 36: 1197-1200, Portland Press on the Behalf of the Biochemical Society, United Kingdom (2008).
Swayze, E.E., et al. "Antisense oligonucleotides containing locked nucleic acid improve potency but cause significant hepatotoxicity in animals," Nucleic Acids Res. 35:687-700, Oxford University Press, United Kingdom (2007).
Tallet-Lopez, B., et al., "Antisense oligonucleotides targeted to the domain IIId of the hepatitis C virus IRES compete with 40S ribosomal subunit binding and prevent in vitro translation," Nucleic Acids Res. 31:734-742, Oxford University Press, United Kingdom (2003).
Tam, W., "Identification and characterization of human *BIC*, a gene on chromosome 21 that encodes a noncoding RNA," *Gene 274*:157-167, Elsevier, The Netherlands (2001).
Tijsterman, M., et al., "RNA Helicase MUT-14-Depedent Gene Silencing Triggered in *C. elegans* by Short Antisense RNAs," *Science 295*:694-697, American Assn. for the Advancement of Science, United States (2002).
Timmerman L., "Regulus, the microRNA child of Isis and Alnylam, strikes potential $150M deal with Glaxo." Xconomy on line publication, Feb. 25, 2010.
Triboulet, R., et al., "Suppression of MicroRNA-Silencing Pathway by HIV-1 During Virus Replication," *Science 315*:1579-1582, American Assn. for the Advancement of Science, United States (2007).
Tsai, W.-C., et al., "MicroRNA-122, a Tumor Suppressor MicroRNA that Regulates Intrahepatic Metastasis of Hepatocellular Carcinoma," *Hepatology* DOI:10.100/hep.22806, Wiley, United States (2009).
Tsuchiya, Y., et al., "MicroRNA Regulates the Expression of Human Cytochrome P450 1B1," *Cancer Res. 66*:9090-9098, American Association for Cancer Research, United States (2006).
Uhlmann, E., "Recent advances in the medicinal chemistry of antisense oligonucleotides," *Curr. Opin. Drug Discov. Develop.* 3:203-213, Pharma Press Ltd., United Kingdom (2000).
Uhlmann, E. and Peyman, A., "Antisense Oligonucleotides: A New Therapeutic Principle", Chemical Reviews 90: 543-584, American Chemical Society, United States (1990).
Válóczi, A., et al., "Sensitive and specific detection of microRNAs by northern blot analysis using LNA-modified oligonucleotide probes," *Nucleic Acids Res. 32*:e175, Oxford University Press, United Kingdom (2004).
van Rooij, E., et al., "Control of Stress-Dependent Cardiac Growth and Gene Expression by a MicroRNA," *Science 316*:575-579, American Assn. for the Advancement of Science, United States (2007).
van Rooij, E. and Olson, E., "MicroRNAs: powerful new regulators of heart disease and provocative therapeutic targets," *J. Clinic. Invest.* 117:2369-2376, American Society for Clinical Investigation, Unites States (2007).
Wagner, R., "Gene inhibitition using antisense oligodeoxyncleotides," *Nature 372*:333-335, Nature Publishing Group, United Kingdom (1994).
Wagner, R., et al.,"Potent and selective inhibition of gene expression by an antisense heptanucleotide," *Nat. Biotechnol. 14*:840-844, Nature Publishing Group, United Kingdom (1996).

Wahlestedt, C., et al., "Potent and nontoxic antisense oligonucleotides containing locked nucleic acids," *Proc. Natl. Acad. Sci. USA 97*:5633-5638, National Academy of the Sciences, United States (2000).
Wakita T. et al., "Production of infectious hepatitis C virus in tissue culture from a cloned viral genome", Nat. Med. 11(7): 791-796, nature Publishing Company, United States (2005).
Wakita T. et al., and Pietschmann T. et al., Abstracts O-33 & O-34, 11th International Symposium on HCV & Related Viruses, Heidelberg, Oct. 3-7, 2004.
Walter, T., et al., "Rejection Under Alpha Interferon Therapy in Liver Transplant Recipients," *American Journal of Transplantation 7*:177-184, Blackwell Munksgaard, Denmark (2007).
Wang, X., et al., "MicroRNA-122a functions as a novel tumor supressor downstream of adenomatous polyposis coli in gastrointestinal cancers," *Biochem. Biophys. Res. Comm.* 387: 376-380, Academic Press, United States (2009).
Wang, Z. et al., "miRNAs at the heart of the matter," *J. Mol. Med.* DOI:10.1007/s00109-008-0341-3, Springer International, Germany (2008).
Watanabe, T.A. et al., "Plasma Protein Binding of an Antisense Oligonucleotide Targeting Human ICAM-I (ISIS 2302)", Oligonucleotides 16:169-180, Mary Ann Liebert, Inc., United States (2006).
Wehner, K.A. & Sarnow, P., "Regulation of mRNA moelcules by microRANs," Translational Control in Biology & Medicine, Cold Spring Harbor Monograph Series 48: 297-318, Cold Spring Harbor Laboratory Press, United States (2007).
Weiler, J., et al., "Anti-miRNA oligonucleotides (AMOs) ammunition to target miRNAs implicated in human disease?" *Gene Ther. 13*:496-502, Nature Publishing Group, United Kingdom (2006).
Wengel J., "LNA (Locked Nucleic Acid)", in Antisense Drug Technology, Principles,Strategies and Applications, Ed. Crooke S.T. p. 339-357 (2001).
Wengel, J., et aL, "Chemistry of locked nucleic acids (LNA): Design, synthesis, and bio-physical properties," Letters in Peptide Science, 10:237-253, Kluwer Academic Publishers, Germany (2004).
Wienholds, E., et al., "MicroRNA Expression in Zebrafish Embryonic Development," *Science 309*:310-311, American Assn. for the Advancement of Science, United States (2005).
Worm, J., et al., "Silencing of microRNA-155 in mice during acute inflammatory response leads to derepression of c/ebp Beta and downregulation of G-CSF," Nucleic Oxford University Press, United Kingdom (2009).
Wu, X., et al, "miR-122 affects the viability anf apoptosis of hepatocellular carcinoma cells," *Scand. J. Gastroenter*. 44;1332-1339, Informa Healthcare, United Kingdom (2009).
Xiao, J. et al., "Novel Approaches for Gene-Specific Interface Via Manipulating Actions of MicroRNAs: Examination on the Pacemaker Channel Genes HCN2 and HCN4", J. Cell. Physiol. 212: 285-292, Wiley-Liss, New York, United States (2007).
Xie, Z-C. et al., "Transmission of Hepatitis C Virus Infection to Tree Shrews", Virology 244: 513-520, Academic Press, New York, United States (1998).
Yang, B., et al., "The muscle-specific microRNA *miR-1* regulates cardiac arrhythmogenic potential by targeting *GJA1* and *KCNJ2*," *Nat. Med. 13*:486-491, Nature Publishing Company, United States (2007).
Yekta, S., et al., "MicroRNA-Directed Cleavage of *HOXB8* MRNA," *Science 304*:594-596, American Assn. for the Advancement of Science, Unites States (2004).
Yi, M.K. and Lemon, S. M., "Adaptive Mutations Producing Efficient Replication of Genotype 1a Hepatitis C Virus RNA in Normal Huh7 Cells", J Virol. 78: 7904-7915, American Society for Microbiology (2004).
Yi-Ping, L. et al., "MicroRNA-122 antagonism against hepatitis C virusgenotypes 1-6 and reduced efficacy by host RNA insertion or mutations in the HCV 5' UTR", PNAS early edition, www.pnas.org/cgi/doi/10.1073/pnas 1016606108, National Academy of Sciences, United States (2011).
Yu, J., et of "RNA interference by expression of short-interfering RNAs and hairpin RNAs in mammalian cells," *Proc. Natl. Acad. Sci.* 99:6047-6052, National Academy of Sciences, United States (2002).

Zamecnik, P. C. and Stephenson M. N., "Inhibition of Rous sarcoma virus replication and cell transformation by a specific oligodeoxynucleotide", Proc. Natl. Acad. Sci. USA 75:280-284, National Academy of Sciences, United States (1978).

Zhang, H., et al., "Antisense Oligonucleotide Inhibition of Hepatisis C Virus (HCV) Gene Expression in Livers of Mice Infected with an HCV-Vaccinia Virus Recombinant," *Antimicrobial Agents and Chemotherapy* 43:347-353, American Society for Microbiology, United States (1999).

Zhao, Y. et al., "Serum response factor regulates a muscle-specific microRNA that targets *Hand2* during cardiogenesis," *Nature* 436:214-220, Nature Publishing Group, United Kingdom (2005).

Zhong, J. et al., "Robust hepatitis C virus infection in vitro", Proc. Natl. Acad. Sci. USA 102:9294-9299, National Academy of Sciences, United States (2005).

Baofeng Y., et al. P.R.C. patent application No. 200710072002. Extract from SIPO database, accessed in Jun. 6, 2007, 1 page.

Response and Amended Claims dated Sep. 17, 2007 in Office Action mailed on Mar. 16, 2007, U.S. Appl. No. 10/909,125, Esau et al., filed Jul. 30, 2004, 14 pages.

Response from Applicant dated May 13, 2008, in Office Action mailed Nov. 13, 2007 on U.S. Appl. No. 10/909,125, Esau et al., filed Jul. 30, 2004, 10 pages.

Response and Amended Claims dated Aug. 4, 2009 in reply to Office Action mailed Mar. 16, 2007 in U.S. Appl. No. 10/909,125, 12 pages.

Response to Office Action mailed Sep. 13, 2006 in U.S. Appl. No. 11/122,328, Sarnow et al., filed May 3, 2005, 11 pages.

International Search Report and Written Opinion for International Appl. No. PCT/DK2007/000169, European Patent Office, Netherlands, mailed on Mar. 7, 2008.

International Search Report for International Appl. No. PCT/EP2007/060703, European Patent Office, netherlands, mailed on Aug. 13, 2008.

International Search Report for International Appl. No. PCT/EP2008/053309, European Patent Office, Netherlands, mailed on Jul. 18. 2008.

International Search Report for International Appl. No. PCT/EP2008/066920, European Patent Office, Netherlands, mailed on Jun. 17, 2009.

Co-pending U.S. Appl. No. 13/057,147, filed Jul. 24, 2009, United States Patent Office, Alexandria, VA, United States (Not Published).

Co-pending U.S. Appl. No. 13/006,099, (continuation filed Jan. 13, 2011), United States Patent Office, Alexandria, VA., United States (now published as US 2012-0083596 A1).

Co-pending U.S. Appl. No. 13/057,147, filed Jul. 24, 2009, United States Patent Office, Alexandria, VA, United States (now published as US 2011-0146216 A1).

Co-pending U.S. Appl. No. 13/415,685, filed Mar. 8, 2012, United States Patent Office, Alexandria, VA, United States (Not Published).

Bartenschlager, R. and Lohmann, V., "Replication of hepatitis C virus," J. Gen. Virol. 81:1631-1648, Great Britain (2000).

Jannsen, H., et al., "A Randomized, Double-blind, Placebo (PLB) Controlled Safety and Anti-viral Proof of Concept Study of Miravirsen (MIR), an Oligonucleotide Targeting miR-122, in Treatment Naive Patients with Genotype 1 (GT1) Chronic HCV Infection," (Abstract) American Association for the Study of Liver Diseases (AASLD) 2011 Annual Meeting Abstract, Nov. 7, 2011, San Francisco, California, 1 page.

"Declaration of Dr. Susanna Obad," from File History of European Patent No. 1747023, dated Sep. 27, 2011, 4 pages.

"Declaration under 37 CFR 1.132 of Dr. Christine Esau," dated Apr. 15, 2011, from the File History of U.S. Appl. No. 11/513,102, filed Aug. 29, 2006, 5 pages.

"Exclusive License and Nonexclusive Option Agreement Between Glaxo Group Limited and Regulus Therapeutics Inc," Isis Pharmaceutics (Confidential), Exhibit 10.2, License Agreement, 56 pages, 2010.

McNair, T., "Cholesterol," BBC Health, accessed at: http://www.bbc.co.uk/health/physical_health/conditions/cholesterol1.shtml, accessed at Nov. 7, 2011, 3 pages.

"Opposition against European Patent No. 1 931 782 B1 granted to Isis Pharmaceuticals Inc.," Document No. G0119EP, Santaris Pharma A/S, Oct. 4, 2011, 46 pages.

Opposition Statement by Santaris Pharma A/S to EP-B-1747023, in the name of The Board of Trustees of the Leland Stanford Junior University, 94 pages, 2011.

Santairs Pharma A/S report new clinical data from miravirsen Phase 2a study to treat Hepatitis C in late-breaking oral presentation at the AASLD annual meeting, (Press Release) American Association for the Study of Liver Diseases (AASLD) 2011 Annual Meeting Abstract, Nov. 7, 2011, San Francisco, California, 2 pages.

Office Action mailed Aug. 25, 2011 in U.S. Appl. No. 12/245,544, inventor Obad, filed Oct. 3, 2008, 38 pages.

Office Action mailed on Aug. 3, 2011 in U.S. Appl. No. 12/295,960, inventors Elmén, et al., filed Mar. 30, 2009, 43 pages.

Office Action mailed on Nov. 22, 2011 in U.S. Appl. No. 12/400,625, inventors Kauppinen, et al., filed Mar. 9, 2009, 42 pages.

Office Action mailed on May 10, 2012 in U.S. Appl. No. 13/006,099, inventors Elmen et al., filed Jan. 13, 2011, 12 pages.

Office Action mailed on May 2, 2012 in U.S. Appl. No. 12/400,625, inventors inventors Kauppinen, et al., filed Mar. 9, 2009, 35 pages.

Office Action mailed on May 25, 2012 in U.S. Appl. No. 12/767,631, inventors Hildebrant-Eriksen, et al., filed Apr. 26, 2010, 19 pages.

Office Action mailed on Oct. 25, 2011 in U.S. Appl. No. 12/767,631, inventors Hildebrant-Eriksen, et al., filed Apr. 26, 2010, 15 pages.

Office Action mailed on Nov. 2, 2012, in U.S. Appl. No. 13/057,146, inventors Worm et al., filed Apr. 28, 2011, 7 pages.

Advisory Action mailed on Oct. 25, 2012, in U.S. Appl. No. 12/767,631, filed Apr. 26, 2010, 3 pages.

Office Action mailed on Sep. 20, 2012, in U.S. Appl. No. 13/006,099, inventors Elmen et al., filed Jan. 13, 2011, 12 pages.

* cited by examiner

PHARMACEUTICAL COMPOSITIONS FOR TREATMENT OF MICRORNA RELATED DISEASES

RELATED APPLICATIONS

This application is the National Stage of International Application No. PCT/EP2009/052728, filed Mar. 9, 2009, which claims the benefit of U.S. Provisional Application No. 61/034,745, filed Mar. 7, 2008, both of which are incorporated herein by reference in their entireties.

REFERENCE TO SEQUENCE LISTING SUBMITTED ELECTRONICALLY VIA EFS-WEB

The content of the electronically submitted sequence listing (Name: 2763_0190002_sequence_listing_ascii.txt; Size: 59,051 bytes; and Date of Creation: Apr. 24, 2012) filed with the application is incorporated herein by reference in its entirety.

FIELD OF THE INVENTION

The present invention provides compositions and methods of treatment of diseases that are sensitive to drugs that down-regulate the function of microRNA's, short non-coding RNA's, mRNA's, or viral genomes. In particular, the invention relates to compositions comprising oligonucleotides that modify the activity of microRNA's, short non-coding RNA's, mRNA', or viral genomes, wherein the compositions are made for administration with a long time interval when administered to a primate. The present invention further relates to methods of treatment wherein the compositions of the invention are provided to a primate, preferably a human, and wherein the compositions are administered with a long time interval.

BACKGROUND OF THE INVENTION microRNAs (miRNAs) are small regulatory RNAs that play important roles in development and disease[1-3] and, thus, represent a potential new class of targets for therapeutic intervention[4]. Despite recent progress in silencing of miRNAs in rodents[5,6], the development of effective and safe approaches for sequence-specific antagonism of microRNAs in vivo remains a significant scientific and therapeutic challenge. Moreover, there are no reports of miRNA antagonism in primates. Here we show that simple systemic delivery of an unconjugated, saline-formulated Locked Nucleic Acid-modified oligonucleotide (LNA-antimiR) effectively antagonizes the liver-expressed microRNA-122 in non-human primates. Acute administration by intravenous injections of 3 or 10 mg/kg LNA-antimiR to African green monkeys resulted in uptake of the LNA-antimiR in the cytoplasm of primate hepatocytes and formation of stable heteroduplexes between the LNA-antimiR and miR-122. This was accompanied by depletion of mature miR-122 and dose-dependent lowering of plasma cholesterol. Efficient silencing of miR-122 was achieved in primates by three doses of 10 mg/kg LNA-antimiR leading to long-lasting and reversible reduction of total plasma cholesterol without any evidence for LNA-associated toxicities or histopathological changes in the study animals. Our findings demonstrate the utility of systemically administered LNA-antimiRs in exploring microRNA function in rodents and primates and support the potential of such compounds as a novel class of therapeutics for disease-associated microRNAs. Further, the findings shows that pharmaceutical compositions comprising anti microRNA oligonucleotides of the invention, may be made and wherein the composition is made for administration to primates, and wherein the administration of maintenance dosis of the treatment can be made with a long time interval between each administration. Methods of treating diseases sensitive to treatment with anti microRNA oligonucleotides, using the compositions according to the invention are also provided.

SUMMARY OF THE INVENTION

The invention relates to methods of treatment and compositions for such treatment of diseases wherein modulation of the activity of a microRNA, short non-coding RNA, mRNA, or viral genome is beneficial. In particular, the invention relates to such methods and compositions wherein a modulator of the activity of a microRNA, short non-coding RNA, mRNA, or viral genome is administered to a primate, such as in example a human, and wherein the administration of maintenance dosages occur with a long time interval between each dosing. In a preferred embodiment, the modulator of the activity of a microRNA, short non-coding RNA, mRNA, or viral genome comprises an oligonucleotide. In a preferred embodiment, the compound is an antisense oligonucleotide which is not cleaved by RNase H. The invention is based on studies in primates using antisense oligonucleotides that inhibit the activity of microRNA-122, where a very long effect is seen on both blood cholesterol levels and on Hepatitis C virus titres.

FIGURE LEGENDS

FIG. 1. Silencing of miR-122 function in normal and hypercholesterolaemic mice by LNA-antimiR. a, Northern blot of liver RNA from mice treated with LNA-antimiR with a complete phosphorothioate backbone (PS), a mixed phosphorothioate/phosphodiester backbone (PS/PO) or an unmodified phosphodiester (PO) backbone. The Northern blot was probed for LNA-antimiR and re-probed for miR-122. b, Derepression of the direct miR-122 target aldolase A (same samples as in (a), normalized to GAPDH, mean and SEM, n=5). c, Total plasma cholesterol in mice after treatment with single i.p. doses of LNA-antimiR ranging from 1 to 200 mg/kg (mean and SEM, n=5, 1 mg/kg n=4). d, Total plasma cholesterol levels in hypercholesterolemic mice treated with saline, LNA-antimiR or LNA mismatch control, respectively, at a dose of 5 mg/kg i.p. twice weekly over a six-week period (mean and SEM, n=10, saline n=9). e, miR-122 Northern blot (same mice as in (d)). f, Quantification of aldolase A mRNA (same samples as (e), mean and SEM, n=10, saline n=9). g, Unsupervised clustering of liver mRNA expression profiles (same mice as in (d)). h, Expression changes of liver mRNAs in LNA-antimiR treated mice relative to controls. mRNAs are grouped by the presence/absence of different types of canonical miR-122 seed matches in the 3' UTR. Separation from mRNAs without seed matches is shown (inset) and was significant for all types of sites (p-values of $1.4\ 10^{-6}$, $2.2*10^{-13}$, $<10^{*-15}$ and $2.4*10^{-14}$ (KS-test) for 6 mer, 7mer-1A, 7mer-m8 and 8mer sites respectively).

Figure 2:
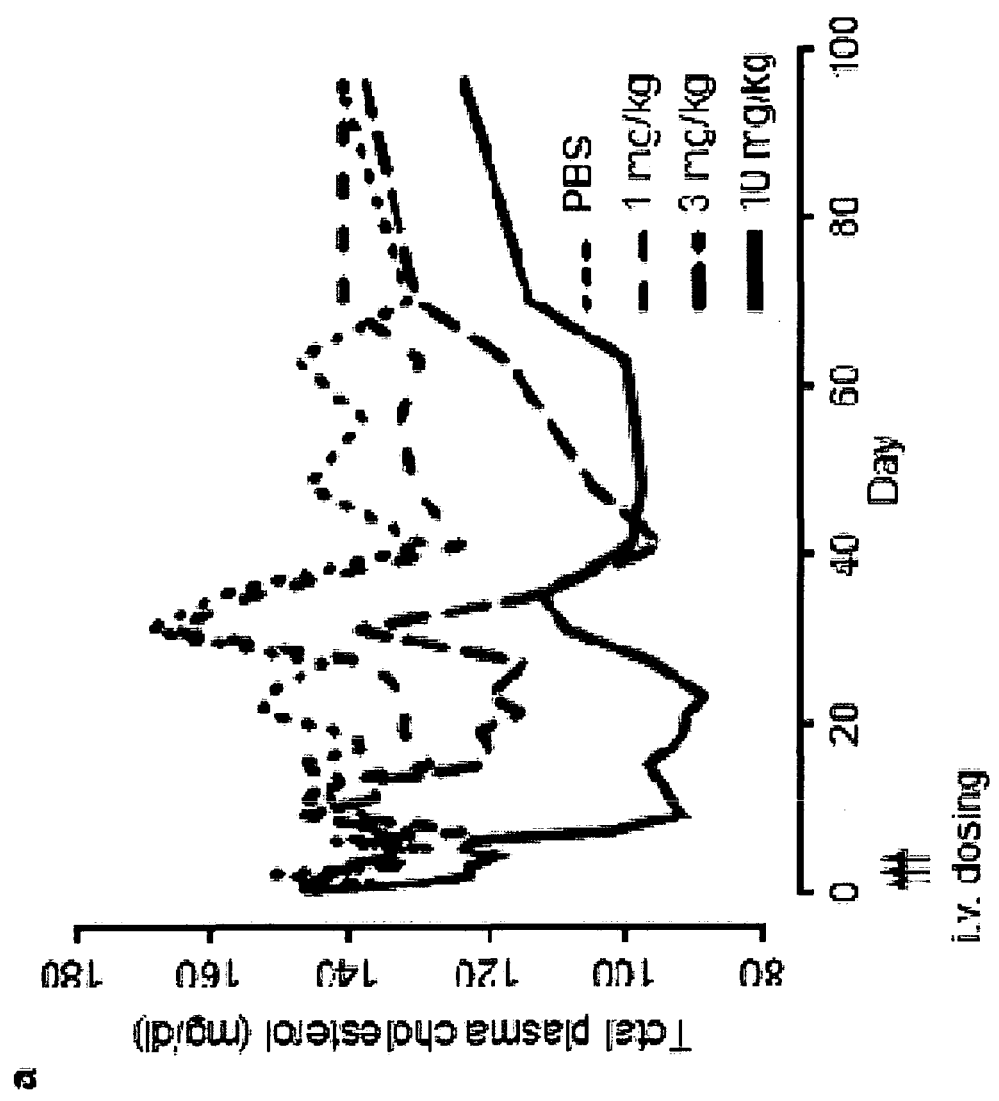
Figure 2:
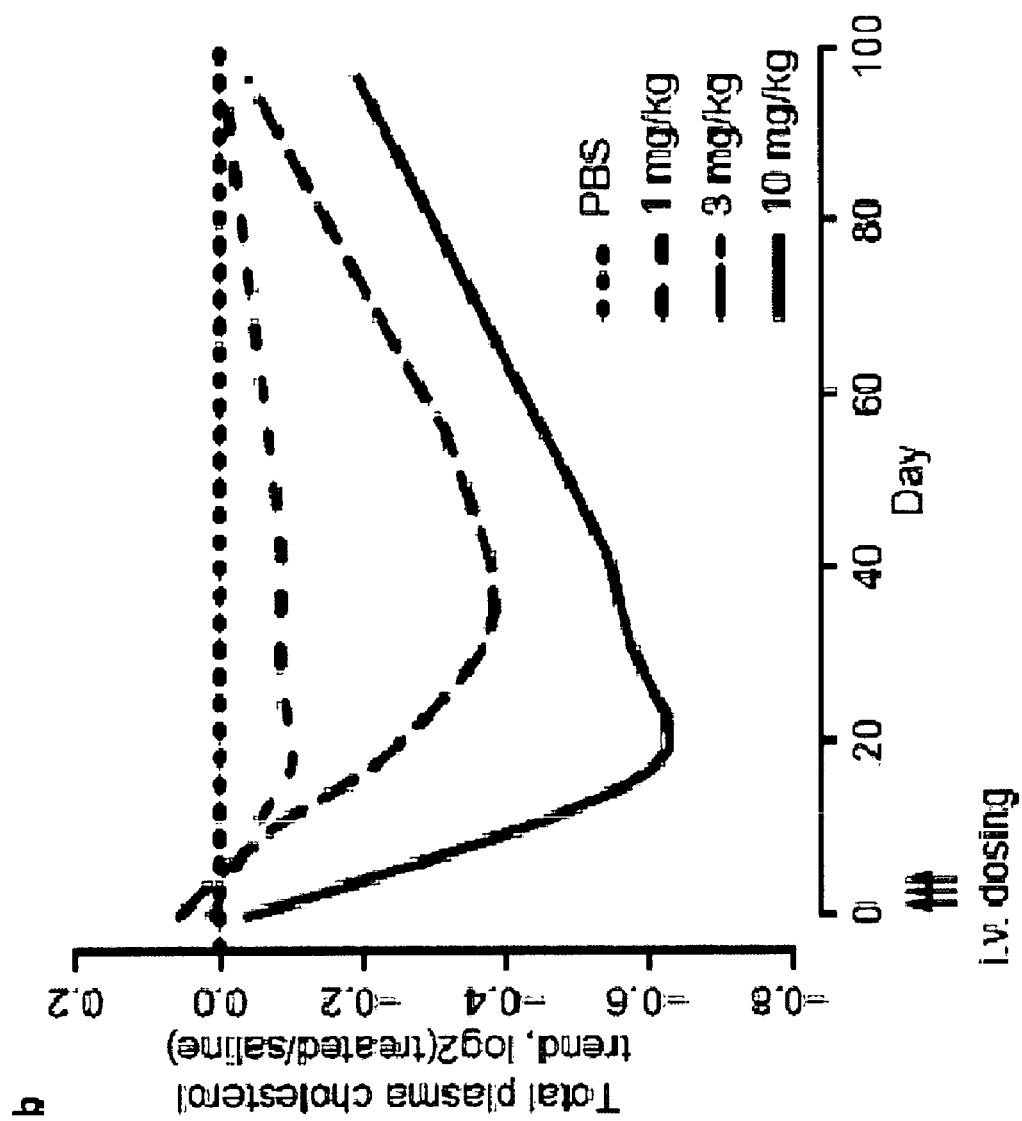
Figure 2:
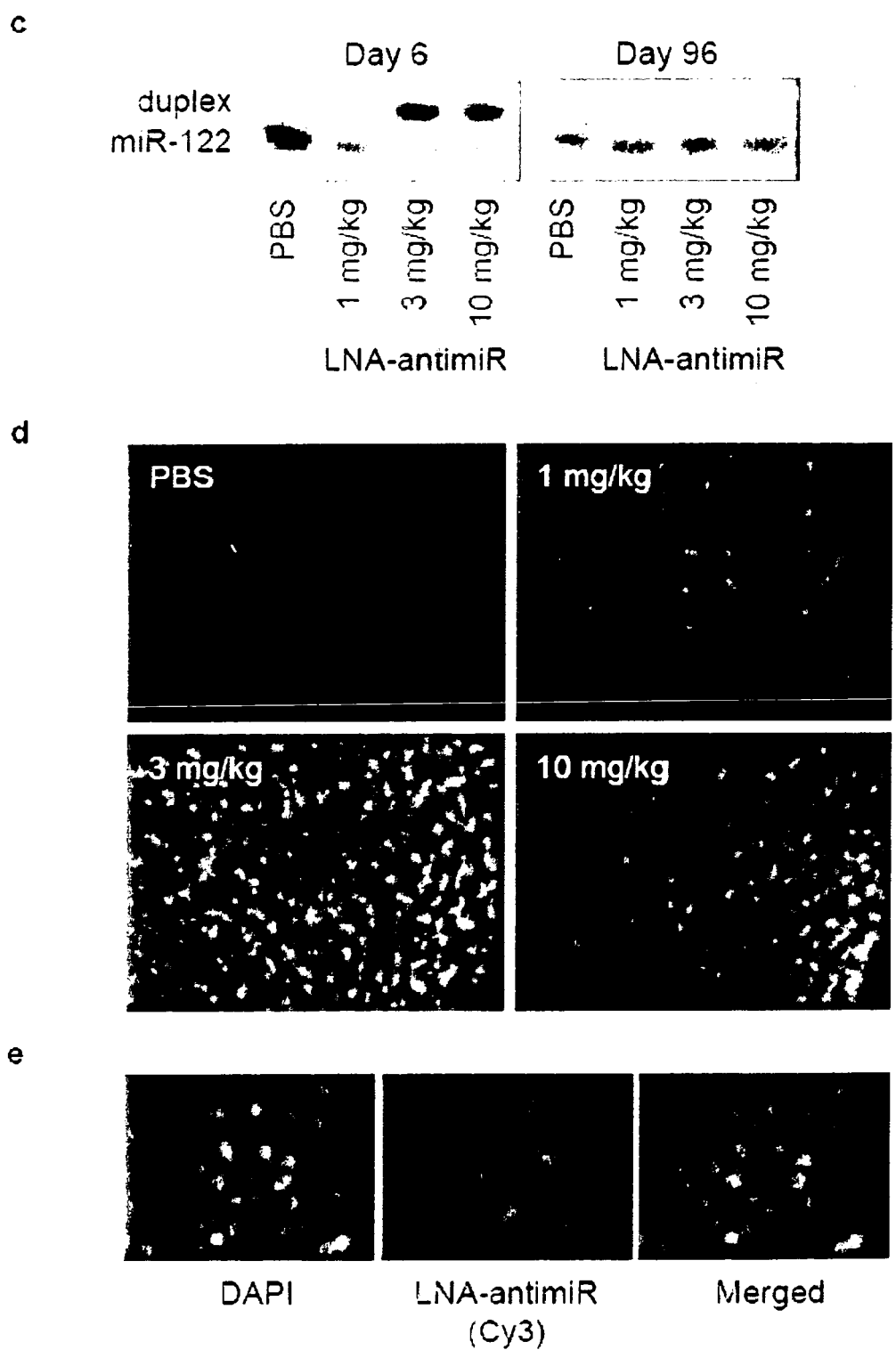

FIG. 2. Silencing of miR-122 in non-human primates by LNA-antimiR. a, total plasma cholesterol levels in African green monkeys treated with LNA-antimiR or saline by three i.v injections over five days (arrows) (n=5 per group). b, Trend plots of the cholesterol data in (a) normalized to the saline control group, Lowess-smoothened and log2-transformed. c, Northern blot analysis of monkey liver RNA samples from liver biopsies performed on day 6 and 96. d, In situ detection of LNA-antimiR in day 6 liver biopsies (same animals as in (c)). e, Cytoplasmic localization of LNA-antimiR in hepatocytes (day 6, 10 mg/kg).

Figure 3:
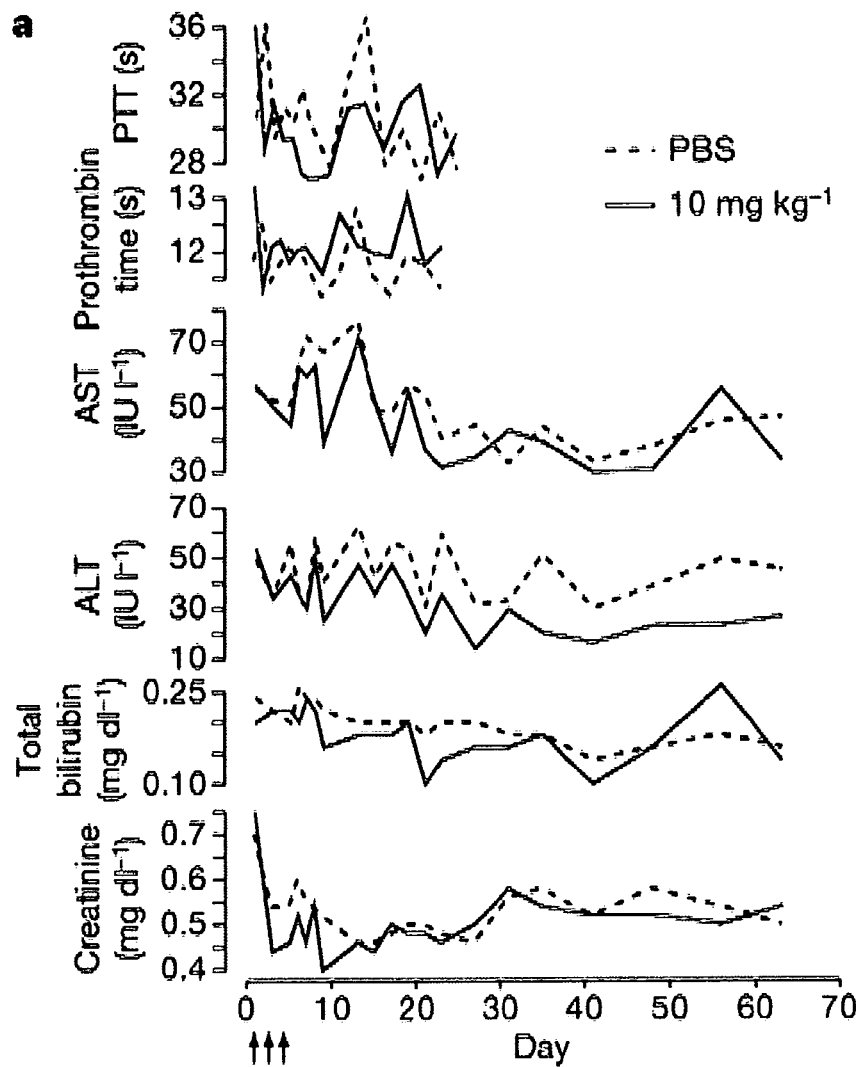
Figure 3:
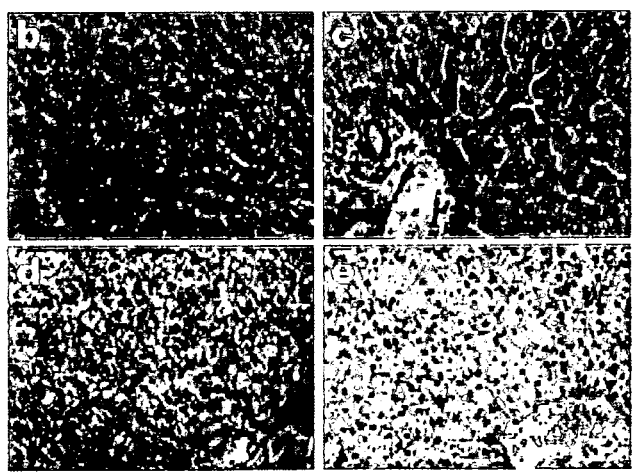

FIG. 3. LNA-mediated miR-122 silencing is safe in non-human primates. a, Prothrombin time, partial thromboplastin time (PTT), alanine aminotransferase (ALT), aspartate aminotransferase (AST), total bilirubin and creatinine levels assessed in African green monkeys after treatment with saline or 3×10 mg/kg LNA-antimiR. b, Photomicrographs of hematoxylin and eosin stained sections from day 6 liver biopsies.

Figure 4:
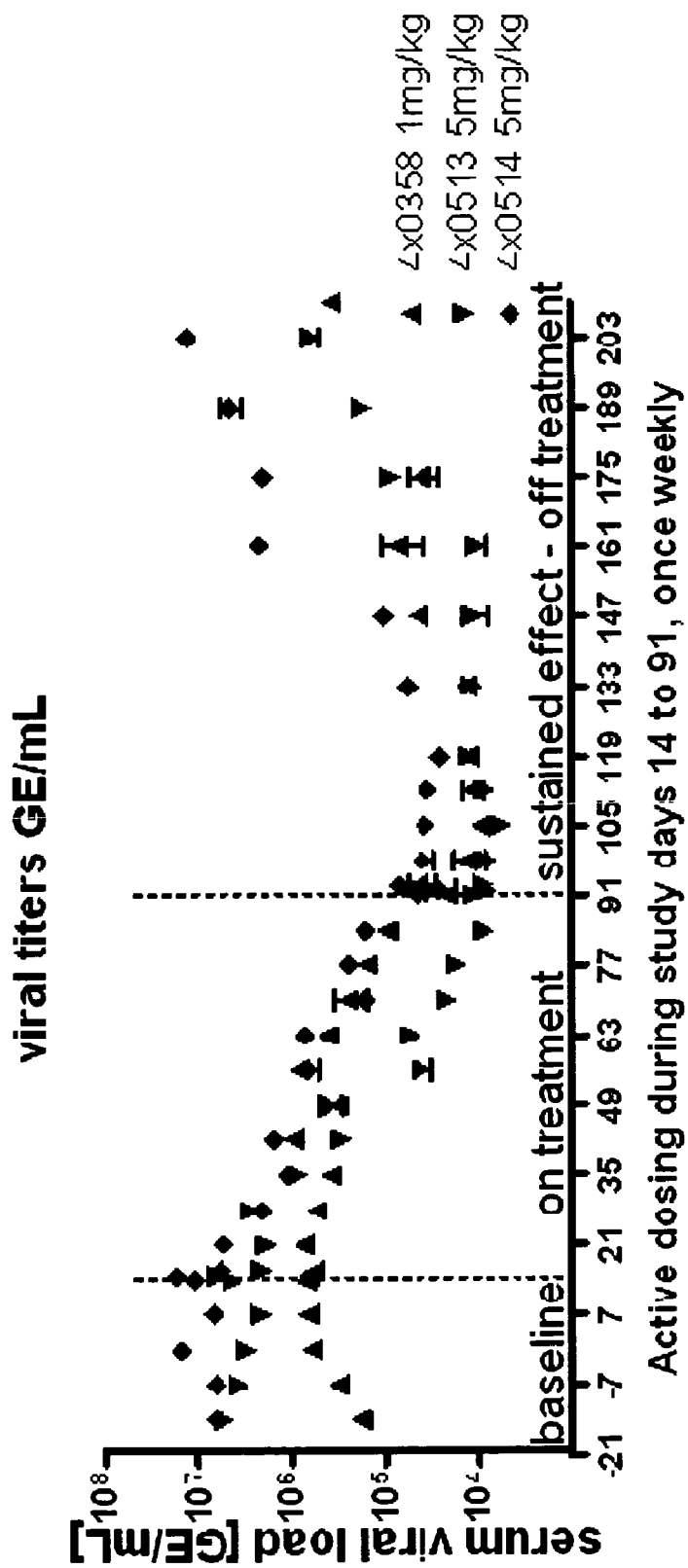

FIG. 4. AntimiR-122 mediated down-regulation of virus titres in HCV infected Chimpanzees. Chimpanzee 4x0358, a low dose animal, did not exhibit significant declines in viral titre until day 70 when the level of viremia began to decline and remained below baseline until day 175, 12 weeks after last dose. The maximum reduction in viral titre occurred on d105 with a decrease of 34-fold. Viremia returned to 1.8-fold below baseline value by the end of the study period, day 210.

Chimpanzee 4x0513, a high dose animal, began to decline in viral titre after day 28. This animal exhibited a consistent decrease in viremia with maximum decrease occurring on day 98 with a 395-fold reduction in viremia. Viremia remained below baseline only slowly increasing to within 7.7-fold of baseline by the end of the study.

Chimpanzee 4x0514, a high dose animal, exhibited a profile similar to 4x0513. A consistent decrease in viremia began at day 28 and continued with a maximum decrease occurring on day 92 with a 317-fold reduction in viremia. As with 4x0513, viremia then remained low, slowly increasing to baseline values by the end of the study.

DETAILED DESCRIPTION OF THE INVENTION

The present invention relates to compositions comprising an antisense oligomer targeting a RNA target in a cell or an organism (a subject, such as a primate), such as a RNA target selected from the group consisting of a microRNA, a mRNA, a non-coding RNA or a viral RNA, wherein the composition is made for maintaining treatment by administration with a large time interval in between each administration (i.e. dosage, such as an effective dose). The administration regimen comprises at least two successive administrations of the oligomer or the composition to a subject, wherein the dosage interval between the at least two successive administrations is at least 2 weeks and optionally is no greater than 20 weeks. In some embodiments, the composition is in a unit dose form, such as each unit dose forming the whole or part of a single administration to the subject.

The invention therefore, in some embodiments, provides a method of lowering of the activity of a RNA target in vivo in a primate, wherein said method comprises the administration of at least two dosages of an antisense oligonucleotide to said RNA target, wherein said antisense oligonucleotide is essentially incapable of recruiting RNAseH, and wherein at least two dosages are administered to the primate with a time interval between each administration of at least two weeks.

The invention therefore provides, in some embodiments, a method of lowering of the activity of a RNA target in vivo in a primate, wherein said method comprises the administration of at least two dosages of an antisense oligonucleotide to said RNA target, wherein said antisense oligonucleotide is a totalmer or a mixmer, and wherein at least two dosages are administered to the primate with a time interval between each administration of at least two weeks.

In some aspects, the at least two administrations are maintenance dosages of the antisense oligomer, such as a dosage which is sufficient to maintain an effective concentration of the oligomer in the subject, such as in a target tissue.

The number of administrations may be more than 2, such as 3, 4, 5, 6, 7, 8, 9, 10, 11, 12, 13, 14, 15, 16 or more treatments. As described herein, the actual number of administrations will depend on the nature of disease or disorder, for example. Diseases which may be cured will provide a definite end point to the administration regimen, whereas a disease or disorder may be treated over an extended period of time, effectively controlling symptoms, but may, in some embodiments not provide a cure. In such instances routine/regular administration may be continued for several months or years, until treatment is no longer desirable as determined by the medical practitioner. It will be noted that in some embodiments, administration regimens may be interrupted by a treatment pause, such a period of more than 125 days, or in some embodiments, a period of more than 2, 3, 5, or 6 months.

Further, in some embodiments, the invention relates to compositions comprising antisense oligomers that are essentially incapable of recruiting RNAseH, such as totalmers or mixmers, and wherein the compositions are made for maintaining a treatment of a patient, and wherein the dosages, such as the maintenance dosages, are provided with a long time interval in between each dosing.

The invention, in some aspects, provides for the use of an anti microRNA oligonucleotide in the preparation of a medicament for treating a disease or disorder in a primate, wherein the disease or disorder is characterized by being sensitive to downregulation of a micro RNA, The invention, in some aspects, provides for the use of an anti microRNA oligonucleotide in the preparation of a medicament for lowering of the activity of a particular micro RNA in a primate, such as, but not limited to a disease selected from the list of cardiac arythmia, cardiac hypertrophy, cancer, hypercholesterolemia, metabolic disorders, psoriasis, diabetes, auto immune disorders, hemochromatosis, or hepatitis C infection.

Furthermore, the invention, in some embodiments, relates to methods of treatment using the oligomers as described herein, such as totalmers or mixmers and compositions containing such oligomers wherein said method of treatment comprises at least two independent administrations of said oligomer or composition, wherein the dosage interval between at least two successive administrations of the oligomer or the composition to a subject, wherein the dosage interval is at least 2 weeks and optionally is no greater than 20 weeks. The compositions and methods are typically for use in primates, such as in humans. The subject may therefore be a primate, such as a human and may be a patient in need of said treatment.

(miRNAs) are ~22 nt endogenous non-coding RNAs that post-transcriptionally repress expression of protein-coding genes by base-pairing with the 3'-untranslated regions of the target mRNAs[1,2,7]. Emerging evidence suggests that animal miRNAs play important roles in the control of many biological processes[1-3,8]. In addition, miRNAs have been implicated in viral infections, cardiovascular disease, and neurological and muscular disorders, as well as in the onset and progression of cancers[9-19]. MicroRNA-122 is a liver-expressed miRNA implicated in cholesterol and lipid metabolism[5,6], and in hepatitis C virus (HCV) replication[14,20], underscoring miR-122 as a potential therapeutic target for treatment of hypercholesterolemia and hepatitis C infection. Examples of known correlations between specific microRNA's and diseases are listed in Table 1.

Taken together, our results demonstrate potent antagonism of a microRNA, in the particular case presented here of miR- 122 by simple systemic delivery of an unconjugated high-affinity LNA-antimiR oligonucleotide in mice and non-human primates. The therapeutic value of antagonizing miR-122 was inferred in two species where treatment of hypercholesterolemic mice with two weekly injections of 5 mg/kg LNA-antimiR and treatment of African green monkeys with three i.v. injections of 3 or 10 mg/kg LNA-antimiR resulted in effective and a very long-lasting reduction of plasma cholesterol without any evidence for LNA-associated toxicities. Furthermore, we have successfully shown that inhibiting miR-122 leads to long lasting down-regulation of Hepatitis C virus levels in chimpanzees. It is clear from our results that these long lasting effects are not disease related, but rather related to the modulation of microRNA activity, as seen in the miR-122 case with long lasting effects on both cholesterol levels and on Hepatitis C levels. The effects seen when targeting a microRNA seems not to be related to the use of LNA oligomers, since the length of the effect on mRNA regulation by an LNA oligomer usually is only about one third of that seen in the present experiments. Further, our results demonstrate a long effect of antisense oligonucleotides that are non-cleavable by RNase H when administered to primates.

In some embodiments, the oligonucleotide is an antisense oligomer targeting a microRNA, a mRNA, a non-coding RNA or a virus genome.

In one preferred embodiment, the oligonucleotide is designed as a mixmer that is essentially incapable of recruiting RNaseH. Oligonucleotides that are essentially incapable of recruiting RNaseH are well known in the literature, in example see WO2007/112754, WO2007/112753, or PCT/DK2008/000344. Mixmers may be designed to comprise a mixture of affinity enhancing nucleotide analogues, such as in non-limiting example 2'-O-alkyl-RNA monomers, 2'-amino-DNA monomers, 2'-fluoro-DNA monomers, LNA monomers, arabino nucleic acid (ANA) mononmers, 2'-fluoro-ANA monomers, HNA monomers, INA monomers, 2'-MOE-RNA (2'-O-methoxyethyl-RNA), 2'Fluoro-DNA, and LNA. In a further embodiment, the oligonucleotide does not include any DNA or RNA nucleotides, but is solely composed of affinity enhancing nucleotide analogues, such a molecule is may also be termed a totalmer. In some embodiments, the mixmer only comprise one type of affinity enhancing nucleotide analogues together with DNA and/or RNA. In some embodiments, the oligonucleotide is composed solely of one or more types of nucleotide analogues, such as in non-limiting example 2'-O-alkyl-RNA monomers, 2'-amino-DNA monomers, 2'-fluoro-DNA monomers, LNA monomers, arabino nucleic acid (ANA) mononmers, 2'-fluoro-ANA monomers, HNA monomers, INA monomers, 2'-MOE-RNA (2'-O-methoxyethyl-RNA), 2'Fluoro-DNA, and LNA.

Length

In some embodiments the antisense oligonucleotide has a length of 7-25 (contiguous) nucleotides, such as 8, 9, 10, 11, 12, 13, 14, 15, 16, 17, 18, 19, 20, 21, 22, 23, or 24 (contiguous) nucleotides. In some embodiments, the antisense oligonucleotide has a length of 7-10 (contiguous) nucleotide, or in some instances 7-16 nucleotides. In some embodiments, the antisense oligonucleotide at least 8 (contiguous) nucleotides in length, between 10-17 or 10-16 or 10-15 (contiguous) nucleotides, such as between 12-15 (contiguous) nucleotides.

Oligomers Which are Essentially Incapable of Recruiting RNaseH

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

In one embodiment in some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

It should be recognised that oligonucleotides which are mixmers or totalmers are usually essentially incapable of recruiting RNAseH and as such where we use the term essentially incapable or recruiting RNaseH herein, in some embodiments, such a term may be replaced with the term mixmer or totalmer, as defined herein, even if, in some instances such oligomers actually do possess significant ability to recruit RNaseH, such as when using DNA mixmers with alpha-L-oxy-LNA.

In some embodiments, the oligomer or contiguous nucleotide sequence thereof consists of a contiguous sequence of nucleotide analogues, such as affinity enhancing nucleotide analogues—referred to herein is as a 'totalmer'.

Totalmers

A totalmer is a single stranded oligomer which only comprises non-naturally occurring nucleotides.

The oligomer maybe a totalmer—indeed various totalmer designs are highly effective as therapeutic oligomers, particularly when targeting microRNA (antimiRs) or as splice switching oligomers (SSOs).

In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-OMe RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 8 and 16 nucleotides, such as 9, 10, 11, 12, 13, 14, or 15 nucleotides, such as between 8 and 12 nucleotides.

In some embodiments, the contiguous nucleotide sequence of the totalmer comprises of at least 30%, such as at least 40%, such as at least 50%, such as at least 60%, such as at least 70%, such as at least 80%, such as at least 90%, such as 95%, such as 100% LNA units. The remaining units may be selected from the non-LNA nucleotide analgues referred to herein in, such those selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group 2'-OMe RNA unit and 2'-fluoro DNA unit.

In some embodiments the totalmer consist or comprises of a contiguous nucleotide sequence which consists only of LNA units.

In some embodiments, the totalmer may be targeted against a microRNA (i.e. be antimiRs)—as referred to in U.S. provisional applications 60/979,217 and 61/028,062, and PCT/DK2008/000344, all of which are hereby incorporated by reference.

Mixmers

The term 'mixmer' refers to oligomers which comprise both naturally and non-naturally occurring nucleotides, where, as opposed to gapmers, tailmers, headmers and blockmers, there is no contiguous sequence of more than 5 naturally occurring nucleotides, such as DNA units.

The oligomer according to the invention may be mixmers—indeed various mixmer designs are highly effective as therapeutic oligomers, particularly when targeting microRNA (antimiRs), microRNA binding sites on mRNAs (Blockmirs) or as splice switching oligomers (SSOs).

The oligomer may, in some embodiments, also be a mixmer and indeed, due to the ability of mixmers to effectively and specifically bind to their target, the use of mixmers as therapeutic oligomers are considered to be particularly effective in decreasing the target RNA.

In some embodiments, the mixmer comprises or consists of a contiguous nucleotide sequence of repeating pattern of nucleotide analogue and naturally occurring nucleotides, or one type of nucleotide analogue and a second type of nucleotide analogues. The repeating pattern, may, for instance be every second or every third nucleotide is a nucleotide analogue, such as LNA, and the remaining nucleotides are naturally occurring nucleotides, such as DNA, or are a 2' substituted nucleotide analogue such as 2'MOE of 2'fluoro analoguess as referred to herein, or, in some embodiments selected form the groups of nucleotide analogues referred to herein. It is recognised that the repeating pattern of nucleotide analogues, such as LNA units, may be combined with nucleotide analogues at fixed positions—e.g. at the 5' or 3' termini.

In some embodiments the first nucleotide of the oligomer, counting from the 3' end, is a nucleotide analogue, such as an LNA nucleotide.

In some embodiments, which maybe the same or different, the second nucleotide of the oligomer, counting from the 3' end, is a nucleotide analogue, such as an LNA nucleotide.

In some embodiments, which maybe the same or different, the seventh and/or eighth nucleotide of the oligomer, counting from the 3' end, are nucleotide analogues, such as LNA nucleotides.

In some embodiments, which maybe the same or different, the ninth and/or the tenth nucleotides of the oligomer, counting from the 3' end, are nucleotide analogues, such as LNA nucleotides.

In some embodiments, which maybe the same or different, the 5' terminal of the foligomer is a nucleotide analogue, such as an LNA nucleotide.

The above design features may, in some embodiments be incorporated into the mixmer design, such as antimiR mixmers.

In some embodiments, the mixmer does not comprise a region of more than 4 consecutive DNA nucleotide units or 3 consecutive DNA nucleotide units. In some embodiments, the mixmer does not comprise a region of more than 2 consecutive DNA nucleotide units.

In some embodiments, the mixmer comprises at least a region consisting of at least two consecutive nucleotide analogue units, such as at least two consecutive LNA units.

In some embodiments, the mixmer comprises at least a region consisting of at least three consecutive nucleotide analogue units, such as at least three consecutive LNA units.

In some embodiments, the mixmer of the invention does not comprise a region of more than 7 consecutive nucleotide analogue units, such as LNA units. In some embodiments, the mixmer of the invention does not comprise a region of more than 6 consecutive nucleotide analogue units, such as LNA units. In some embodiments, the mixmer of the invention does not comprise a region of more than 5 consecutive nucleotide analogue units, such as LNA units. In some embodiments, the mixmer of the invention does not comprise a region of more than 4 consecutive nucleotide analogue units, such as LNA units. In some embodiments, the mixmer of the invention does not comprise a region of more than 3 consecutive nucleotide analogue units, such as LNA units. In some embodiments, the mixmer of the invention does not comprise a region of more than 2 consecutive nucleotide analogue units, such as LNA units.

In the mixmer embodiments, which refer to the modification of nucleotides in positions 3 to 8, counting from the 3' end, the LNA units may be replaced with other nucleotide anlogues, such as those referred to herein. "X" may, therefore be selected from the group consisting of 2'-O-alkyl-RNA unit, 2'-OMe-RNA unit, 2'-amino-DNA unit, 2'-fluoro-DNA unit, 2'-MOE-RNA unit, LNA unit, PNA unit, HNA unit, INA unit. "x" is preferably DNA or RNA, most preferably DNA.

In some embodiments, the mixmer, such as an antimiR mixmer, is modified in positions 3 to 8 —i.e. comprises at least one nucleotide analogue in positions 3 to 8, counting from the 3' end. The design of this sequence may be defined by the number of non-LNA units present or by the number of LNA units present. In some embodiments of the former, at least one, such as one, of the nucleotides in positions three to eight, counting from the 3' end, is a non-LNA unit. In some embodiments, at least two, such as two, of the nucleotides in positions three to eight, counting from the 3' end, are non-LNA units. In some embodiments, at least three, such as three, of the nucleotides in positions three to eight, counting from the 3' end, are non-LNA units. In some embodiments, at least four, such as four, of the nucleotides in positions three to eight, counting from the 3' end, are non-LNA units. In some embodiments, at least five, such as five, of the nucleotides in positions three to eight, counting from the 3' end, are non-LNA units. In some embodiments, all six nucleotides in positions three to eight, counting from the 3' end, are non-LNA units.

Alternatively defined, in some embodiments, the mixmer, such as an antimiR mixmer, according to the invention comprises at least one LNA unit in positions three to eight, counting from the 3' end. some embodiments, the mixmer, such as an antimiR mixmer, comprises one LNA unit in positions three to eight, counting from the 3' end. The substitution pattern for the nucleotides in positions three to eight, counting from the 3' end, may be selected from the group consisting of Xxxxxx, xXxxxx, xxXxxx, xxxXxx, xxxxXx and xxxxxX, wherein "X" denotes an LNA unit and "x" denotes a non-LNA unit.

In some embodiments, the mixmer, such as an antimiR mixmer, comprises at least two LNA units in positions three to eight, counting from the 3' end. In some embodiments thereof, the mixmer comprises two LNA units in positions three to eight, counting from the 3' end. The substitution pattern for the nucleotides in positions three to eight, counting from the 3' end, may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes an LNA unit and "x" denotes a non-LNA unit. In an embodiment, the substitution pattern for the nucleotides in positions three to eight, counting from the 3' end, is selected from the group consisting of XxXxxx, XxxXxx, XxxxXx, XxxxxX, xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx and xxXxXx, wherein "X" denotes an LNA unit and "x" denotes a non-LNA unit. In some embodiments, the substitution pattern for the nucleotides in positions three to eight, counting from the 3' end, is xXxXxx, wherein "X" denotes an LNA unit and "x" denotes a non-LNA unit.

In some embodiments, the mixmer, such as an antimiR mixmer, comprises at least three LNA units in positions three to eight, counting from the 3' end. In an embodiment thereof, the mixmer comprises three LNA units in positions three to eight, counting from the 3' end. The substitution pattern for the nucleotides in positions three to eight, counting from the 3' end, may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In some embodiments, the substitution pattern for the nucleotides in positions three to eight, counting from the 3' end, is selected from the group consisting of XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In some embodiments, the substitution pattern for the nucleotides in positions three to eight, counting from the 3' end, is selected from the group consisting of xXXxXx, xXXxxX, xxXXxX, xXxXXx, xXxxXX, xxXxXX and xXxXxX, wherein "X" denotes an LNA unit and "x" denotes a non-LNA unit. In some embodiments, the substitution pattern for the nucleotides in positions three to eight, counting from the 3' end, is xXxXxX or XxXxXx, wherein "X" denotes an LNA unit and "x" denotes a non-LNA unit. In some embodiments, the substitution pattern for the nucleotides in positions three to eight, counting from the 3' end, is xXxXxX, wherein "X" denotes an LNA unit and "x" denotes a non-LNA unit.

In some embodiments, the mixmer comprises at least four LNA units in positions three to eight, counting from the 3' end. In some embodiments thereof, the mixmer comprises four LNA units in positions three to eight, counting from the 3' end. The substitution pattern for the nucleotides in positions three to eight, counting from the 3' end, may be selected from the group consisting of xxXXXX, xXxXXX, xXXxXX, xXXXxX, xXXXXx, XxxXXX, XxXxXX, XxXXxX, XxXXXx, XXxxXX, XXxXxX, XXxXXx, XXxxXx, XXXxxX, XXXxXx and XXXXxx, wherein "X" denotes an LNA unit and "x" denotes a non-LNA unit.

In some embodiments, the mixmer according to the present invention comprises at least five LNA units in positions three to eight, counting from the 3' end. In some embodiments thereof, the mixmer comprises five LNA units in positions three to eight, counting from the 3' end. The substitution pattern for the nucleotides in positions three to eight, counting from the 3' end, may be selected from the group consisting of xXXXXX, XxXXXX, XXxXXX, XXXxXX, XXXXxX and XXXXXx, wherein "X" denotes an LNA unit and "x" denotes a non-LNA unit.

In some embodiments, said non-LNA unit is another nucleotide analogue unit.

In some mixmer embodiments the substitution pattern for the nucleotides from position 11, counting from the 3' end, to the 5' end may include nucleotide analogue units (such as LNA) or it may not. In some embodiments, the mixmer comprises at least one nucleotide analogue unit (such as LNA), such as one nucleotide analogue unit, from position 11, counting from the 3' end, to the 5' end. In some embodiments, the mixmer comprises at least two nucleotide analogue units, such as LNA units, such as two nucleotide analogue units, from position 11, counting from the 3' end, to the 5' end.

In some embodiments which refer to the modification of nucleotides in the nucleotides from position 11 to the 5' end of the oligomer, the LNA units may be replaced with other nucleotide anlogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In some embodiments, the mixmer has the following substitution pattern, which is repeated from nucleotide eleven, counting from the 3' end, to the 5' end: xXxX or XxXx, wherein "X" denotes an LNA unit and "x" denotes a non-LNA unit. In another embodiment, the mixmer has the following substitution pattern, which is repeated from nucleotide eleven, counting from the 3' end, to the 5' end: XXxXxx, XXxxXx or XxXxxX, wherein "X" denotes an LNA unit and "x" denotes a non-LNA unit. In yet another embodiment, the mixmer has the following substitution pattern, which is repeated from nucleotide eleven, counting from the 3' end, to the 5' end: XXXxXXXx, XXxXxXxX, XXXxxxXX or XXxXxxXX, wherein "X" denotes an LNA unit and "x" denotes a non-LNA unit.

The specific substitution pattern for the nucleotides from position 11, counting from the 3' end, to the 5' end depends on the number of nucleotides in the mixmer. In a preferred embodiment, the mixmer contains 12 nucleotides and the substitution pattern for positions 11 to 12, counting from the 3' end, is selected from the group consisting of xX and Xx, wherein "X" denotes an LNA unit and "x" denotes a non-LNA unit. In some embodiments, the substitution pattern for positions 11 to 12, counting from the 3' end, is xX, wherein "X" denotes an LNA unit and "x" denotes a non-LNA unit. Alternatively, no LNA units are present in positions 11 to 12, counting from the 3' end, i.e. the substitution pattern is xx.

In some embodiments, the mixmer contains 12 nucleotides and the substitution pattern for positions 10 to 12, counting from the 3' end, is selected from the group consisting of Xxx, xXx, xxX, XXx, XxX, xXX and XXX, wherein "X" denotes an LNA unit and "x" denotes a non-LNA unit. In some embodiments thereof, the substitution pattern for positions 10 to 12, counting from the 3' end, is selected from the group consisting of xXx, xxX and xXX, wherein "X" denotes an LNA unit and "x" denotes a non-LNA unit. In some embodiments, the substitution pattern for positions 10 to 12, counting from the 3' end, is xxX, wherein "X" denotes an LNA unit and "x" denotes a non-LNA unit. Alternatively, no LNA units are present in positions 10 to 12, counting from the 3' end, i.e. the substitution pattern is xxx.

In some embodiments, the mixmer contains an LNA unit at the 5' end. In some embodiments, the mixmer contains an LNA unit at the first two positions, counting from the 5' end. The mixmer may also contain one or more of the structural features which are specified in the context of the antimiR herein—either the context that the mixmer contains a similar pattern and number of nucleotides/nucleotide analogues (e.g. X and x or X and Y).

TABLE 1

Examples of some diseases where specific microRNAs have been indicated.

| microRNA | Possible medical indications |
|---|---|
| miR-1 | Cardiac arythmia |
| Let-7 | Cancer |
| miR-21 | Glioblastoma, breast cancer, hepatocellular carcinoma, colorectal cancer, sensitization of gliomas to cytotoxic drugs, cardiac hypertrophy |
| miR-21, miR-200b and miR-141 | Response to chemotherapy and regulation of cholangiocarcinoma growth |
| miR-122 | hypercholesterolemia, hepatitis C infection, hemochromatosis |
| miR-19b | lymphoma and other tumour types |
| miR-26a | Osteoblast differentiation of human stem cells |
| miR-155 | lymphoma, pancreatic tumor development, breast and lung cancer |
| miR-203 | Psoriasis |
| miR-375 | diabetes, metabolic disorders, glucose-induced insulin secretion from pancreatic endocrine cells |
| miR-181 | myoblast differentiation, auto immune disorders |
| miR-10b | Breast cancer cell invasion and metastasis |
| miR-125b-1 | Breast, lung, ovarian and cervical cancer |
| miR-221 and 222 | Prostate carcinoma, human thyroid papillary car, human hepatocellular carcinoma |
| miRNA-372 and -373 | testicular germ cell tumors. |
| miR-142 | B-cell leukemia |
| miR-17-19b cluster miR-17-5p, miR-20a/b, miR-93, miR-106a/b, miR-18a/b, miR-19a/b, miR-25, miR-92a, miR-363. | B-cell lymphomas, lung cancer, hepatocellular carcinoma |

The oligomer may, in some embodiments, be either i) fully complementary to a sub-sequence of contiguous nucleotides present in the RNA target, or ii) comprises no more than a single mismatch with the complement of a sub-sequence of contiguous nucleotides present in said RNA target. As such the oligonucleotide is an antisense oligonucleoitde—in that it is either fully complementary to the (corresponding) target sequence, or comprises no more than a single mismatch with the target sequence. The RNA target is typically associated with a medical condition or disease, and may in some embodiments, be a microRNA or a mRNA, for example. The oligomer may therefore be, for example, an antimiR, a microRNA mimic, a microRNA blockmir, or an antisense oligomer.

The oligomer may therefore be an antimir which targets (i.e. comprises or consists of a contiguous nucleotide sequence which is fully complementary to (a corresponding region of) one of the microRNAs listed above or comprises of no more than a single mismatch thereto. Such oligonucleotides may be referred to as anti-microRNA oligonucleotides.

A particular microRNA may for example be any of the individual microRNAs disclosed to or referred to herein, including all microRNAs published in miRBase and the patent applications referred to here. The term particular in this context may refer to a microRNA.

Modulators of microRNA's Useful in the Invention

Specially preferred compounds for use in the present invention are those that target microRNA's. Sequences of known microRNA's can be found in the microRNA database "mirbase" (http://microrna.sanger.ac.uk/sequences/). Inhibitors of microRNA have been described in numerous patents and articles and are well known to the person skilled in the art. In a preferred embodiment, examples of such documents describing useful microRNA modulators are WO2007/112754, WO2007/112753, or PCT/DK2008/000344 all of which are hereby incorporated by reference. In another preferred embodiment, such microRNA modulators are those described in WO2009/20771, WO2008/91703, WO2008/046911, WO2008/074328, WO2007/90073, WO2007/27775, WO2007/27894, WO2007/21896, WO2006/93526, WO2006/112872, WO2005/23986, or WO2005/13901, all of which are hereby incorporated by reference.

In one preferred embodiment, the modulator comprises an antisense LNA oligonucleotide. In one specially preferred embodiment, the modulator comprises an oligonucleotide which is between 7 and 25 nucleotides long and comprises at least one LNA. In some embodiments, the microRNA modulator comprises an oligonucleotide which is between 7 and 25 nucleotides long and comprises at least one LNA, and further comprises at least one other affinity increasing nucleotide analogue. In some embodiments, the oligonucleotide of the invention comprise phosphorothioate linkages. In one specially preferred embodiment, the pharmaceutical composition comprise an anti-miR-122 oligomer having the sequence: 5'-CcAttGTcaCaCtCC-3' (Seq ID # 11), wherein Capital letters indicate LNA units.

In a preferred embodiment, the microRNA modulater is an LNA antisense oligomer comprising or consisting of any one of the sequences listed in Tables 2 and 3.

TABLE 2

The following specific compounds, which may be used in the methods of the present invention, such as in the treatment of a disease, such as a disease where expression/over-expression of one or more microRNAs are indicated such as those diseases illustrated in table 1. The compounds are preferably fully phosphorothioate and each nuceltode is a LNA nucleotide, such as beta-D-oxy LNA. LNA cytosine may be 5'methyl cytosine. The compounds are directed towards the seed regions of their target microRNA (i.e. are seedmers). The compounds are as disclosed in table 1 of PCT/DK2008/000344, which discloses antimiRs targeting the microRNAs as published in miRbase and which is specifically incorporated by reference to provide oligomers which may be used in the methods of the present invention. Equivalent antimiRs can be designed by matching the -2 to -8/-9 or -10 positions (for 7, 8 or 9mers) of mature microRNAs (counting from the terminal 5' nucleotide of the microRNA (i.e. at the -1 position)-such as against the micrRNAs indicated with cancer, as disclosed in WO2008/046911.

| microRNA | 9-mers | SEQ ID | 8-mers | SEQ ID | 7-mers | SEQ ID |
|---|---|---|---|---|---|---|
| hsa-miR-1 | TTACATTCC | 12 | TACATTCC | 62 | ACATTCC | 112 |
| hsa-miR-106a | AAGCACTTT | 13 | AGCACTTT | 63 | GCACTTT | 113 |
| hsa-miR-106a* | TACATTGCA | 14 | ACATTGCA | 64 | CATTGCA | 114 |

TABLE 2-continued

The following specific compounds, which may be used in the methods of the present invention, such as in the treatment of a disease, such as a disease where expression/over-expression of one or more microRNAs are indicated such as those diseases illustrated in table 1. The compounds are preferably fully phosphorothioate and each nuceltode is a LNA nucleotide, such as beta-D-oxy LNA. LNA cytosine may be 5'methyl cytosine. The compounds are directed towards the seed regions of their target microRNA (i.e. are seedmers). The compounds are as disclosed in table 1 of PCT/DK2008/000344, which discloses antimiRs targeting the microRNAs as published in miRbase and which is specifically incorporated by reference to provide oligomers which may be used in the methods of the present invention. Equivalent antimiRs can be designed by matching the -2 to -8/-9 or -10 positions (for 7, 8 or 9mers) of mature microRNAs (counting from the terminal 5' nucleotide of the microRNA (i.e. at the -1 position)-such as against the micrRNAs indicated with cancer, as disclosed in WO2008/046911.

| microRNA | 9-mers | SEQ ID | 8-mers | SEQ ID | 7-mers | SEQ ID |
|---|---|---|---|---|---|---|
| hsa-miR-106b | CAGCACTTT | 15 | AGCACTTT | 65 | GCACTTT | 115 |
| hsa-miR-106b* | CACAGTGCG | 16 | ACAGTGCG | 66 | CAGTGCG | 116 |
| hsa-miR-10b | CTACAGGGT | 17 | TACAGGGT | 67 | ACAGGGT | 117 |
| hsa-miR-122 | TCACACTCC | 18 | CACACTCC | 68 | ACACTCC | 118 |
| hsa-miR-125b | GTCTCAGGG | 19 | TCTCAGGG | 69 | CTCAGGG | 119 |
| hsa-miR-141 | GACAGTGTT | 20 | ACAGTGTT | 70 | CAGTGTT | 120 |
| hsa-miR-141* | CTGGAAGAT | 21 | TGGAAGAT | 71 | GGAAGAT | 121 |
| hsa-miR-142-3p | AAACACTAC | 22 | AACACTAC | 72 | ACACTAC | 122 |
| hsa-miR-142-5p | CTACTTTAT | 23 | TACTTTAT | 73 | ACTTTAT | 123 |
| hsa-miR-155 | TTAGCATTA | 24 | TAGCATTA | 74 | AGCATTA | 124 |
| hsa-miR-17 | AAGCACTTT | 25 | AGCACTTT | 75 | GCACTTT | 125 |
| hsa-miR-17* | TCACTGCAG | 26 | CACTGCAG | 76 | ACTGCAG | 126 |
| hsa-miR-181a | GTTGAATGT | 27 | TTGAATGT | 77 | TGAATGT | 127 |
| hsa-miR-181a* | GGTCGATGG | 28 | GTCGATGG | 78 | TCGATGG | 128 |
| hsa-miR-181a-2* | GGTCAGTGG | 29 | GTCAGTGG | 79 | TCAGTGG | 129 |
| hsa-miR-181b | AATGAATGT | 30 | ATGAATGT | 80 | TGAATGT | 130 |
| hsa-miR-181c | GTTGAATGT | 31 | TTGAATGT | 81 | TGAATGT | 131 |
| hsa-miR-181c* | GTCGATGGT | 32 | TCGATGGT | 82 | CGATGGT | 132 |
| hsa-miR-18a | ATGCACCTT | 33 | TGCACCTT | 83 | GCACCTT | 133 |
| hsa-miR-18a* | TTAGGGCAG | 34 | TAGGGCAG | 84 | AGGGCAG | 134 |
| hsa-miR-18b | ATGCACCTT | 35 | TGCACCTT | 85 | GCACCTT | 135 |
| hsa-miR-18b* | ATTTAGGGC | 36 | TTTAGGGC | 86 | TTAGGGC | 136 |
| hsa-miR-19a | GATTTGCAC | 37 | ATTTGCAC | 87 | TTTGCAC | 137 |
| hsa-miR-19a* | ATGCAAAAC | 38 | TGCAAAAC | 88 | GCAAAAC | 138 |
| hsa-miR-19b | GATTTGCAC | 39 | ATTTGCAC | 89 | TTTGCAC | 139 |
| hsa-miR-200b | GGCAGTATT | 40 | GCAGTATT | 90 | CAGTATT | 140 |
| hsa-miR-203 | AACATTTCA | 41 | ACATTTCA | 91 | CATTTCA | 141 |
| hsa-miR-20a | AAGCACTTT | 42 | AGCACTTT | 92 | GCACTTT | 142 |
| hsa-miR-20a* | ATAATGCAG | 43 | TAATGCAG | 93 | AATGCAG | 143 |
| hsa-miR-20b | GAGCACTTT | 44 | AGCACTTT | 94 | GCACTTT | 144 |
| hsa-miR-20b* | ATACTACAG | 45 | TACTACAG | 95 | ACTACAG | 145 |

TABLE 2-continued

The following specific compounds, which may be used in the methods of the present invention, such as in the treatment of a disease, such as a disease where expression/over-expression of one or more microRNAs are indicated such as those diseases illustrated in table 1. The compounds are preferably fully phosphorothioate and each nuceltode is a LNA nucleotide, such as beta-D-oxy LNA. LNA cytosine may be 5'methyl cytosine. The compounds are directed towards the seed regions of their target microRNA (i.e. are seedmers). The compounds are as disclosed in table 1 of PCT/DK2008/000344, which discloses antimiRs targeting the microRNAs as published in miRbase and which is specifically incorporated by reference to provide oligomers which may be used in the methods of the present invention. Equivalent antimiRs can be designed by matching the -2 to -8/-9 or -10 positions (for 7, 8 or 9mers) of mature microRNAs (counting from the terminal 5' nucleotide of the microRNA (i.e. at the -1 position)-such as against the micrRNAs indicated with cancer, as disclosed in WO2008/046911.

| microRNA | 9-mers | SEQ ID | 8-mers | SEQ ID | 7-mers | SEQ ID |
|---|---|---|---|---|---|---|
| hsa-miR-21 | TGATAAGCT | 46 | GATAAGCT | 96 | ATAAGCT | 146 |
| hsa-miR-221 | CAATGTAGC | 47 | AATGTAGC | 97 | ATGTAGC | 147 |
| hsa-miR-221* | TATGCCAGG | 48 | ATGCCAGG | 98 | TGCCAGG | 148 |
| hsa-miR-222 | AGATGTAGC | 49 | GATGTAGC | 99 | ATGTAGC | 149 |
| hsa-miR-222* | GGCTACTGA | 50 | GCTACTGA | 100 | CTACTGA | 150 |
| hsa-miR-25 | AAGTGCAAT | 51 | AGTGCAAT | 101 | GTGCAAT | 151 |
| hsa-miR-26a | ATTACTTGA | 52 | TTACTTGA | 102 | TACTTGA | 152 |
| hsa-miR-363 | CCGTGCAAT | 53 | CGTGCAAT | 103 | GTGCAAT | 153 |
| hsa-miR-372 | GCAGCACTT | 54 | CAGCACTT | 104 | AGCACTT | 154 |
| hsa-miR-373 | GAAGCACTT | 55 | AAGCACTT | 105 | AGCACTT | 155 |
| hsa-miR-373* | CATTTTGAG | 56 | ATTTTGAG | 106 | TTTTGAG | 156 |
| hsa-miR-375 | AACGAACAA | 57 | ACGAACAA | 107 | CGAACAA | 157 |
| hsa-miR-92a | AAGTGCAAT | 58 | AGTGCAAT | 108 | GTGCAAT | 158 |
| hsa-miR-92a-1* | ATCCCAACC | 59 | TCCCAACC | 109 | CCCAACC | 159 |
| hsa-miR-92a-2* | ATCCCCACC | 60 | TCCCCACC | 110 | CCCCACC | 160 |
| hsa-miR-93 | CAGCACTTT | 61 | AGCACTTT | 111 | GCACTTT | 161 |

TABLE 3

Further LNA Compounds Targeting selected microRNAs. The following specific compounds, as disclosed in PCT/DK2008/000344, which may be used in the methods of the present invention, such as in the treatment of a disease, such as a disease where expression/over-expression of one or more microRNAs are indicated such as those diseases illustrated in table 1.

| SEQ ID NO | Compound Sequence | Target microRNA |
|---|---|---|
| 162 | TcAGtCTGaTaAgCT | miR-21 |
| 163 | GATAAGCT | miR-21 |
| 164 | TcAcAATtaGCAtTA | miR-155 |
| 165 | TAGCATTA | miR-155 |
| 166 | CcAttGTcaCaCtCC | miR-122 |
| 167 | CACACTCC | miR-122 |
| 168 | ATAAGCT | miR-21 |
| 169 | TGATAAGCT | miR-21 |
| 170 | CTGATAAGCT | miR-21 |
| 171 | GTCTGATAAGCT | miR-21 |
| 172 | CAGTCTGATAAGCT | miR-21 |
| 173 | TCTGATAA | miR-21 |
| 174 | ATCAGTCT | miR-21 |

TABLE 3-continued

Further LNA Compounds Targeting selected microRNAs. The following specific compounds, as disclosed in PCT/DK2008/000344, which may be used in the methods of the present invention, such as in the treatment of a disease, such as a disease where expression/over-expression of one or more microRNAs are indicated such as those diseases illustrated in table 1.

| SEQ ID NO | Compound Sequence | Target microRNA |
| --- | --- | --- |
| 175 | TCAACATC | miR-21 |
| 176 | AGCACTTT | miR-106b |
| 177 | ATTTGCAC | miR-19a |
| 178 | AgCagACaaTgTaGC | miR-221 |
| 179 | GtAgcCAgaTgTaGC | miR-222 |
| 180 | ATGTAGC | miR-221/222 |
| 181 | ACaAcCTacTaCcTC | Let-7 |
| 182 | ACTACCTC | Let-7 |
| 183 | CaCtgTCagCaCtTT | miR-106b |
| 184 | TgCatAGatTtGcAC | miR-19a |
| 185 | TACCTC | Let-7 |
| 186 | CTACCTC | Let-7 |
| 187 | TNCTACCTC | Let-7 |
| 188 | TNCTACCTC | Let-7 |
| 189 | GCaAcCTacTaCcTC | Let-7 |
| 190 | ACaAcCTccTaCcTC | Let-7 |
| 191 | ACaAaCTacTaCcTC | Let-7 |
| 192 | CTACCTC | Let-7 |
| 193 | CTAACTC | Let-7 |
| 194 | TTAGCATTA | miR-155 |
| 195 | CGATTAGCATTA | miR-155 |
| 196 | CACGATTAGCATTA | miR-155 |
| 197 | GCATTA | miR-155 |
| 198 | AGCATTA | miR-155 |
| 199 | ATTAGCATTA | miR-155 |

Further specific compounds targeting miR-122, miR-19b, miR-21, miR-155 and miR-375, which may be used are as disclosed in Table 1 WO2007/112754 and WO2007/112753 and are hereby incorporated by reference.

Pharmaceutical Compositions and Methods of Treatment

The antisense oligonucleotide or conjugate or pharmaceutical composition thereof, is typically administered to the subject in an effective dose—which may for example be determined by a dose which is sufficient to down-regulate the target RNA, or activity thereof, to a significant level over the time period between successive administration dosages, such as a level which is a therapeutic benefit to the subject. In some embodiments, the target RNA, or activity thereof is down-regulated by at least 10%, such as at least 20%, at least 30%, at least 40%, at least 50%, at least 60%, at least 70% or at least 80% or at least 90% during the time period between successive administration dosages. The pharmaceutical compositions of the invention may in some embodiments be made for administration to provide for an initial dosage build up phase, which may, depending on the disease pathology, be followed by a maintenance dosage scheme for the purpose of maintaining a concentration of the compound in the subject, such as in a target tissue of the subject, which will be effective in the treatment of the disease. The effectiveness of the dosages may in example be measured by observation of a disease parameter indicative of the state of the disease, or may depending on the target tissue, be measurable by observation of various tissue parameters, such as activity of the target RNA or amount of viral genome, or in alternative example on a measurable disease state dependent parameter in plasma. However, in some diseases, in non limiting example such a disease could be a viral disease, after the build up phase, a maintenance dosage could be given for a time period wherein the purpose is to maintain a relatively high activity or concentration of the compound in the target tissue, while e.g. the viral titre is decreased or other disease parameters are improved, after which the interval between each dosing could be increased or the dosage given at each dosing could be decreased or both, in order to maintain the disease at the new low level using the minimal needed effective dosage and at the same time obtain minimum side effects and the least inconvenience for the patient by having a high time interval in between administrations.

In some embodiments, after the build up phase, a maintenance dosage will be administered wherein the purpose is to maintain an effective concentration in the target tissue, in order to obtain the desired effect on important disease parameters, wherein the time interval in between each administration is large to avoid the inconvenience for the patient of the administration, and the dosage is kept to a minimum to avoid side effects while still maintaining the effect on the selected disease parameters.

In some embodiments, the time interval between the at least two dosages, such as maintenance dosages, is selected from any one of at least 14 days, such as at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 or at least 125 days. In some embodiments, the time interval between said at least two dosages, such as maintenance dosages, is selected from any one of at least 2 weeks, such as at least 3, 4, 5, 6, 7, 8, 9, 10, 11, 12, 13, 14, 15, 16, 17 or at least 18 weeks. In some embodiments, the time interval between said at least two dosages, such as maintenance dosages, is selected from any one of at least ½ month, such as at least 1, 1½, 2, 2½, 3, 3½, 4 or at least 4½ month.

In some embodiments, the treatment will be maintained for as long as the patient has symptoms of active disease. In some embodiments, the treatment may be paused for a period, and subsequently resumed by an initial period of high or frequent dosing to re-build effective tissue concentrations of the compound, followed by maintenance treatment according to the description.

In one preferred embodiment, the time interval between the at least two dosages, such as the maintenance dosages, is at least 14 days. In one preferred embodiment, the time interval between dosages is at least 21 days. In one preferred embodiment, the time interval between dosages is at least 4 weeks. In one preferred embodiment, the time interval between dosages is at least 5 weeks. In one preferred embodiment, the time interval between dosages is at least 6 weeks. In one preferred embodiment, the time interval between dosages is at least 7 weeks. In one preferred embodiment, the time interval between dosages is at least 8 weeks. Such dosages may be maintenance dosages.

In some embodiments a concentration of the oligomer in circulation in the subject, such as in the blood plasma, is maintained at a level of between 0.04 and 25 nM, such as between 0.8 and 20 nM.

In some embodiments, the dosage of the compound administered at each dosing, such as unit dose, is within the range of 0.01 mg/kg-25 mg/kg. In some embodiments, the dosage, such as unit dose, of the compound administered at each dosing is within the range of 0.05 mg/kg-20 mg/kg. In some embodiments, the dosage (such as unit dose) of the compound administered at each dosing is within the range of 0.1 mg/kg-15 mg/kg. In some embodiments, the (such as unit dose) dosage of compound administered at each dosing is within the range of 1 mg/kg-15 mg/kg. In some embodiments, the dosage of the compound administered at each dosing is within the range of 1 mg/kg-10 mg/kg. In some embodiments, the dosage (such as unit dose) of the compound administered at each dosing is within the range of 0.01 mg/kg-25 mg/kg, such as about 0.01, 0.05, 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24 or such as about 25 mg/kg, each of which are individual embodiments.

In some embodiments, the compositions of the invention (such as unit dose) are made for parenteral administration methods, such as in non limiting example, intra venous, sub cutaneous, intra peritoneal, intra cerebro vascular, intra nasal. In some embodiments, the administration is oral.

The oligomer of the invention may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference. Preferably the pharmaceutical composition of the invention further comprises a pharmaceutically acceptable carrier.

Preferably, the compound of the invention is included in a unit formulation (i.e. unit dose) such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The dosage of the pharmaceutical composition is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides. Generally it can be estimated based on $EC_{50}$s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

The formulated drug may comprise pharmaceutically acceptable binding agents and adjuvants. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In some embodiments the active oligo is administered IV, IP, orally, topically or as a bolus injection or administered directly in to the target organ. In an exemplary embodiment, each dosage is administered in via parenteral injection or infusion, including intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances, which increase the viscosity of the suspension including, for example, sodium carboxymethylcellulose, sorbitol and/or dextran. The suspension may also contain stabilizers.

For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

An oligonucleotide of the invention may be mixed with any material that do not impair the desired action, or with material that supplement the desired action. These could include other drugs including other nucleoside compounds.

Optionally, the pharmaceutical according to the invention comprises therapeutic agents, such as further antisense compounds, chemotherapeutic compounds, anti-inflammatory compounds, antiviral compounds and/or immuno-modulating compounds. Anti-inflammatory drugs, including but not limited to nonsteroidal anti-inflammatory drugs and corticosteroids, antiviral drugs, and immuno-modulating drugs may also be combined in compositions of the invention.

Two or more combined compounds may be used together or sequentially, i.e. the compound according to the invention may be used prior to, during or subsequent to one or more of the other therapeuticagents referred to herein.

Oligonucleotides of the invention may also be conjugated to active drug substances, for example, aspirin, ibuprofen, a sulfa drug, an antidiabetic, an antibacterial or an antibiotic. Preferably, the pharmaceutical composition according to the invention further comprises at least one chemotherapeutic agent. Said chemotherapeutic agent is preferably selected from the group consisting of adrenocorticosteroids, such as prednisone, dexamethasone or decadron; altretamine (hexylen, hexamethylmelamine (HMM)); amifostine (ethyol); aminoglutethimide (cytadren); amsacrine (M-AMSA); anastrozole (arimidex); androgens, such as testosterone; asparaginase (elspar); *bacillus* calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine).

In a certain embodiments, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially. i.e. the compound according to the invention may be used prior to, during or subsequent to one or more of the other therapeutic agents referred to herein.

The pharmaceutical composition of the invention may constitute a pro-drug. Therefore, in some embodiments of the invention the compound of the invention may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthioethyl (t-butyl-SATE). These protection groups are nuclease resistant and are selectively removed intracellulary.

Preferably the pharmaceutical composition of the invention further comprises anti-inflamatory compounds and/or antiviral compounds.

In a preferred embodiment, the LNA antisense anti microRNA compounds used in the invention are formulated in saline.

Nucleotides and Nucleotide Analogues.

The term "nucleotide" as used herein, refers to a glycoside comprising a sugar moiety, a base moiety and a covalently linked phosphate group and covers both naturally occurring nucleotides, such as DNA or RNA, preferably DNA, and non-naturally occurring nucleotides comprising modified sugar and/or base moieties, which are also referred to as "nucleotide analogues" herein.

Non-naturally occurring nucleotides include nucleotides which have modified sugar moieties, such as bicyclic nucleotides or 2' modified nucleotides, such as 2' substituted nucleotides.

The terms "corresponding to" and "corresponds to" refer to the comparison between the nucleotide sequence of the oligomer or contiguous nucleotide sequence (a first sequence) and the equivalent contiguous nucleotide sequence of either the entire or a sub-sequence of the reverse complement of the target RNA—a oligomer sequence or contiguous nucleotide sequence thereof, which corresponds to the RNA target typically comprises no mismatches, or no more than one mismatch, when aligned to the reverse complement of the entire or a sub-sequence of the target RNA.

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligomer, i.e. have no functional effect on the way the oligomer works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; Nucl. Acid Res., 1997, 25, 4429-4443 and Uhlmann; Curr. Opinion in Drug Development, 2000, 3(2), 293-213, and in Sceme 1:

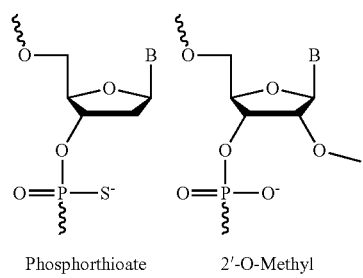

Scheme 1

Phosphorthioate    2'-O-Methyl

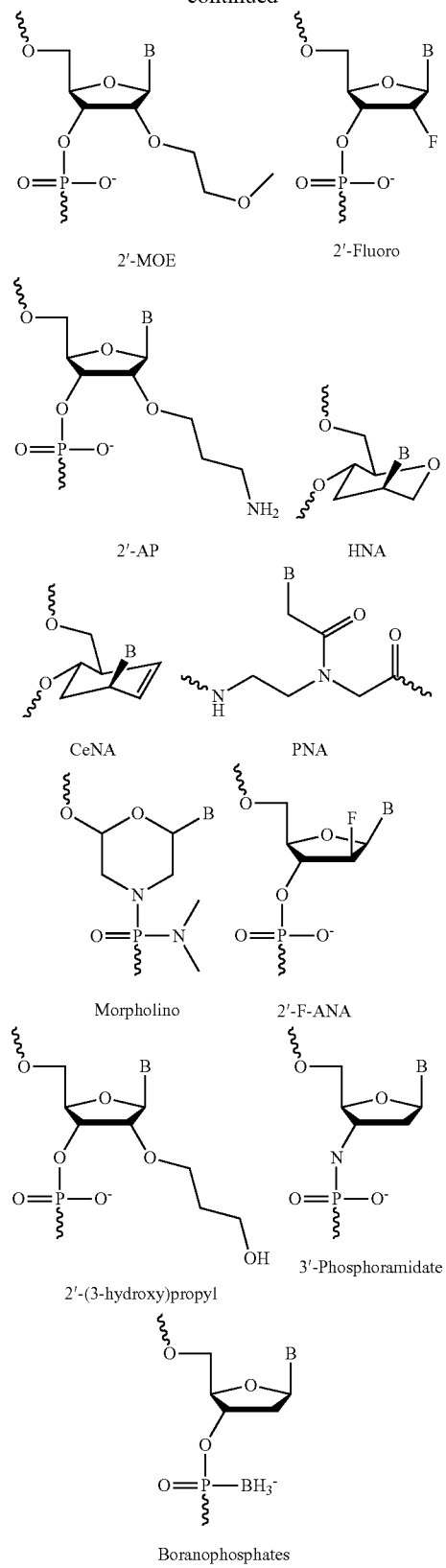

2'-MOE    2'-Fluoro

2'-AP    HNA

CeNA    PNA

Morpholino    2'-F-ANA

2'-(3-hydroxy)propyl    3'-Phosphoramidate

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by PCT/DK2006/000512 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer or oligomers comprise at least 2 nucleotide analogues. In some embodiments, the oligomer or oligomers comprises from 3-8 nucleotide analogues, e.g. 6 or 7 nucleotide analogues. In the by far most preferred embodiments, particularly in relation to the second oligomer, but may also refer to the first oligomer, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer or oligomers are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as the oligomer or oligomers may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the second oligomer comprises both LNA and 2'-MOE-RNA or 2'-fluoro nucleotides, and may, in some embodiment consist of LNA and 2'-MOE, or LNA and 2'-fluoro nucleotides.

In some embodiments, the oligomer or oligomers comprises at least one Locked Nucleic Acid (LNA) unit, such as 1, 2, 3, 4, 5, 6, 7, or 8 LNA units, such as between 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5' methyl-Cytosine. In some embodiments of the invention, the oligomer or oligomers, may comprise both LNA and DNA units. In some embodiments, the combined total of LNA and DNA units is 10-25, or 10-20, such as 12-16. In some embodiments, the nucleotide sequence of the oligomer, such as the contiguous nucleotide sequence consists of at least one LNA and the remaining nucleotide units are DNA units. In some embodiments, the oligomer or oligomers, comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer or oligomers is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleotide analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a biradical 'bridge' between C2' and C4' of the ribose sugar ring—for example as shown as the biradical $R^{4*}$—$R^{2*}$ as described below.

The LNA used in the oligonucleotide compounds of the invention preferably has the structure of the general formula I

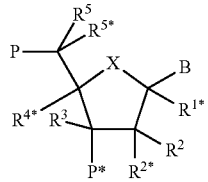

Formula 1 wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a biradical consisting of 1-4 groups/atoms selected from —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^a R^b$)—C($R^a R^b$)—, C($R^a R^b$)—O—, C($R^a R^b$)—NR$^a$—, C($R^a R^b$)—S—, and C($R^a R^b$)—C($R^a R^b$)—O—, wherein each $R^a$ and $R^b$ may optionally be independently selected. In some embodiments, $R^a$ and $R^b$ may be, optionally independently selected from the group consisting of hydrogen and $C_{1-6}$alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $O_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —CH$_3$, —CH$_2$—CH$_3$, —CH$_2$—O—CH$_3$, and —CH=CH$_2$. Suitably in some embodiments, either $R^5$ or $R^{5*}$ are hydrogen, where as the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, OJ$_1$, SJ$_1$, NJ$_1$J$_2$, N$_3$, COOJ$_1$, CN, O—C(=O)NJ$_1$J$_2$, N(H)C(=NH)NR,R$_2$ or N(H)C(=X)N(H)J$_2$ wherein X is O or S; and each J$_1$ and J$_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $O_{2-6}$ alkynyl, $C_{1-6}$ aminoalkyl, substituted $C_{2-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, NJ$_1$J$_2$, N$_3$, CN, OJ$_1$, SJ$_1$, O—C(=O)NJ$_1$J$_2$, N(H)C(=NH)NJ,J$_2$ or N(H)C(O)N(H)J$_2$. In some embodiments each J$_1$ and J$_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)NJ$_1$J$_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2' thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^a R^b$)—O—, —C($R^a R^b$)—C($R^c R^d$)—O—, —C($R^a R^b$)—C($R^c R^d$)—C($R^e R^f$)—O—, —C($R^a R^b$)—O—C($R^c R^d$)—, —C($R^a R^b$)—O—C($R^c R^d$)—O—, —C($R^a R^b$)—C($R^c R^d$)—, —C($R^a R^b$)—C($R^c R^d$)—C($R^e R^f$)—, —C($R^a$)=C($R^b$)—C($R^c R^d$)—, —C($R^a R^b$)—N($R^c$)—, —C($R^a R^b$)—C($R^c R^d$)—N($R^e$)—, —C($R^a R^b$)—N($R^c$)—O—, and —C($R^a R^b$)—S—, —C($R^a R^b$)—C($R^c R^d$)—

S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical $C(R^aR^b)$—$N(R^c)$—O—, wherein $R^a$ and $R^b$ are independently selected from the group consisting of hydrogen, halogen, $O_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical $C(R^aR^b)$—O—$C(R^cR^d)$—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $O_{2-6}$ alkynyl, $O_{1-6}$ alkoxyl, substituted $O_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $O_{2-6}$ alkenyl, substituted $O_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3C$(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—$N(R^c)$—, wherein $R^c$ is $C_{1-12}$ alkyloxy. In some embodiments $R^{4*}$ and $R^{2*}$ together designate a biradical —$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$-aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)$NJ_1J_2$ or N(H)C(=X=N(H)$J_2$ wherein X is O or S; and each of $J_1$ and $J_2$ is, independently, H, $C_{1-6}$ alkyl, $O_{2-6}$ alkenyl, $O_{2-6}$ alkynyl, $C_{1-6}$aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $O_{2-6}$ alkenyl, substituted $O_{2-6}$ alkenyl, $C_{2-6}$ alkynyl or substituted $O_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181.

In some embodiments, $R^{4*}$ and $R^{2*}$ form the biradical —Q—, wherein Q is $C(q_1)(q_2)C(q_3)(q_4)$, $C(q_1)$=$C(q_3)$, $C[=C(q_1)(q_2)]$—$C(q_3)(q_4)$ or $C(q_1)(q_2)$—$C[=C(q_3)(q_4)]$; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C(=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181.

In some embodiments the LNA used in the oligonucleotide compounds of the invention preferably has the structure of the general formula II:

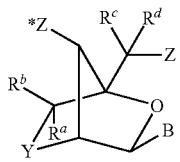

Formula II wherein Y is selected from the group consisting of —O—, —CH$_2$O—, —S—, —NH—, N(R$^e$) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and O$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$); and R$^H$ is selected from hydrogen and C$_{1-4}$-alkyl. In some embodiments R$^a$, R$^b$R$^c$, R$^d$ and R$^e$ are, optionally independently, selected from the group consisting of hydrogen and C$_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

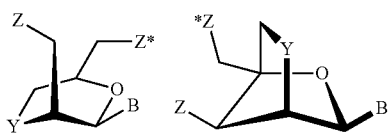

Specific exemplary LNA units are shown below:

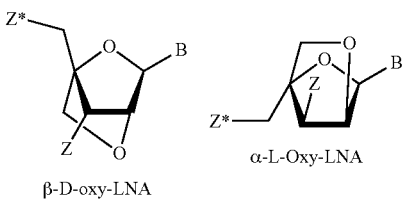

β-D-oxy-LNA  α-L-Oxy-LNA

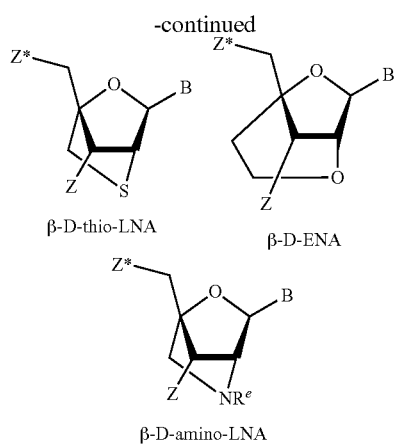

β-D-thio-LNA  β-D-ENA

β-D-amino-LNA

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Internucleotide Linkages

The terms "linkage group" or "internucleotide linkage" are intended to mean a group capable of covalently coupling together two nucleotides, two nucleotide analogues, and a nucleotide and a nucleotide analogue, etc. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within PCT/DK2006/000512, for example the internucleotide linkages listed on the first paragraph of page 34 of PCT/DK2006/000512 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred.

The internucleotide linkages in the oligomer may be phosphodiester, phosphorothioate or boranophosphate. Phosphorothioate is preferred, for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units can modify the bioavailability and/or bio-distribution of an oligomer —see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example between 1-50, such as 2-20 such as 3-10 amino acid residues in length, and/or polyalkylene oxide such as polyethylglycol(PEG) or polypropylene glycol—see WO 2008/034123, hereby incorporated by reference. Suitably the positively charged polymer, such as a polyalkylene oxide may be attached to the oligomer of the invention via a linker such as the releasable inker described in WO 2008/034123.

By way of example, the following conjugate moieties may be used in the conjugates of the invention:

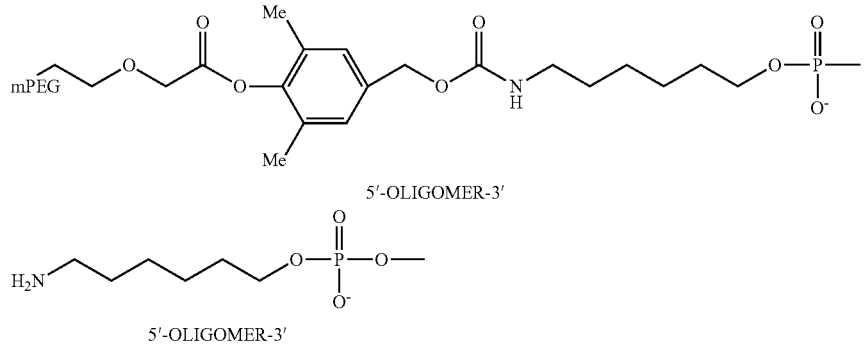

5'-OLIGOMER-3'

5'-OLIGOMER-3'

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W. Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group ($-O-C(O)-(CH_2)_w NH$).

In other embodiments, the oligomers are functionalized with a hindered ester containing a $(CH_2)_w$sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group ($-O-C(O)-(CH_2)_w SH$)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated by reference herein in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Specific embodiments

1. A pharmaceutical composition comprising an effective dosage of an anti microRNA oligonucleotide, or an antisense oligonucleotide targeting a mRNA, non-coding RNA or a viral genome, wherein the composition is made for administration to a primate with a time interval between each administration of at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days.
2. A pharmaceutical composition according to embodiment 1, wherein the effective dosage in within the range of 0.01 mg/kg-25 mg/kg, such as about 0.01, 0.05, 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24 or such as about 25 mg/kg.
3. A pharmaceutical composition according to any one of embodiments 1-2, wherein the oligonucleotide comprises nucleotide analogues
4. A pharmaceutical composition according to embodiment 3, wherein at least one of the nucleotide analogues is chosen from the group consisting of: 2'-O-alkyl-RNA monomers, 2'-amino-DNA monomers, 2'-fluoro-DNA monomers, LNA monomers, arabino nucleic acid (ANA) mononmers, 2'-fluoro-ANA monomers, HNA monomers, INA monomers.
5. A pharmaceutical composition according to embodiment 4, wherein the nucleotide analogues are independently selected from the group consisting of 2'-MOE-RNA (2'-O-methoxyethyl-RNA), 2'Fluoro-DNA, and LNA.
6. A pharmaceutical composition according to embodiment 5, wherein the nucleotide analogues is a locked nucleic acid (LNA)
7. A pharmaceutical composition according to any one of embodiments 1-6, wherein the oligonucleotide is designed as a mixmer that is not cleaved by RNase H.
8. A pharmaceutical composition according to any one of embodiments 1-7, wherein the compound is any one of the oligonucleotides listed as SEQ ID NO: 162-199.
9. A pharmaceutical composition according to any one of the preceding embodiments, wherein the compound is a modulator of miR-122.
10. A pharmaceutical composition according to any one of embodiments 1-9, wherein the composition is administered to an individual suffering from a disease wherein lowering of the activity of a particular microRNA is beneficial, such as, but not limited to a disease selected from the list of cardiac arythmia, cardiac hypertrophy, cancer, hypercholesterolemia, metabolic disorders, psoriasis, diabetes, auto immune disorders, hemochromatosis, hepatitis C infection, or other viral infection.
11. A pharmaceutical composition according to any of the preceding embodiments, wherein the composition is made for a dosing schedule where there is an initial build up of an effective dosage by a sequence of administrations of the composition, followed by maintenance administrations with long time intervals between each administration of at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days.
12. A pharmaceutical composition according to any one of embodiments 1-11, wherein the initial build up of the effective dosage occur within 1, 2, 3, 4, 5, 6, 7, 8, 9, 10, 11, 12, 13 or 14 days or within 3, 4, 5 or 6 weeks.
13. An antisense oligonucleotide for administration to a primate, wherein the oligonucleotide is complementary to the sequence of a microRNA, a mRNA, a non-coding RNA or a viral genome, and wherein the antisense oligonucleotide is made for administration in a dosage that will provide an effective concentration of the oligonucleotide in the target tissue, and wherein the oligonucleotide may be administered with a time interval between each administration of at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days.
14. An antisense oligonucleotide according to embodiment 13, wherein the effective dosage in within the range of 0.01 mg/kg-25 mg/kg, such as about 0.01, 0.05, 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24 or such as about 25 mg/kg.
15. An antisense oligonucleotide according to any one of embodiments 13-14, wherein the oligonucleotide comprises nucleotide analogues
16. An antisense oligonucleotide according to embodiment 15, wherein at least one of the nucleotide analogues is chosen from the group consisting of: 2'-O-alkyl-RNA monomers, 2'-amino-DNA monomers, 2'-fluoro-DNA monomers, LNA monomers, arabino nucleic acid (ANA) mononmers, 2'-fluoro-ANA monomers, HNA monomers, INA monomers.
17. An antisense oligonucleotide according to embodiment 16, wherein the nucleotide analogues are independently selected from the group consisting of 2'-MOE-RNA (2'-O-methoxyethyl-RNA), 2'Fluoro-DNA, and LNA.
18. An antisense oligonucleotide according to embodiment 17, wherein the nucleotide analogues is a locked nucleic acid (LNA)
19. An antisense oligonucleotide according to any one of embodiments 13-18, wherein the oligonucleotide is designed as a mixmer that is not cleaved by RNase H.
20. An antisense oligonucleotide according to any one of embodiments 13-19, wherein the oligonucleotide is any one of SEQ ID NO: 162-199.
21. An antisense oligonucleotide according to any one of the preceding embodiments, wherein the oligonucleotide is a modulator of miR-122.
22. An antisense oligonucleotide according to any one of embodiments 13-21, wherein the oligonucleotide is made to be administered to an individual suffering from a disease wherein lowering of the activity of a particular microRNA is beneficial, such as, but not limited to a disease selected from the list of cardiac arythmia, cardiac hypertrophy, cancer, hypercholesterolemia, metabolic disorders, psoriasis, diabetes, auto immune disorders, hemochromatosis, hepatitis C infection, or other viral infection.
23. An antisense oligonucleotide according to any of embodiments 13-22, wherein the oligonucleotide is made for a dosing schedule wherein there is an initial build up of an effective dosage in the target tissue, by a sequence of one or more administrations of the oligonucleotide, followed by maintenance administrations with long term intervals between each administration of at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days, wherein the maintenance administrations will maintain an effective dosage of the oligonucleotide in the target tissue.
24. An antisense oligonucleotide according to any one of embodiments 13-23, wherein the initial build up of the effective dosage occur within 1, 2, 3, 4, 5, 6, 7, 8, 9, 10, 11, 12, 13 or 14 days or within 3, 4, 5 or 6 weeks.
25. A method of inhibiting the activity of a microRNA, an mRNA, a non-coding RNA, or a viral genome in a primate, by administration of a pharmaceutical composition according to any one of embodiments 1-12.
26. A method of treating a disease or disorder in a primate, wherein the disease or disorder is characterized by being sensitive to down-regulation of a microRNA, an mRNA, a non-coding RNA, or a viral genome and wherein the method comprises at least two steps, a first step which is a dosage building step during which frequent administrations (at least one) of an oligonucleotide which is antisense to the above microRNA, mRNA, non-coding RNA, or viral genome, will build an effective dosage of the antisense oligonucleotide in the target tissue, and a second step wherein the effective dosage is maintained in the target tissue by less frequent administrations of the oligonucleotide to the primate, wherein the time interval in the maintenance phase, between each administration is at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days.
27. A method of treating a disease or disorder in a primate according to embodiment 26, wherein the oligonucleotide comprises nucleotide analogues.
28. A method of treating a disease or disorder in a primate according to embodiment 27, wherein at least one of the nucleotide analogues is chosen from the group consisting of: 2'-O-alkyl-RNA monomers, 2'-amino-DNA monomers, 2'-fluoro-DNA monomers, LNA monomers, arabino nucleic acid (ANA) mononmers, 2'-fluoro-ANA monomers, HNA monomers, INA monomers.
29. A method of treating a disease or disorder in a primate according to embodiment 28, wherein the nucleotide analogues are independently selected from the group consisting of 2'-MOE-RNA (2'-O-methoxyethyl-RNA), 2'Fluoro-DNA, and LNA.
30. A method of treating a disease or disorder in a primate according to embodiment 29, wherein the nucleotide analogues is a locked nucleic acid (LNA).
31. A method of treating a disease or disorder in a primate according to any one of embodiments 26-30, wherein the oligonucleotide is essentially incapable of recruiting RNAseH.
32. A method of treatment according to any one of embodiments 26-31, wherein the oligonucleotide is any one of SEQ ID NO: 162-199.
33. A method of treating a disease or disorder in a primate according to any one of embodiments 26-32, wherein the microRNA is miR-122.
34. A method of treating a disease or disorder in a primate according to embodiment 33, wherein a composition according to any one of embodiments 1-12 is administered to an individual suffering from a disease wherein lowering of the activity of a particular microRNA is beneficial, such as, but not limited to a disease selected from the list of cardiac arythmia, cardiac hypertrophy, cancer, hypercholesterolemia, metabolic disorders, psoriasis, diabetes, auto immune disorders, hemochromatosis, hepatitis C infection or other viral infection.
35. A method of treating a disease or disorder in a primate according to any one of embodiments 26-34, wherein there is an initial build up of an effective dosage by a sequence of administrations followed by maintenance administrations with long time intervals between each administration of at least 14 days, such as at least 15, 16, 17, 18, 19, 20, 25, 30, 35, 40, 45, 50, 55, 60, 65, 70, 75, 80, 85, 90, 95, 100, 105, 110, 115, 120, or at least 125 days.
36. A method of treating a disease according to any one of embodiments 26-35, wherein the initial build up of the effective dosage occur within 1, 2, 3, 4, 5, 6, 7, 8, 9, 10, 11, 12, 13 or 14 days or within 3, 4, 5 or 6 weeks.
37. A method of treating a disease according to any one of embodiments 1-36, wherein the initial dosage building is by continuous infusion, or by injection of a slow release formulation, or by inhalation.
38. A method of treating a disease according to any one of embodiments 1-37, wherein the maintenance dosage is administered by intravenous injection, subcutaneous, intraperitoneal, inhalation, icv., intramuscular, intraorbital, intracapsular, intraspinal, intrasternal, intravenous or intranasal.

Methods Summary

The LNA-modified oligonucleotides were synthesized as unconjugated LNA/DNA mixmers with a complete phosphorothioate backbone. The 2'-OMe oligonucleotides for HCV replication assays and the antagomir-122 were synthesized as described[14,6]. Saline-formulated compounds were administered into normal and hypercholesterolemic C57BL/6J mice by intraperitoneal injections and blood samples were collected for cholesterol and serum transaminase measurements. Liver samples were prepared for RNA extraction, miRNA quantification and liver histopathology. Microarray expression profiling of mouse liver RNAs was carried out according to standard Affymetrix protocols and the data were submitted to the Array Express database. For data analysis standard Bioconductor[24] packages were used. Transcript 3'UTRs were searched for the presence of miR-122 seed matches[25] using in-house Perl scripts. mRNA quantification was carried out using standard TaqMan assays (Applied Biosystems). Thirty female drug-naïve young adult African green monkeys were assigned to six groups (n=5 per group) and dosed once daily on days 1, 3, and 5 by intravenous infusions over ~10 min at a rate of 24 ml/kg/h. Four treatment groups received phosphate-buffered saline (PBS) or 1, 3 or 10 mg/kg PBS-formulated LNA-antimiR, all of which received liver biopsies, while two groups received PBS or 10 mg/kg PBS-formulated LNA-antimiR without liver biopsies. Blood samples were collected for clinical chemistry and hematology measurements. Total cholesterol was determined enzymatically in microtitre plates. Lipoprotein cholesterol distributions were determined by FPLC and the apolipoprotein levels by ELISA. In situ detection of LNA-antimiR was performed on frozen liver sections of LNA-antimiR treated and control monkeys using a FAM-labelled LNA probe and HRP-conjugated polyclonal rabbit anti-FITC antibodies (DAKO) combined with Cyanine 3-Plus tyramide (Perkin-Elmer). Northern blot analyses of liver RNAs were performed using a 5' FAM-labelled LNA-modified miR-122 probe and an antifluorescein-HRP antibody (PerkinElmer, NEF710) combined with the ECL advanced kit for detection (GE Healthcare Life Sciences).

Reference List

1. Ambros, V. The functions of animal microRNAs. *Nature* 431, 350-355 (2004).
2. Bartel, D. P. MicroRNAs: genomics, biogenesis, mechanism, and function. *Cell* 116, 281-297 (2004).
3. Kloosterman, W. P. & Plasterk, R. H. The diverse functions of microRNAs in animal development and disease. *Dev. Cell* 11, 441-450 (2006).
4. Soifer, H. S., Rossi, J. J. & Saetrom, P. MicroRNAs in Disease and Potential Therapeutic Applications. *Mol Ther* (2007).
5. Esau, C. et al. miR-122 regulation of lipid metabolism revealed by in vivo antisense targeting. *Cell Metab* 3, 87-98 (2006).
6. Krutzfeldt, J. et al. Silencing of microRNAs in vivo with 'antagomirs'. *Nature* 438, 685-689 (2005).
7. Grimson, A. et al. MicroRNA targeting specificity in mammals: determinants beyond seed pairing. *Mol Cell* 27, 91-105 (2007).
8. Alvarez-Garcia, I. & Miska, E. A. MicroRNA functions in animal development and human disease. *Development* 132, 4653-4662 (2005).
9. Abelson, J. F. et al. Sequence variants in SLITRK1 are associated with Tourette's syndrome. *Science* 310, 317-320 (2005).
10. Calin, G. A. & Croce, C. M. MicroRNA signatures in human cancers. *Nat. Rev. Cancer* 6, 857-866 (2006).

11. Eisenberg, I. et al. Distinctive patterns of microRNA expression in primary muscular disorders. *Proc Natl Acad Sci USA* 104, 17016-17021 (2007).
12. Esquela-Kerscher, A. & Slack, F. J. Oncomirs—microRNAs with a role in cancer. *Nat. Rev. Cancer* 6, 259-269 (2006).
13. He, L. et al. A microRNA polycistron as a potential human oncogene. *Nature* 435, 828-833 (2005).
14. Jopling, C. L., Yi, M., Lancaster, A. M., Lemon, S. M. & Sarnow, P. Modulation of hepatitis C virus RNA abundance by a liver-specific MicroRNA. *Science* 309, 1577-1581 (2005).
15. Lu, J. et al. MicroRNA expression profiles classify human cancers. Nature 435, 834-838 (2005).
16. Pedersen, I. M. et al. Interferon modulation of cellular microRNAs as an antiviral mechanism. *Nature* 449, 919-922 (2007).
17. Triboulet, R. et al. Suppression of microRNA-silencing pathway by HIV-1 during virus replication. *Science* 315, 1579-1582 (2007).
18. van Rooij, E. et al. Control of stress-dependent cardiac growth and gene expression by a microRNA. *Science* 316, 575-579 (2007).
19. Yang, B. et al. The muscle-specific microRNA miR-1 regulates cardiac arrhythmogenic potential by targeting GJA1 and KCNJ2. *Nat. Med.* 13, 486-491 (2007).
20. Randall, G. et al. Cellular cofactors affecting hepatitis C virus infection and replication. *Proc Natl Acad Sci USA* 104, 12884-12889 (2007).
21. Krutzfeldt, J. et al. Specificity, duplex degradation and subcellular localization of antagomirs. *Nucleic Acids Res* 35, 2885-2892 (2007).
22. Elmen, J. et al. Antagonism of microRNA-122 in mice by systemically administered LNA-antimiR leads to up-regulation of a large set of predicted target mRNAs in the liver. *Nucleic Acids Res* (2007).
23. Lim, L. P. et al. Microarray analysis shows that some microRNAs downregulate large numbers of target mRNAs. *Nature* 433, 769-773 (2005).
24. Gentleman, R. C. et al. Bioconductor: open software development for computational biology and bioinformatics. *Genome Biol* 5, R80 (2004).
25. Lewis, B. P., Burge, C. B. & Bartel, D. P. Conserved seed pairing, often flanked by adenosines, indicates that thousands of human genes are microRNA targets. *Cell* 120, 15-20 (2005).

EXAMPLES

Example 1

Oligonucleotides used in the present examples. Unconjugated LNA-modified antimiR-122 DNA oligonucleotides were synthesized with a complete phosphorothioate backbone, except for uptake studies where additional LNA oligonucleotides with a 50% phosphorothioate or a phosphodiester backbone were used. The sequence of the high-affinity LNA-antimiR-122 was: 5'-CcAttGTcaCaCtCC-3' (Seq ID # 11), LNA mismatch oligonucleotide used in mouse studies: 5'-CcAttCTcaCaCtGC-3' (Seq ID #), and LNA control used in the hepatitis C virus (HCV) replication assays: 5'-CcAttCTgaCcCtAC-3' (Seq ID #) (LNA uppercase, DNA lowercase). The 2'-OMe oligonucleotides for HCV replication assays and the antagomir-122 were synthesized as described[14,6].

TABLE 4

| Seq ID # | Tm (° C.) | Seq. 5'-3' (Uppercase LNA, Lowercase DNA) | |
|---|---|---|---|
| 1 | | uguuugugguaacagu<u>gugaggu</u> | miR-122 3'-5' |
| 2 | 62 | AttGtcAcaCtcC | |
| 3 | 65 | ccAttGtcAcaCtcC | |
| 4 | 66 | atTgtCacActCc | |
| 5 | 70 | ccAttGtcAcaCtcCa | |
| 6 | 72 | cCaTtGtCaCcCtCc | |
| 7 | 73 | cCatTgtCacActCc | |
| 8 | 74 | AttGTcaCaCtCC | |
| 9 | 75 | aTtGtCaCaCtCc | |
| 10 | 76 | cCatTgtCacActCca | |
| 11 | 80 | CcAttGTcaCaCtCC | selected LNA-antimiR, |
| 200 | | CcAttCTcaCaCtGC | LNA mismatch mouse |
| 201 | | CcAttCTgaCcCtAC | LNA control |

Table 4: Oligo Tm against complementary mature miR-122 RNA, oligo sequence.
All oligonucleotides were fully thiolated except s10 which is partially thiolated (see antagomir, Kreutzfeldt et al. 2005).
Mature miR-122 is displayed in 3' to 5' direction with cleavage site marked bold and seed underlined.

Example 2

In vivo experiments. C57BL/6J female mice were administered once every second day over a five-day-period with saline or saline-formulated LNA-antimiR, antagomir-122 or LNA mismatch control, allowing the mice to receive an injection volume of 10 ml/kg with daily intraperitoneal doses ranging from 1 to 25 mg/kg. The mice were sacrificed 48 hours after treatment. Prior to sacrifice, retro-orbital sinus blood was collected in EDTA-coated tubes followed by isolation of the plasma fraction and measurement of total cholesterol using ABX Pentra Cholesterol CP(Horiba ABX Diagnostics). In the mouse dose response study, single i.p. injections ranging from 1 to 200 mg/kg LNA-antimiR were administered and plasma cholesterol was measured 6 days after treatment. Diet-induced obesity mouse model was generated by feeding C57BL/6J female mice on a high fat diet (D12492, Research Diets) for 13 weeks. Hypercholesterolemic mice were treated with two weekly intraperitoneal doses of 5 mg/kg LNA-antimiR or LNA control for six weeks. Serum alanine aminotransferase (ALT) and aspartate aminotransferase (AST) levels were determined using enzymatic assays (Horiba ABX Diagnostics, France).

Thirty female drug-naïve young adult African green monkeys were assigned to six treatment groups (n=5 per group) and dosed once daily on days 1, 3, and 5 by intravenous infusion over ~10 min at a rate of 24 ml/kg/h via a catheter inserted into the saphenous vein. Four groups, all of which received liver biopsies, were treated with phosphate-buffered saline (PBS) or 1, 3 or 10 mg/kg PBS-formulated LNA-antimiR, while two groups received PBS or 10 mg/kg PBS-formulated LNA-antimiR without liver biopsies. The animals were sedated with ketamine (7.5 mg/kg) and xylazine (1.5 mg/kg) prior to and during dosing and at biopsy and phlebotomy time points. Percutaneous liver biopsies were performed one and 90 days post treatment to obtain two core biopsies from the right and left lobe. Half of each biopsy was immediately immersed in RNA later (Qiagen), while the remaining biopsy was divided into fixation in paraformaldehyde for hematoxylin and eosin staining and into cryopreservation for in situ analysis. Blood samples were obtained for the biopsied animals prior to and 24 h after treatment via superficial venipuncture, while additional blood samples were collected for all treatment groups throughout the study. Samplings were performed prior to feeding after a period of 12 hours without access to food to minimize dietary effects on cholesterol measurements.

Example 3

Primate hematology, clinical chemistry and plasma lipid measurements and lipoprotein analysis. Hematology measurements were carried out by optical and mechanical methodologies and automated cell counter, whereas clinical chemistries were measured using a Hitachi 747 analysis system by Antech Diagnostics. Total plasma cholesterol was determined enzymatically in microtitre plates. Lipoprotein cholesterol distributions were determined by fast protein liquid chromatography (FPLC) and apolipoproteins using ELISA by Dr. Martha Wilson at Wake Forest University.

Example 4

In situ hybridization. Detection of LNA-antimiR was performed on 10 m primate liver cryosections. Slides were thawed, fixed in 4% paraformaldehyde for 10 min at room temperature and treated in acetic anhydride/triethanolamine followed by rinsing in PBS. Slides were pre-hybridized in 50% formamide, 5×SSC, 500 ug/mL yeast tRNA, 1×Denhardt's solution at 48° C. for 30 min. LNA-antimiR was detected using a complementary FAM-labelled LNA probe hybridized to liver sections for 30 min at 48° C. followed by 3×10 min post-hybridization washes in 0.1×SSC at 52° C. Following a 10 min exposure to 3% $H_2O_2$, slides were pre-incubated for 15 min with blocking buffer (0.1 M Tris, 0.15 mM NaCl) and 1% blocking reagent (TN B, Perkin Elmer TSA kit) and subsequently with polyclonal rabbit anti-FITC antibodies conjugated to horseradish peroxidase (DAKO, 1:500 in TNB) for 30 min. Slides were rinsed with TN buffer containing 0.3% Triton-X100, and incubated with Cyanine 3-Plus tyramide (Perkin-Elmer, 1:100 in amplification buffer). The slides were rinsed and mounted in Vectashield containing DAPI (Vector Laboratories) and analyzed on a Leica epifluorescence microscope equipped with a CCD camera (Leica Microsystems) and NIS-Elements software.

Example 5

Microarray expression profiling and miR-122 target site analysis. Liver RNAs from hypercholesterolemic mice were labelled and hybridized to Affymetrix Mouse Genome 430 2.0 arrays according to the manufacturer's instructions. The expresso function from the affy-package was used for low level data analysis using rma-based background correction, quantile normalization and summarizing probe sets by Bioconductor's[24] implementation of the Li and Wong summary method. Expression profiles were subjected to hierarchical clustering using Euclidean distance measure and Ward's agglomeration method. The array data were submitted to the Array Express database. Affymetrix probe sets were mapped to Ensembl genes and transcripts using Ensembl-Biomart. Transcript 3'UTRs were searched for miR-122 seed matches[25] using in-house Perl scripts. When genes had alternative 3'UTRs only the longest sequence was used.

Example 6

Northern blot analysis and real-time RT-PCR. Trizol-extracted liver RNAs (10-15 µg per sample) were electrophoresed in 15% denaturing Novex TBE-Urea polyacrylamide gels (Invitrogen), transferred to Zeta Probe plus membrane (Biorad) and hybridized with 5' FAM-labelled LNA-modified miR-122 probe in Ultrahyb-oligo (Ambion) at 45° C. overnight. The membranes were washed 2×30 min in Low Stringency wash solution #1 (Ambion) at 45° C., rinsed twice in PBST and blocked in ECL advanced blocking solution (GE Healthcare Life Sciences) for one hour at room temperature and then rinsed twice in PBST. An antifluorescein-HRP antibody (PerkinElmer, NEF710) (1:1000 in blocking solution) was incubated with the membrane for one hour at room temperature, followed by rinsing twice in PBST, wash for 15 min and then 3×5 min in PBST at 25° C. The ECL advanced kit was used for detection (GE Healthcare Life Sciences), visualized on VersaDoc imaging system (Biorad). mRNA quantification was carried out using TaqMan assays and a 7500 real-time PCR instrument (Applied Biosystems).

Example 7

In vivo targeting of miR-122. To develop an efficient approach for miR-122 targeting in vivo, we first evaluated the potency of different LNA-modified DNA oligonucleotides (LNA-antimiRs) in cultured Huh-7 cells using a luciferase reporter assay for miR-122. Our screen implied that inhibition of miR-122 function was affinity dependent and identified a high-affinity LNA-antimiR (>50% LNA, $T_m$=80° C.), which mediated efficient derepression of the luciferase reporter at 5 nM concentration. This oligonucleotide showed improved potency compared to a 2'-O-methyl oligonucleotide and two LNA-antimiRs of lower affinity in inhibiting HCV replication in Huh-7 cells harboring the HCV-N replicon NNeo/C-5B. Moreover, when adapted to silencing of three additional miRNAs in HeLa cells, our LNA-antimiR design showed high potency for all targeted miRNAs.

Next, we asked whether combining the high-affinity LNA-antimiR with phosphorothioate (PS) modifications could enable in vivo delivery and silencing of miR-122 without additional conjugation chemistries. As shown in FIG. 1a, uptake of unconjugated LNA-antimiR in the murine liver was achieved by three intraperitoneal (i.p.) injections of saline-formulated LNA-antimiR with a complete PS backbone. This coincided with the detection of a shifted band on the Northern blot (FIG. 1a), indicating that the mature miR-122 is sequestered in a heteroduplex with LNA-antimiR.

LNA-mediated antagonism of miR-122 function led to three-fold de-repression of the direct miR-122 target aldolase A[6] (Aldoa) (FIG. 1b). Notably, single i.p. injections at doses ranging from 1 mg/kg to 200 mg/kg LNA-antimiR resulted in potent, dose-dependent and sustained reduction of total plasma cholesterol with an effective dose ($ED_{50}$) of 10 mg/kg (FIG. 1c). Moreover, i.p. delivered LNA-antimiR at doses ranging from three injections of 1 to 25 mg/kg showed markedly improved efficiency in antagonizing miR-122 compared to mice that were treated with either cholesterol-conjugated antagomir-122[6,21] or a phoshorothiolated LNA-antimiR with only 30% LNA and lower affinity[22] ($T_m$=70° C.) using the same dosing regimen. This is consistent with a previous report in mice in which efficient miR-122 silencing by antagomir-122 required much higher doses of 3×40 mg/kg to 3×80 mg/kg[21], whereas our findings demonstrate that LNA enables design of highly substituted LNA-antimiR oligonucleotides that can mediate potent miR-122 antagonism in vivo at a considerably lower dose.

Example 8

Antagonizing miR-122 in diet-induced obesity mice. To validate the conclusion in example 7, we antagonized miR-122 in a diet-induced obesity mouse model using two weekly i.p. doses of 5 mg/kg LNA-antimiR for six weeks, which resulted in efficient sequestration of mature miR-122 and sustained reduction of total cholesterol by 30% without any elevations in hepatotoxicity markers in the serum or in hepatic lipid accumulation (FIGS. 1d and 1e). In contrast, treatment with either saline or LNA mismatch control did not affect the cholesterol levels, concurring with detection of the mature miR-122 by northern blots in both groups (FIGS. 1d and 1e). The marked derepression of the miR-122 target genes, Aldoa (FIG. 1f) and Bckdk[22] (data not shown), in LNA-antimiR treated, but not in LNA mismatch treated mice, implies that antagonism of miR-122 in vivo by LNA-antimiR is specific. Consistent with this notion, clustering of the liver gene expression data revealed that all the LNA-antimiR-treated animals (n=5 per group) had highly similar expression profiles as shown by a uniform cluster on the same main branch of the dendrogram, which was divergent from the saline and LNA mismatch control groups (FIG. 1g). Antagonism or ectopic expression of a miRNA has previously been shown to result in increase or decrease of mRNAs, which show enrichment of miRNA seed matches in the 3' UTRs[6,7,22,23]. Indeed, correlating the presence of miR-122 seed matches with expression changes confirmed that messages with seed matches to miR-122 tended to be derepressed in the LNA antimiR-treated animals compared to those in control mice (FIG. 1h, Kolmogorod-Smirnov test p=2.4*10$^{-14}$ for seed+t1A+m8). This demonstrates that the liver mRNA changes in the LNA-antimiR treated mice are mainly due to silencing of miR-122.

Example 9

Primate studies. To ask if our LNA-antimiR approach could be used for miR-122 antagonism in non-human primates, we undertook an efficacy study in African green monkeys (*Chlorocebus aethiops*). Systemic administration of phosphate-buffered saline (PBS)-formulated LNA-antimiR in drug-naïve female African green monkeys by three intravenous injections at doses ranging from 1 to 10 mg/kg (n=5 per group) resulted in dose-dependent and sustained reduction of total plasma cholesterol in primates (FIG. 2a), which is consistent with the cholesterol lowering observed in miR-122 antagonized mice. Primates that received the high dose LNA-antimiR of 3×10 mg/kg showed maximum cholesterol reduction of 40% 23 days post treatment (p=0.001), whereas the middle dose group (3×3 mg/kg LNA-antimiR) showed 20% cholesterol lowering (p=0.02) at the same time point (FIG. 2a). Despite the observed fluctuations in total cholesterol levels over time, the effect on cholesterol lowering was clearly dose-dependent as shown by the cholesterol trend plots of each treatment group normalized to control monkeys (FIG. 2b). Northern blot analyses of RNA samples extracted from LNA-antimiR treated monkey liver biopsies performed 24 hours after last dose confirmed miR-122 silencing as demonstrated by dose-dependent accumulation of the shifted LNA-antimiR:miR-122 heteroduplex and depletion of mature miR-122 compared to saline-treated control monkey samples (FIG. 2c). In addition, in situ hybridization (ISH) in frozen monkey liver biopsies showed accumulation of the LNA-antimiR in the liver sections of treated monkeys, but not in saline controls (FIG. 2d), whereas high resolution ISH showed that the LNA-antimiR was primarily localized in the cytoplasm of primate hepatocytes (FIG. 2e).

Interestingly, LNA-mediated antagonism of miR-122 in primates was effective and long-lasting as measured by reduction of total plasma cholesterol for 7 weeks (p<0.05, two-sided t-test) in the high LNA-antimiR dose group and for 5 weeks (p<0.05) in the middle dose group (FIG. 2b). The cholesterol levels gradually returned towards baseline over a period of three months after LNA-antimiR treatment, which is consistent with normalization of mature miR-122 levels and clearance of the LNA-antimiR compound from the liver as detected by Northern blots and ISH, respectively, in a second set of monkey liver biopsies performed 96 days after initiation of LNA-antimiR treatment (FIG. 2c and data not shown). Decreases in both high-density lipoprotein (HDL) and its major apolipoprotein, Apo A-I as well as in low-density lipoprotein (LDL), and its principal apolipoprotein Apo B were detected in LNA-antimiR-treated monkeys, which concur with previous findings in miR-122 antagonized mice[5]. Although differences in the Apo A-I/Apo B ratios between the high dose and saline animals did not achieve statistical significance (p>0.05, two-sided t-test on each day), the ratio appeared to be slightly lower in the high dose group, suggesting a more pronounced effect on Apo A-I and HDL.

Example 10

Tox studies in the primate experiments. We observed no acute or subchronic toxicities in the LNA-antimiR treated primates as shown by the clinical chemistries, which remained within normal limits for all measurements throughout the study in the treatment groups, with the exception of transient, liver biopsy-associated spikes in creatine phosphokinase (CPK), AST, ALT, and bilirubin. Notably, there were no changes in blood coagulation profiles associated with LNA-antimiR treatment (FIG. 3a). Moreover, histopathology investigations of the liver biopsies revealed no treatment-correlated abnormalities in the LNA-antimiR treated primates (FIG. 3b). To dissociate any liver biopsy-associated toxicities in the safety evaluation of LNA-antimiR treatment, two additional non-biopsy groups (n=5) treated either with the high dose of 3×10 mg/kg LNA-antimiR or saline, respectively, were included in the primate study. We did not observe any hepatotoxicity or renal toxicity in these animals as demonstrated by absence of elevations in the plasma transaminases ALT and AST, bilirubin, CPK and creatinine after treatment with 3×10 mg/kg LNA-antimiR compared to saline controls (FIG. 3a). It is noteworthy, that all study animals tolerated both the LNA-antimiR compound and sample collection procedures well and all were in good health for at least ten months following LNA-antimiR treatment.

Example 11

Long term downregulation of virus titres in HCV infected Chimpanzees, by use of an anti miR-122 oligonucleotide. The study was designed to demonstrate proof of principle and determine antiviral potency. Each animal served as its own control, ie two placebo doses (saline) were administered during baseline prior to active treatment. The Chimpanzee was selected because, Chimpanzees is the only species (other than man) that can be infected by HCV and consequently the only animal model suitable for efficacy testing of drugs prior to use in humans, and because sequential homology of drug target in chimpanzee is most likely 100% to humans. The animals received 12 doses administered as intravenous infusions over 15 minutes, once a week, for 12 weeks. The low dose animal (4x0358) received 1 mg/kg body weight, the high dose animals (4x0513 and 4x0514) received 5 mg/kg body weight. Viremia was assessed as serum viral load once a week, and fortnightly in the last weeks of follow-up. It is reported in genomic equivalents [GE] of viral RNA per mL of serum. The oligonucleotide used for treatment in the Chimpanzees was a saline formulated LNA oligonucletide with the sequence: 5'-CcAttGTcaCaCtCC-3'. Virus titres was measured by quantitative real time PCR, employing a TaqMan probe. Samples were run in TaqMan assays using an ABI 7500 sequence detector as described (Lanford, R. E., Guerra, B., Lee, H., Averett, D. R., Pfeiffer, B., Chavez, D., Notvall, L., and Bigger, C. (2003). Antiviral effect and virus-host interaction in response to alpha interferon, gamma interferon, poly(I)-poly (C), tumor necrosis factor alpha, and ribavirin in hepatitis C virus subgenomic replicons. Journal of Virology 77, 1092-1104)

Data from titre measurements in the experimental animals are shown in FIG. 4.

Chimpanzee 4x0358, a low dose animal, did not exhibit significant declines in viral titre until day 70 when the level of viremia began to decline and remained below baseline until day 175, 12 weeks after last dose. The maximum reduction in viral titre occurred on d105 with a decrease of 34-fold. Viremia returned to 1.8-fold below baseline value by the end of the study period, day 210.

Chimpanzee 4x0513, a high dose animal, began to decline in viral titre after day 28. This animal exhibited a consistent decrease in viremia with maximum decrease occurring on day 98 with a 395-fold reduction in viremia. Viremia remained below baseline only slowly increasing to within 7.7-fold of baseline by the end of the study.

Chimpanzee 4x0514, a high dose animal, exhibited a profile similar to 4x0513. A consistent decrease in viremia began at day 28 and continued with a maximum decrease occurring on day 92 with a 317-fold reduction in viremia. As with 4x0513, viremia then remained low, slowly increasing to baseline values by the end of the study.

In conclusion, the treated animals all showed decreased viremia as a consequence of active treatment. Onset of effect became apparent between study day 28 and 70, depending on dose. The viremia remained lowered well beyond end of active treatment, and effect was sustained for a minimum of 8 weeks.

Example 12

Administration to a patient, of an oligonucleotide according to the invention. microRNA's are involved in the pathology of many different diseases, as described in Table 1, and as a consequence thereof, antimicroRNA compounds against different microRNA's may have utility in the treatment of such diseases. In order to treat a patient effectively, i.e. to optimize the correct dosage level and frequency of administration for individual patients, it is necessary to determine some disease parameters that are useful for evaluating the effect of the treatment on the disease. For the initial calculations of the desired effective dosage schedule in an individual patient suffering from a disease that may be treated with a microRNA modulating compound, the skilled person may chose to measure a disease parameter that is influenced by the treatment, and use such measurements for assessment of treatment efficacy. The person skilled in administration of such drugs is trained to calculate such dosing schedules, and to monitor treatment efficacy, and will do so using the information generated during the clinical development process. Different parameters will be useful for calculating such dosages and the time interval between each maintenance dosing. Calculating the optimum dosing schedule for the individual patient based on the knowledge obtained in the clinical experiments prior to market authorization, is routine for the skilled person, who may use some of the following information: maximum tolerated dosage, half-life of the compound in circulation and in target tissues, measurable disease parameters useful for assessment of efficacy of treatment. Most of these parameters and calculations are routine for the skilled person to take into consideration.

The present invention relates to the treatment schedule in the maintenance period, which is the phase of the treatment that occur after the initial dosage build up phase, where a level of maintenance dosing for the continued treatment in the individual patient must be calculated. The maintenance dosage may be designed to maintain a high level of compound in the target tissue, in order to maintain symptoms of the disease at a low level, or it may be designed to keep symptom regression for a period until symptoms either disappear, or reach a low acceptable level, after which in some cases, the dosage may be reduced, or the frequency of administration may be reduced further, or both. Different parameters will be useful for calculating the dosage and the time interval between each maintenance dosing. Based on the knowledge about the maximum tolerated dosage, half-life of the compound in circulation and in target tissues, measurable disease parameters useful for assessment of efficacy of treatment, which is obtained in the clinical experiments prior to market authorization, the skilled person will be able to calculate the optimum dosing schedule for the individual patient.

The invention claimed is:

1. A method of lowering of the activity of a microRNA target in vivo in a primate, comprising administering to the primate at least two successive effective doses of an antisense oligonucleotide targeting the microRNA target, wherein
   (a) the antisense oligonucleotide is essentially incapable of recruiting RNAseH,
   (b) at least 30% of the nucleotide monomers in the antisense oligonucleotide are LNA monomers,
   (c) the antisense oligonucleotide has a length of 7 to 25 nucleotides,
   (d) the antisense oligonucleotide does not comprise a region of more than 4 consecutive DNA monomers, and
   (e) the antisense oligonucleotide comprises a fully phosphorothioated backbone,
   and wherein the at least two successive effective doses of the antisense oligonucleotide are administered to the primate with a time interval of at least two weeks between the doses, and an effective target tissue concentration of the antisense oligonucleotide is maintained between the doses.

2. The method according to claim 1, wherein the time interval between each administration is at least four weeks, at least one month, at least two months, at least three months, or at least four months.

3. The method according to claim 1, wherein the microRNA is selected from the group consisting of miR-1, Let-7, miR-21, miR-21, miR-200b and miR-141, miR-122, miR-19b, miR-26a, miR-155, miR-203, miR-375, miR-181, miR-10b, miR-125b-1, miR-221 and 222, miRNA-372 and -373, miR-142, miR-1719b cluster, miR-17-5p, miR-20a/b, miR-93, miR-106a/b, miR-18a/b, miR-19a/b, miR-25, miR-92a, and miR-363.

4. The method according to claim 1, wherein the microRNA is miR-122.

5. The method according to claim 4, wherein the antisense oligonucleotide comprises SEQ ID NO: 11.

6. The method according to claim 4, wherein the antisense oligonucleotide consists of SEQ ID NO: 11.

7. The method according to claim 1, wherein the antisense oligonucleotide further comprises one or more nucleotide monomers selected from the group consisting of DNA monomers, 2'-O-alkyl-RNA monomers, 2-OMe-RNA monomers, 2'-amino-DNA monomers, 2'-fluoro-DNA monomers, PNA monomers, arabino nucleic acid (ANA) monomers, 2'-fluoro-ANA monomers, HNA monomers, 2'-MOE-RNA (2'-O-methoxyethyl-RNA) monomers, and INA monomers.

8. The method according to claim 1, wherein all the non-LNA nucleotide monomers are independently selected from the group consisting of 2'-MOE-RNA (2'-O-methoxyethyl-RNA) monomers, and 2'-Fluoro-DNA monomers.

9. The method according to claim 7, wherein the LNA monomers are beta-D-oxy LNA monomers.

10. A method of treating a disease or disorder in vivo in a primate, wherein the disease or disorder is associated with the expression or over-expression of a target microRNA, comprising administering to the primate at least two successive effective doses of an antisense oligonucleotide targeting the microRNA target, wherein
   (a) the antisense oligonucleotide is essentially incapable of recruiting RNAseH,
   (b) at least 30% of the nucleotide monomers in the antisense oligonucleotide are LNA monomers,
   (c) the antisense oligonucleotide has a length of 7 to 25 nucleotides,
   (d) the antisense oligonucleotide does not comprise a region of more than 4 consecutive DNA monomers, and
   (e) the antisense oligonucleotide comprises a fully phosphorothioated backbone,
   and wherein the at least two successive effective doses of the antisense oligonucleotide are administered to the primate with a time interval of at least two weeks between the doses, and an effective target tissue concentration of the antisense oligonucleotide is maintained between the doses.

11. The method according to claim 10 wherein the time interval between each administration is at least four weeks, at least one month, at least two months, at least three months, or at least four months.

12. The method according to claim 10, wherein the microRNA is selected from the group consisting of miR-1, Let-7, miR-21, miR-21, miR-200b and miR-141, miR-122, miR-19b, miR-26a, miR-155, miR-203, miR-375, miR-181, miR-10b, miR-125b-1, miR-221 and 222, miRNA-372 and -373, miR-142, miR-1719b cluster, miR-175p, miR-20a/b, miR-93, miR-106a/b, miR-18a/b, miR -19a/b, miR-25, miR-92a, and miR-363.

13. The method according to claim 10, wherein the disease or disorder is selected from the group consisting of glioblastoma, breast cancer, hepatocellular carcinoma, colorectal cancer, glioma, cholangiocarcinoma, lymphoma, pancreatic tumor, lung cancer, ovarian cancer, cervical cancer, prostate carcinoma, human thyroid papillary carcinoma, hepatocellular carcinoma, testicular germ cell tumor, and leukemia.

14. The method according to claim 10, wherein the disease or disorder is selected from the group consisting of cardiac arrhythmia, cardiac hypertrophy, cancer, hypercholesterolemia, metabolic disorders, psoriasis, diabetes, auto immune disorders, hemochromatosis, and hepatitis C infection.

15. The method according to claim 10, wherein the disease or disorder is selected from the group consisting of metabolic disorders, hypercholesterolemia, hemochromatosis, and hepatitis C infection.

16. The method according to claim 10, wherein the microRNA is miR-122.

17. The method according to claim 16, wherein the antisense oligonucleotide comprises SEQ ID NO: 11.

18. The method according to claim 16, wherein the antisense oligonucleotide consists of SEQ ID NO: 11.

19. The method according to claim 10, wherein the antisense oligonucleotide further comprises one or more nucleotide monomers selected from the group consisting of DNA monomers, 2'-O-alkyl-RNA monomers, 2-OMe-RNA monomers, 2'-amino-DNA monomers, 2'-fluoro-DNA monomers, PNA monomers, arabino nucleic acid (ANA) monomers, 2'-fluoro-ANA monomers, HNA monomers, 2'MOE-RNA (2'-O-methoxyethyl-RNA) monomers, and INA monomers.

20. The method according to claim 10, wherein all the non-LNA nucleotide monomers are independently selected from the group consisting of 2'-MOE-RNA (2'-O-methoxyethyl-RNA) monomers, and 2'-Fluoro-DNA monomers.

21. The method according to claim 19, wherein the LNA monomers are beta-D-oxy LNA monomers.

22. The method according to claim 1, wherein the primate microRNA is a human microRNA.

23. The method according to claim 10, wherein the primate microRNA is a human microRNA.

24. The method according to claim 1, wherein the cytosine LNA monomers are 5-methylcytosines.

25. The method according to claim 4, wherein the antisense oligonucleotide is:
5'-CcAttGTcaCaCtCC-3' (SEQ ID NO: 202)
wherein capital letters are beta-D-oxy LNA monomers, and cytosine LNA monomers are 5'methylcytosines, wherein small letters are DNA monomers, and wherein all internucleoside linkages are phosphorothioate linkages.

26. The method according to claim 10, wherein the cytosine LNA monomers are 5-methylcytosines.

27. The method according to claim 16, wherein the antisense oligonucleotide is:
5'-CcAttGTcaCaCtCC-3' (SEQ ID NO: 202)
wherein capital letters are beta-D-oxy LNA monomers, and cytosine LNA monomers are 5'-methylcytosines, wherein small letters are DNA monomers, and wherein all internucleoside linkages are phosphorothioate linkages.

28. The method according to claim 1, wherein the antisense oligonucleotide has a length of 10 to 16 nucleotides.

29. The method according to claim 10, wherein the antisense oligonucleotide has a length of 10 to 16 nucleotides.

30. The method according to claim 1, wherein the antisense oligonucleotide has a length of 8 to 16 nucleotides.

31. The method according to claim 10, wherein the antisense oligonucleotide has a length of 8 to 16 nucleotides.

32. The method according to claim 1, wherein the antisense oligonucleotide has a length of 7 to 10 nucleotides.

33. The method according to claim 10, wherein the antisense oligonucleotide has a length of 7 to 10 nucleotides.

34. The method according to claim 1, wherein at least 50% of the nucleotide monomers in the antisense oligonucleotide are LNA monomers.

35. The method according to claim 10, wherein at least 50% of the nucleotide monomers in the antisense oligonucleotide are LNA monomers.

36. The method according to claim 1, wherein at least 70% of the nucleotide monomers in the antisense oligonucleotide are LNA monomers.

37. The method according to claim 10, wherein at least 70% of the nucleotide monomers in the antisense oligonucleotide are LNA monomers.

38. The method according to claim 1, wherein all the nucleotide monomers in the antisense oligonucleotide are LNA monomers and the antisense oligonucleotide has a length of 7 to 10 nucleotides.

39. The method according to claim 10, wherein all the nucleotide monomers in the antisense oligonucleotide are LNA monomers and the antisense oligonucleotide has a length of 7 to 10 nucleotides.

40. The method according to claim 1, wherein the antisense oligonucleotide does not comprise a region of more than 3 consecutive DNA monomers.

41. The method according to claim 10, wherein the antisense oligonucleotide does not comprise a region of more than 3 consecutive DNA monomers.

42. The method according to claim 1, wherein the antisense oligonucleotide does not comprise a region of more than 2 consecutive DNA monomers.

43. The method according to claim 10, wherein the antisense oligonucleotide does not comprise a region of more than 2 consecutive DNA monomers.

44. The method according to claim 1, wherein all the non-LNA nucleotide monomers in the antisense oligonucleotide are independently selected from the group consisting of DNA monomers, 2'-O-alkyl-RNA monomers, 2-OMe-RNA monomers, 2'-amino-DNA monomers, 2'-fluoro-DNA monomers, PNA monomers, arabino nucleic acid (ANA) monomers, 2'-fluoro-ANA monomers, HNA monomers, 2'-MOE-RNA (2'-O-methoxyethyl-RNA) monomers, and INA monomers.

45. The method according to claim 8, wherein the LNA monomers are beta-D-oxy LNA monomers.

46. The method according to claim 44, wherein the LNA monomers are beta-D-oxy LNA monomers.

47. The method according to claim 10, wherein all the non-LNA nucleotide monomers in the antisense oligonucleotide are independently selected from the group consisting of DNA monomers, 2'-O-alkyl-RNA monomers, 2-OMe-RNA monomers, 2-'-amino-DNA monomers, 2'-fluoro-DNA monomers, PNA monomers, arabino nucleic acid (ANA) monomers, 2'-fluoro-ANA monomers, HNA monomers, 2'-MOE-RNA (2'-O-methoxyethyl-RNA) monomers, and INA monomers.

48. The method according to claim 20, wherein the LNA monomers are beta-D-oxy LNA monomers.

49. The method according to claim 47, wherein the LNA monomers are beta-D-oxy LNA monomers.

* * * * *

SEQUENCE LISTING

```
<160> NUMBER OF SEQ ID NOS: 202

<210> SEQ ID NO 1
<211> LENGTH: 23
<212> TYPE: RNA
<213> ORGANISM: Homo sapiens

<400> SEQUENCE: 1
uguuuguggu aacaguguga ggu                                           23
```

```
<210> SEQ ID NO 2
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: fully phosphorothioate, LNA/DNA oligomer

<400> SEQUENCE: 2
attgtcacac tcc                                                        13

<210> SEQ ID NO 3
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 3
ccattgtcac actcc                                                      15

<210> SEQ ID NO 4
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: fully phosphorothioate, LNA/DNA oligomer

<400> SEQUENCE: 4
attgtcacac tcc                                                        13

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: fully phosphorothioate, LNA/DNA oligomer

<400> SEQUENCE: 5
ccattgtcac actcca                                                     16

<210> SEQ ID NO 6
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 6
ccattgtcac cctcc                                                      15
```

```
<210> SEQ ID NO 7
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 7
ccattgtcac actcc                                                        15

<210> SEQ ID NO 8
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: fully phosphorothioate, LNA/DNA oligomer

<400> SEQUENCE: 8
attgtcacac tcc                                                          13

<210> SEQ ID NO 9
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: fully phosphorothioate, LNA/DNA oligomer

<400> SEQUENCE: 9
attgtcacac tcc                                                          13

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: fully phosphorothioate, LNA/DNA oligomer

<400> SEQUENCE: 10
ccattgtcac actcca                                                       16

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 11
ccattgtcac actcc                                                        15
```

```
<210> SEQ ID NO 12
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 12 ttacattcc                                                                 9

<210> SEQ ID NO 13
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 13 aagcacttt                                                                 9

<210> SEQ ID NO 14
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 14 tacattgca                                                                 9

<210> SEQ ID NO 15
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 15 cagcacttt                                                                 9

<210> SEQ ID NO 16
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 16 cacagtgcg                                                                 9
```

```
<210> SEQ ID NO 17
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 17 ctacagggt                                                                  9

<210> SEQ ID NO 18
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 18 tcacactcc                                                                  9

<210> SEQ ID NO 19
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 19 gtctcaggg                                                                  9

<210> SEQ ID NO 20
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 20 gacagtgtt                                                                  9

<210> SEQ ID NO 21
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 21 ctggaagat                                                                  9
```

```
<210> SEQ ID NO 22
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 22 aaacactac                                                                 9

<210> SEQ ID NO 23
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 23 ctactttat                                                                 9

<210> SEQ ID NO 24
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 24 ttagcatta                                                                 9

<210> SEQ ID NO 25
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 25 aagcacttt                                                                 9

<210> SEQ ID NO 26
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 26 tcactgcag                                                                 9
```

```
<210> SEQ ID NO 27
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 27 gttgaatgt                                                                 9

<210> SEQ ID NO 28
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 28 ggtcgatgg                                                                 9

<210> SEQ ID NO 29
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 29 ggtcagtgg                                                                 9

<210> SEQ ID NO 30
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 30 aatgaatgt                                                                 9

<210> SEQ ID NO 31
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 31 gttgaatgt                                                                 9
```

```
<210> SEQ ID NO 32
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 32 gtcgatggt                                                                9

<210> SEQ ID NO 33
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 33 atgcacctt                                                                9

<210> SEQ ID NO 34
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 34 ttagggcag                                                                9

<210> SEQ ID NO 35
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 35 atgcacctt                                                                9

<210> SEQ ID NO 36
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 36 atttagggc                                                                9
```

```
<210> SEQ ID NO 37
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 37 gatttgcac                                                                 9

<210> SEQ ID NO 38
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 38 atgcaaaac                                                                 9

<210> SEQ ID NO 39
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 39 gatttgcac                                                                 9

<210> SEQ ID NO 40
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 40 ggcagtatt                                                                 9

<210> SEQ ID NO 41
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 41 aacatttca                                                                 9
```

```
<210> SEQ ID NO 42
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 42 aagcacttt                                                          9

<210> SEQ ID NO 43
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 43 ataatgcag                                                          9

<210> SEQ ID NO 44
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 44 gagcacttt                                                          9

<210> SEQ ID NO 45
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 45 atactacag                                                          9

<210> SEQ ID NO 46
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 46 tgataagct                                                          9
```

```
<210> SEQ ID NO 47
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 47 caatgtagc                                                                 9

<210> SEQ ID NO 48
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 48 tatgccagg                                                                 9

<210> SEQ ID NO 49
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 49 agatgtagc                                                                 9

<210> SEQ ID NO 50
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 50 ggctactga                                                                 9

<210> SEQ ID NO 51
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 51 aagtgcaat                                                                 9
```

```
<210> SEQ ID NO 52
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 52 attacttga                                                                 9

<210> SEQ ID NO 53
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 53 ccgtgcaat                                                                 9

<210> SEQ ID NO 54
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 54 gcagcactt                                                                 9

<210> SEQ ID NO 55
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 55 gaagcactt                                                                 9

<210> SEQ ID NO 56
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 56 cattttgag                                                                 9
```

```
<210> SEQ ID NO 57
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 57 aacgaacaa                                                           9

<210> SEQ ID NO 58
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 58 aagtgcaat                                                           9

<210> SEQ ID NO 59
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 59 atcccaacc                                                           9

<210> SEQ ID NO 60
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 60 atccccacc                                                           9

<210> SEQ ID NO 61
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 61 cagcacttt                                                           9
```

```
<210> SEQ ID NO 62
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 62 tacattcc                                                                 8

<210> SEQ ID NO 63
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 63 agcacttt                                                                 8

<210> SEQ ID NO 64
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 64 acattgca                                                                 8

<210> SEQ ID NO 65
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 65 agcacttt                                                                 8

<210> SEQ ID NO 66
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 66 acagtgcg                                                                 8
```

<210> SEQ ID NO 67
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 67 tacagggt                                                                  8

<210> SEQ ID NO 68
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 68 cacactcc                                                                  8

<210> SEQ ID NO 69
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 69 tctcaggg                                                                  8

<210> SEQ ID NO 70
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 70 acagtgtt                                                                  8

<210> SEQ ID NO 71
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 71 tggaagat                                                                  8

```
<210> SEQ ID NO 72
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 72 aacactac                                                                 8

<210> SEQ ID NO 73
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 73 tactttat                                                                 8

<210> SEQ ID NO 74
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 74 tagcatta                                                                 8

<210> SEQ ID NO 75
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 75 agcacttt                                                                 8

<210> SEQ ID NO 76
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 76 cactgcag                                                                 8
```

```
<210> SEQ ID NO 77
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 77 ttgaatgt                                                                 8

<210> SEQ ID NO 78
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 78 gtcgatgg                                                                 8

<210> SEQ ID NO 79
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 79 gtcagtgg                                                                 8

<210> SEQ ID NO 80
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 80 atgaatgt                                                                 8

<210> SEQ ID NO 81
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 81 ttgaatgt                                                                 8
```

```
<210> SEQ ID NO 82
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 82 tcgatggt                                                                  8

<210> SEQ ID NO 83
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 83 tgcacctt                                                                  8

<210> SEQ ID NO 84
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 84 tagggcag                                                                  8

<210> SEQ ID NO 85
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 85 tgcacctt                                                                  8

<210> SEQ ID NO 86
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 86 tttagggc                                                                  8
```

```
<210> SEQ ID NO 87
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 87 atttgcac                                                                 8

<210> SEQ ID NO 88
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 88 tgcaaaac                                                                 8

<210> SEQ ID NO 89
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 89 atttgcac                                                                 8

<210> SEQ ID NO 90
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 90 gcagtatt                                                                 8

<210> SEQ ID NO 91
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 91 acatttca                                                                 8
```

```
<210> SEQ ID NO 92
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 92 agcacttt                                                                 8

<210> SEQ ID NO 93
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 93 taatgcag                                                                 8

<210> SEQ ID NO 94
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 94 agcacttt                                                                 8

<210> SEQ ID NO 95
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 95 tactacag                                                                 8

<210> SEQ ID NO 96
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 96 gataagct                                                                 8
```

```
<210> SEQ ID NO 97
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 97 aatgtagc                                                                 8

<210> SEQ ID NO 98
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 98 atgccagg                                                                 8

<210> SEQ ID NO 99
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 99 gatgtagc                                                                 8

<210> SEQ ID NO 100
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 100 gctactga                                                                 8

<210> SEQ ID NO 101
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 101 agtgcaat                                                                 8
```

```
<210> SEQ ID NO 102
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 102 ttacttga                                                                8

<210> SEQ ID NO 103
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 103 cgtgcaat                                                                8

<210> SEQ ID NO 104
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 104 cagcactt                                                                8

<210> SEQ ID NO 105
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 105 aagcactt                                                                8

<210> SEQ ID NO 106
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 106 attttgag                                                                8
```

```
<210> SEQ ID NO 107
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 107 acgaacaa                                                                 8

<210> SEQ ID NO 108
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 108 agtgcaat                                                                 8

<210> SEQ ID NO 109
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 109 tcccaacc                                                                 8

<210> SEQ ID NO 110
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 110 tccccacc                                                                 8

<210> SEQ ID NO 111
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 111 agcacttt                                                                 8
```

```
<210> SEQ ID NO 112
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 112 acattcc                                                                 7

<210> SEQ ID NO 113
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 113 gcacttt                                                                 7

<210> SEQ ID NO 114
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 114 cattgca                                                                 7

<210> SEQ ID NO 115
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 115 gcacttt                                                                 7

<210> SEQ ID NO 116
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 116 cagtgcg                                                                 7
```

```
<210> SEQ ID NO 117
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 117 acagggt                                                                    7

<210> SEQ ID NO 118
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 118 acactcc                                                                    7

<210> SEQ ID NO 119
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 119 ctcaggg                                                                    7

<210> SEQ ID NO 120
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 120 cagtgtt                                                                    7

<210> SEQ ID NO 121
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 121 ggaagat                                                                    7
```

```
<210> SEQ ID NO 122
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 122 acactac                                                                 7

<210> SEQ ID NO 123
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 123 actttat                                                                 7

<210> SEQ ID NO 124
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 124 agcatta                                                                 7

<210> SEQ ID NO 125
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 125 gcacttt                                                                 7

<210> SEQ ID NO 126
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 126 actgcag                                                                 7
```

```
<210> SEQ ID NO 127
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 127 tgaatgt                                                                  7

<210> SEQ ID NO 128
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 128 tcgatgg                                                                  7

<210> SEQ ID NO 129
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 129 tcagtgg                                                                  7

<210> SEQ ID NO 130
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 130 tgaatgt                                                                  7

<210> SEQ ID NO 131
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 131 tgaatgt                                                                  7
```

```
<210> SEQ ID NO 132
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 132 cgatggt                                                                 7

<210> SEQ ID NO 133
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 133 gcacctt                                                                 7

<210> SEQ ID NO 134
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 134 agggcag                                                                 7

<210> SEQ ID NO 135
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 135 gcacctt                                                                 7

<210> SEQ ID NO 136
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 136 ttagggc                                                                 7
```

```
<210> SEQ ID NO 137
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 137 tttgcac                                                                 7

<210> SEQ ID NO 138
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 138 gcaaaac                                                                 7

<210> SEQ ID NO 139
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 139 tttgcac                                                                 7

<210> SEQ ID NO 140
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 140 cagtatt                                                                 7

<210> SEQ ID NO 141
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 141 catttca                                                                 7
```

```
<210> SEQ ID NO 142
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 142 gcacttt                                                                 7

<210> SEQ ID NO 143
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 143 aatgcag                                                                 7

<210> SEQ ID NO 144
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 144 gcacttt                                                                 7

<210> SEQ ID NO 145
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 145 actacag                                                                 7

<210> SEQ ID NO 146
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 146 ataagct                                                                 7
```

```
<210> SEQ ID NO 147
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 147 atgtagc                                                                   7

<210> SEQ ID NO 148
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 148 tgccagg                                                                   7

<210> SEQ ID NO 149
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 149 atgtagc                                                                   7

<210> SEQ ID NO 150
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 150 ctactga                                                                   7

<210> SEQ ID NO 151
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 151 gtgcaat                                                                   7
```

```
<210> SEQ ID NO 152
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 152 tacttga                                                                7

<210> SEQ ID NO 153
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 153 gtgcaat                                                                7

<210> SEQ ID NO 154
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 154 agcactt                                                                7

<210> SEQ ID NO 155
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 155 agcactt                                                                7

<210> SEQ ID NO 156
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 156 ttttgag                                                                7
```

```
<210> SEQ ID NO 157
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 157 cgaacaa                                                                  7

<210> SEQ ID NO 158
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 158 gtgcaat                                                                  7

<210> SEQ ID NO 159
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 159 cccaacc                                                                  7

<210> SEQ ID NO 160
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 160 ccccacc                                                                  7

<210> SEQ ID NO 161
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 161 gcacttt                                                                  7
```

<210> SEQ ID NO 162
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 162
tcagtctgat aagct                                                          15

<210> SEQ ID NO 163
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 163 gataagct                                                                   8

<210> SEQ ID NO 164
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 164
tcacaattag catta                                                          15

<210> SEQ ID NO 165
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 165 tagcatta                                                                   8

<210> SEQ ID NO 166
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 166
ccattgtcac actcc                                                          15

```
<210> SEQ ID NO 167
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 167 cacactcc                                                                 8

<210> SEQ ID NO 168
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 168 ataagct                                                                  7

<210> SEQ ID NO 169
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 169 tgataagct                                                                9

<210> SEQ ID NO 170
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: fully phosphorothioate LNA oligomer

<400> SEQUENCE: 170
ctgataagct                                                              10

<210> SEQ ID NO 171
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: fully phosphorothioate LNA oligomer

<400> SEQUENCE: 171
gtctgataag ct                                                           12
```

```
<210> SEQ ID NO 172
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: fully phosphorothioate LNA oligomer

<400> SEQUENCE: 172
cagtctgata agct                                                        14

<210> SEQ ID NO 173
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 173 tctgataa                                                                8

<210> SEQ ID NO 174
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 174 atcagtct                                                                8

<210> SEQ ID NO 175
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 175 tcaacatc                                                                8

<210> SEQ ID NO 176
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 176 agcacttt                                                                8
```

```
<210> SEQ ID NO 177
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 177 atttgcac                                                                8

<210> SEQ ID NO 178
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 178
agcagacaat gtagc                                                       15

<210> SEQ ID NO 179
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 179
gtagccagat gtagc                                                       15

<210> SEQ ID NO 180
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 180 atgtagc                                                                 7

<210> SEQ ID NO 181
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 181
acaacctact acctc                                                       15
```

```
<210> SEQ ID NO 182
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: fully phosphorothioate LNA oligomer

<400> SEQUENCE: 182 actacctc                                                                  8

<210> SEQ ID NO 183
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 183
cactgtcagc acttt                                                         15

<210> SEQ ID NO 184
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 184
tgcatagatt tgcac                                                         15

<210> SEQ ID NO 185
<211> LENGTH: 6
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: fully phosphorothioate LNA oligomer

<400> SEQUENCE: 185 tacctc                                                                    6

<210> SEQ ID NO 186
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 186 ctacctc                                                                   7
```

```
<210> SEQ ID NO 187
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer
<220> FEATURE:
<221> NAME/KEY: misc_feature
<222> LOCATION: (2)..(2)
<223> OTHER INFORMATION: n is a, c, g, or t

<400> SEQUENCE: 187 tnctacctc                                                                 9

<210> SEQ ID NO 188
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer
<220> FEATURE:
<221> NAME/KEY: misc_feature
<222> LOCATION: (2)..(2)
<223> OTHER INFORMATION: n is a, c, g, or t

<400> SEQUENCE: 188 tnctacctc                                                                 9

<210> SEQ ID NO 189
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 189
gcaacctact acctc                                                         15

<210> SEQ ID NO 190
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer

<400> SEQUENCE: 190
acaacctcct acctc                                                         15

<210> SEQ ID NO 191
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (1)..(15)
<223> OTHER INFORMATION: fully phosphorothioate, LNA/DNA oligomer

<400> SEQUENCE: 191
acaaactact acctc                                                          15

<210> SEQ ID NO 192
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 192 ctacctc                                                                    7

<210> SEQ ID NO 193
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 193 ctaactc                                                                    7

<210> SEQ ID NO 194
<211> LENGTH: 9
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: fully phosphorothioate LNA oligomer

<400> SEQUENCE: 194 ttagcatta                                                                  9

<210> SEQ ID NO 195
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: fully phosphorothioate LNA oligomer

<400> SEQUENCE: 195
cgattagcat ta                                                             12

<210> SEQ ID NO 196
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (1)..(14)
<223> OTHER INFORMATION: fully phosphorothioate LNA oligomer

<400> SEQUENCE: 196
cacgattagc atta                                                        14

<210> SEQ ID NO 197
<211> LENGTH: 6
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: fully phosphorothioate LNA oligomer

<400> SEQUENCE: 197 gcatta                                                                  6

<210> SEQ ID NO 198
<211> LENGTH: 7
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: fully phosphorothioate LNA oligomer

<400> SEQUENCE: 198 agcatta                                                                 7

<210> SEQ ID NO 199
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: fully phosphorothioate LNA oligomer

<400> SEQUENCE: 199
attagcatta                                                             10

<210> SEQ ID NO 200
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: mismatch oligo
<220> FEATURE:
<221> NAME/KEY: misc_feature
<222> LOCATION: (1)..(15)
<223> OTHER INFORMATION: Fully phoshorothioate LNA/DNA oligomer

<400> SEQUENCE: 200
ccattctcac actgc                                                       15

<210> SEQ ID NO 201
<211> LENGTH: 15
<212> TYPE: DNA
<213> ORGANISM: Artificial sequence
<220> FEATURE:
```

```
<223> OTHER INFORMATION: Synthetic oligonucleotide
<220> FEATURE:
<223> OTHER INFORMATION: LNA control oligo
<220> FEATURE:
<221> NAME/KEY: misc_feature
<222> LOCATION: (1)..(15)
<223> OTHER INFORMATION: Fully phosphorothioate LNA/DNA oligomer

<400> SEQUENCE: 201
ccattctgac cctac                                                    15

<210> SEQ ID NO 202
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: fully phosphorothioate, LNA/DNA oligomer
<220> FEATURE:
<223> OTHER INFORMATION: beta-D-oxy LNA nucleosides at nucleotide
      positions 1, 3, 6, 7, 10, 12, 14 and 15. LNA cytosines at
      nucleotide positions 1, 10, 12, 14 and 15 are 5'methyl cytosines.

<400> SEQUENCE: 202
ccattgtcac actcc                                                    15
```